(12) United States Patent
Diebold et al.

(10) Patent No.: US 8,293,904 B2
(45) Date of Patent: Oct. 23, 2012

(54) ELECTROCHEMICAL AFFINITY BIOSENSOR SYSTEM AND METHODS

(75) Inventors: Eric R. Diebold, Fishers, IN (US); Mitali Ghoshal, Noblesville, IN (US); David Z. Deng, Weston, FL (US); Jane S. C. Tsai, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/236,838

(22) Filed: Sep. 20, 2011

(65) Prior Publication Data
US 2012/0125788 A1     May 24, 2012

Related U.S. Application Data

(62) Division of application No. 10/555,138, filed as application No. PCT/US2004/021187 on Jul. 1, 2004.

(60) Provisional application No. 60/484,096, filed on Jul. 1, 2003.

(51) Int. Cl.
C07F 15/00     (2006.01)
G01N 27/26     (2006.01)
C07K 14/00     (2006.01)

(52) U.S. Cl. ......... 546/10; 548/101; 205/775; 530/409

(58) Field of Classification Search ............. 546/10; 548/101; 205/775; 530/409
See application file for complete search history.

(56) References Cited

U.S. PATENT DOCUMENTS

| 5,262,035 A | 11/1993 | Gregg et al. |
| 5,589,326 A | 12/1996 | Deng et al. |
| 2003/0096997 A1 | 5/2003 | Mao et al. |

FOREIGN PATENT DOCUMENTS

WO     WO 96/25514 A     8/1996

OTHER PUBLICATIONS

Tansil et al. "Direct Detection of DNA with an Electrocatalytic Threading Intercalator" Anal. Chem., 2005, vol. 77, pp. 126-134.*
Csoregi et al., Anal. Chem. 1994, vol. 66, pp. 3131-3138.
Nakabayashi et al., Sensors and Actuators B66 (2000), pp. 128-130.
Tansil et al., Anal. Chem. 2005, vol. 77, pp. 126-134.

* cited by examiner

*Primary Examiner* — Joseph Kosack
(74) *Attorney, Agent, or Firm* — Woodard Emhardt Moriarty McNett & Henry LLP

(57) ABSTRACT

The present invention provides novel osmium-based electrochemical species for the detection of wide variety of analytes using immunological techniques. The present invention also provides diagnostic kits and test sensors supporting electrode structures that can be used with the osmium-based electrochemical species. The test sensor can be fabricated to support interdigitated arrays of electrodes that have been designed to provide amplification of the electrical signal amplification desired to analyze analytes that may be present at low concentrations.

8 Claims, 50 Drawing Sheets

| Electrode | Electrode pairs # | Gap Width (μM) | Band width (μm) | Band Length (mm) | Total area of fingers 1 electrode (mm²) | Physical area if fingers (mm²) | Predicted Slope from Equation (nA/μM) | Experimental Slope¹ from recycling CV (nA/μM) | Experimental Slope² of Dose Response (nA/μM) | Normalized Experimental Slope (nA/μm/mm²) | Normalized Experimental Slope (nA/μm/mm²) | Comments |
|---|---|---|---|---|---|---|---|---|---|---|---|---|
| VIDA Si-wafer/some Cr removed | 46 | 1.2 | 50 | 2.55 | 5.865 | 11.73 | 16.9 | 12 | | 1.44 | 1.02 | h |
| VIDA Si-wafer/some Cr removed | 46 | 1.5 | 50 | 2.55 | 5.865 | 11.73 | 16.1 | 11 | | 1.37 | 0.94 | h |
| VIDA Si-wafer/some Cr removed | 46 | 2.5 | 50 | 2.55 | 5.865 | 11.73 | 14.3 | 12 | | 1.22 | 1.02 | h |
| VIDA Si-wafer/some Cr removed | 46 | 1.2 | 50 | 2.55 | 5.865 | 11.73 | 16.9 | | 7.4-10 | 1.44 | 0.63-0.85 | i |
| VIDA Si-wafer/some Cr removed | 46 | 1.2 | 50 | 2.55 | 5.865 | 11.73 | 16.9 | | 2-7 | 1.44 | 0.17-0.6 | i |
| VIDA Si-wafer/some Cr removed | 46 | 2.5 | 50 | 2.55 | 5.865 | 11.73 | 14.3 | | 4-7.3 | 1.22 | 0.34-0.63 | k |
| VIDA Kapton substrate | 46 | 3 | 50 | 2.55 | 5.865 | 11.73 | 13.7 | 14 | | 1.17 | 1.19 | l |
| VIDA Kapton substrate | 46 | 3 | 50 | 2.55 | 5.865 | 11.73 | 13.7 | | 7.6 | 1.17 | 0.65 | l |
| IDA | 50 | 10 | 21 | 6 | 6.3 | 18.6 | 18.8 | 20 | | 1.01 | 1.08 | a |
| IDA | 50 | 15 | 21 | 6 | 6.3 | 21.6 | 16.2 | 17 | | 0.75 | 0.79 | a |
| IDA | 50 | 21 | 21 | 6 | 6.3 | 25.2 | 14.3 | 14 | | 0.57 | 0.56 | a |
| IDA | 50 | 10 | 21 | 6 | 6.3 | 18.6 | 18.8 | | 17.8 | 1.01 | 0.96 | b |
| IDA | 50 | 15 | 21 | 6 | 6.3 | 21.6 | 16.2 | | 14.8 | 0.75 | 0.69 | b |
| IDA | 50 | 21 | 21 | 6 | 6.3 | 25.2 | 14.3 | | 14.4 | 0.57 | 0.57 | b |
| IDA | 150 | 5 | 5 | 3 | 2.25 | 9 | 21.5 | 19 | | 2.39 | 2.11 | c |
| IDA | 150 | 5 | 5 | 3 | 2.25 | 9 | 21.5 | | 14 | 2.39 | 1.56 | d |
| IDA | 100 | 5 | 5 | 2 | 1 | 4 | 9.6 | 11 | | 2.39 | 2.75 | e |
| IDA dual #1 | 100 | 5 | 5 | 4.985 | 2.4925 | 9.97 | 23.8 | 16.5 | | 2.39 | 1.65 | f |
| IDA dual #2 | 100 | 5 | 5 | 4.985 | 2.4925 | 9.97 | 23.8 | 15 | | 2.39 | 1.50 | f |
| IDA dual #2 | 100 | 5 | 5 | 4.985 | 2.4925 | 9.97 | 23.8 | | 12.2 | 2.39 | 1.22 | g |
| IDA 2μm tested | 750 | 2 | 2 | 6 | 9 | 36 | 215.0 | 152 | | 5.97 | 4.22 | |
| VIDA | 600 | 1 | 5 | 2.55 | 18 | 36 | 300.9 | | | 8.36 | | |
| VIDA | 375 | 1 | 8 | 2.55 | 18 | 36 | 216.4 | | | 6.01 | | |
| VIDA | 300 | 1 | 10 | 2.55 | 18 | 36 | 184.3 | | | 5.12 | | |
| VIDA | 200 | 1 | 15 | 2.55 | 18 | 36 | 136.7 | | | 3.80 | | |
| VIDA | 150 | 1 | 20 | 2.55 | 18 | 36 | 110.1 | | | 3.06 | | |

1. Slope calculated from steady-state "collector electrode" from a recycling CV with 100μM Osmium Free Mediator run at 5mV/s
2. Slope calculated from regression through a dose response curve

[a] Note values varied from different electrode wafer ID#s. Data from wafer ID 0800 RD1. NB 33101-153CW
[b] Note values varied from different electrode wafer ID#s. Data from wafer ID 0800 RD1. NB 4920-50DN
[c] NB 33508-47 IA
[d] NB 33508-45 IA
[e] NB 33508-52 IA
[f] NB 33101-148 to 149 CW
[g] NB 33101-163 CW
[h] Electrodes varied within wafer and across wafers (best case recycling reported) NB 33101-94 to 147 CW
[i] Electrodes varied within wafer and across wafers NB 33101-137 to 139 CW
[j] Electrodes varied within wafer NB 33508 18-22 IA
[k] Electrodes varied within wafer, slopes higher when reduction occurs with top fingers, DR slope non recycling=0.6 NB 33508 24-29, 34-39 IA
[l] Kapton VIDA 0598bm4 50μM, PI2723 NB 33101 145-147 CW

*Fig. 15*

Synthesis of Osmium THC-1 Conjugate (19)

Synthesis of Tetra Carboxylic Acid Linker (53)

ELECTROCHEMICAL AFFINITY BIOSENSOR SYSTEM AND METHODS

CROSS-REFERENCE TO RELATED APPLICATION

The present application is a divisional of U.S. patent application Ser. No. 10/555,138 filed Sep. 29, 2006 which is a national stage of the International Patent Application PCT/US2004/21187 filed Jul. 1, 2004 (which was published in English), which claims the benefit of U.S. Provisional Application No. 60/484,096 filed Jul. 1, 2003, all of which are hereby incorporated by reference in their entirety.

BACKGROUND OF THE INVENTION

The present invention relates to a system, reagents, and methods for detecting analytes in fluids. More specifically, but not exclusively, the present invention is directed at electrochemical immunoassay systems, and reagents for detecting and analyzing analytes in fluid samples and methods thereof.

Electrochemical biosensors have been used in in vitro diagnostics for determining the presence and concentration of certain biologically significant analytes in biological samples such as blood, urine, and saliva. Diabetic blood glucose monitoring has been one of the most common and successful commercial applications of electrochemical biosensors. Other diagnostics biosensor applications have been developed and include lactate, cholesterol, creatinine, blood gases, and electrolytes. Both AC and DC electrochemical measurement techniques are employed including amperometry, potentiometry, coulometry, and impedance. The majority of the current biosensor technology relies on selected, free enzymes as a bio-recognition element for the analytes. Further, this technology typically can accurately measure a relatively high concentration of the analytes in the mM range. Consequently, electrochemical detection can be accomplished using a macro electrode without the use of amplification techniques.

Other analytes of interest are found in much lower concentrations compared to glucose. Such analytes include: drugs of abuse, such as, amphetamine, cocaine, phencyclidine (PCP), and tetrahydrocannabinol (THC); therapeutic agents, such as, theophylline, digoxin, digitoxin, and methotrexate; environmental pollutants, such as, PCB and atrazine; biowarfare agents, such as, anthrax, botulism, and sarin; proteins; and hormones.

Various affinity-base assay techniques that use labels have been explored to detect these analytes. The affinity-based techniques include the use of: enzyme labels, radioisotopic labels, chemilluminescent labels, fluorescent labels, and electrochemical redox labels. However, many of these techniques are labor intensive requiring many steps that are best performed in a laboratory by skilled technicians. The number and complexity of steps prohibit routine use of these techniques "in the field". Many of these tests utilize variations on the competitive Enzyme Linked Immunosorbent Assays (ELISA). Examples include atrazine assays from Strategic Diagnostics and EnviroLogix, Inc. both of which have many manual steps including a 15 minute and 1 hour incubation time respectively. Similar ELISA-based assays and other immunoassay formats will be found that can be applied to a diverse set of assay across many industries but few are capable of a rapid onsite quantitative assay. One of the most commonly available immunoassay formats used for rapid testing or point of care devices is known as lateral flow assays and utilizes immunochromatography. Most of these products are "screening assays" that provide a qualitative result (positive/negative) indicated by the presence or absence of a line. Results are often visually read and often hard to interpret when minor or partial lines are present. Most of these assays require follow-up with another method such as GC/MS or HPLC if the result is positive. There is a great need to provide a technology to these diverse industries to allow rapid affinity-based detection. Fast detection allows rapid actionable results.

The use of electrochemical redox labels, which are also referred to as electron transfer agents or electrochemical mediator labels, have been shown to provide practical and dependable results in affinity-based electrochemical assays. However, the use of electrochemical detection techniques for quantifying the redox labels and, consequently, correlating the concentration of the redox labels with the analyte concentration, has not been without problems. Electrochemical measurements are subject to many influences that affect the accuracy and sensitivity of the measurements, including those related to the proper selection of the mediator conjugate to variations in the electrode structure itself and/or matrix effects derived from variability of the samples.

U.S. Pat. No. 5,589,326 and WO 96/25514 disclose mononuclear osmium complexes comprising two bidentate ligands and one imidazole bound via its ring-nitrogen atoms to the central osmium. These osmium complexes can be used as redox mediators especially in electrochemical biosensors. Nakabayashi et al., Sensors and Actuators B 66 (2000):128-130 examined the evaluation of Os (II) complexes as mediators accessible for biosensors. Mononuclear Os (II) complexes were synthesized and the redox potentials of Os (III/II) complexes could be lowered by the use of 4,4'-dimethyl-2,2'-bipyridine, imidazole and chloride ion as ligands. US 2003/0096997 describes mononuclear transition metal complexes and there use as redox mediators. As metal atom cobalt, iron, ruthenium, osmium, or vanadium is used. Two bidentate ligands and two other ligands are bound to the central metal. Csöregl et al., Anal. Chem. 1994, 66, 3131-3138 discloses a glucose-sensing layer made by cross-linking glucose oxidase with a polymer derived of poly (vinylimidazole), made by complexing part of the imidazoles to [Os (bipyridine) $2Cl]^{+/2+}$.

Many immunoassays require a detection limit much lower than what is currently possible with the electrochemical detection on a conventional macro-electrode. Therefore, signal amplification techniques must be used for these assays to significantly improve the electrochemical detection limit.

In light of the above-described problems, there is a continuing need for advancements in the relevant field, including improved systems, methods, compositions, and reagents related to enhancing the detection analysis of various analytes including therapeutic drugs, drugs of abuse, disease state, analytes for food testing, analytes of environmental importance, and biowarfare agents. The present invention is such an advancement and provides a variety of benefits and advantages.

SUMMARY OF THE INVENTION

In one form, the present invention provides novel osmium-based electrochemical species that can be used in immunoassays. The osmium species can be coupled to a specific binding ligand to detect analytes of interest. The osmium species can include 1, 2, or 4 osmium centers that are coupled to the specific binding ligands using a variety of linking groups. The linking groups can be selected for specific types of analytes or to accommodate the different properties exhibited by the analytes. For example, the linking group can be selected to impart different degrees of hydrophilicity (or conversely hydrophobic) properties.

The novel osmium-based electrochemical species can be used to detect and analyze a variety of analytes of interest, for example, biowarfare agents, therapeutic agents, environmental pollutants, proteins, and hormones.

The osmium-based electrochemical species can be used in conjunction with different test sensors and diagnostic kits. In one form, the osmium-based electrochemical species are used in a homogenous immunoassay to detect the analytes of interest. The assay techniques according to the present invention can be used with different test sensors and meters. In particularly preferred embodiments, the assay techniques can be used to analyze samples that contain a particularly low concentration of the desired analyte. In other embodiments, the assay techniques can be used to provide reliable assay results within a very short test time—preferably less than about 10 seconds.

In one form, the present invention provides novel test sensors that include interdigitated arrays of electrodes. The electrode arrays can include first and second working electrodes, as well as counter and reference electrodes. A bipotentiostat can be used to control different voltage potentials between the various combinations of working and reference (or counter) electrodes.

In another form, the present diagnostic kits can include portable test devices that can be readily used "in the field". The portable test devices can include the test sensors, a configurable, portable meter, and, optionally, a sample collection chamber.

Further objects, features, aspects, forms, advantages, and benefits shall become apparent from the description and drawings contained herein.

BRIEF DESCRIPTION OF THE DRAWINGS

FIG. 15 provides Table 3 listing various embodiments of IDAs and VIDAs prepared and evaluated in accordance with the present invention.

DETAILED DESCRIPTION OF THE INVENTION

Figure 1:
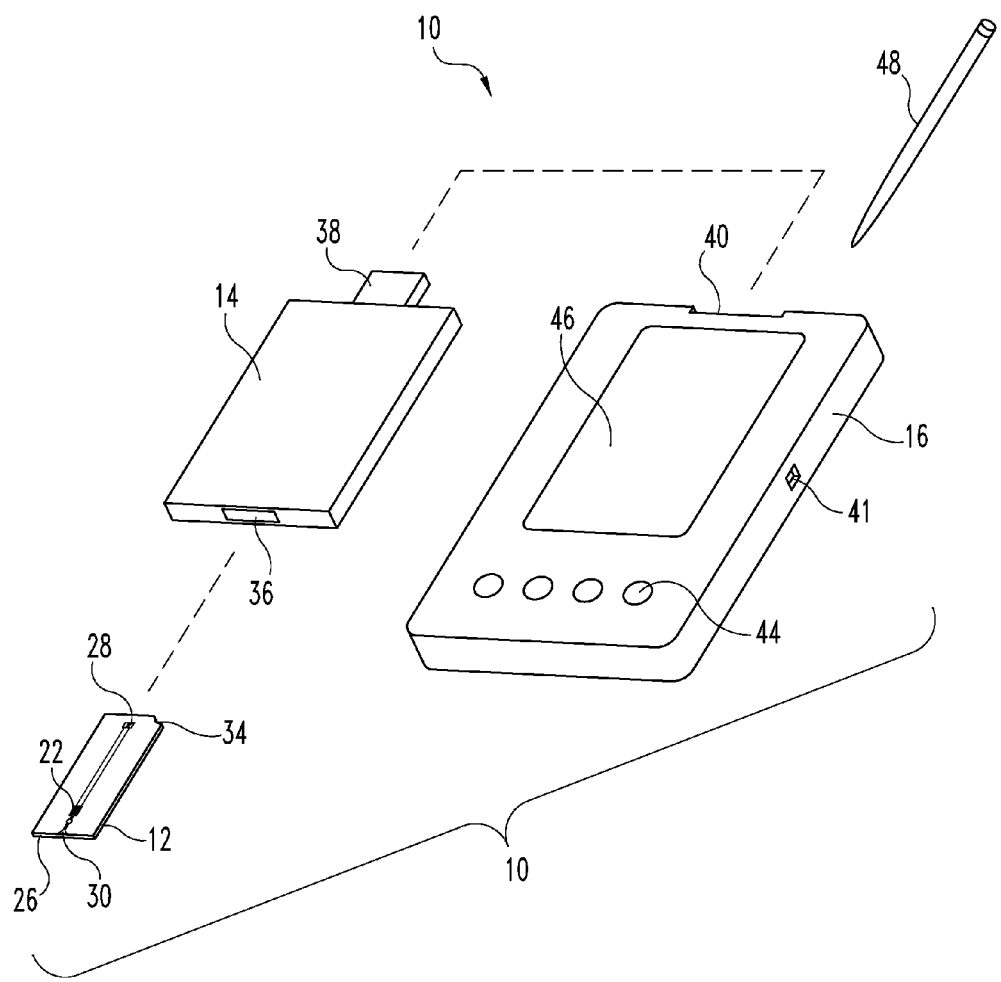
FIG. 1 is a diagrammatical representation of one embodiment of a diagnostic kit in accordance with the present invention.

The present invention provides a variety of techniques and systems for analysis of various analytes. The techniques can employ novel electrochemical mediators in conjunction with selected specific binding partners for the analytes of interest. The system can include a variety of test sensors carrying different electrode configurations and chemistries to detect or analyze the desired analytes. Additionally, a variety of test meters and configurable platforms can be employed with the test sensors to provide an accurate, reliable, and convenient-to-use assay technique.

When used herein, the following definitions define the stated term:

The term "electrode structure" refers to a combination of all active electrode areas that may have contact with the sample, the redox reversible conjugates, and/or the osmium conjugate; the electrode traces leading to the contact pads; and the contacts pads that allow an electrical contact with a meter or other instrument.

The term "active electrode area" when used in conjunction with an IDA electrode includes the electrode regions in contact with the sample including a reference electrode and at least a first and second working electrode dimensioned to allow diffusional recycling of the diffusible redox reversible conjugates in the sample when a predetermined redox-reversible species dependent cathodic and anodic potential is applied to the working electrodes.

In the case of enzyme amplification the "active electrode area" includes the electrode regions in contact with the sample including a reference electrode and at least a first working electrode.

The term "IDA electrode" refers to an Interdigitated Array electrode often drawn as a pair of comb-type electrodes but can include other shapes that bring two or more electrodes in close proximity to allow for redox recycling between the electrodes. Included in this definition are electrodes that may be spatially separated in different planes also referred to as Vertical Interdigitated Array electrodes (VIDA).

The term "working electrode" as used herein refers to an electrode where measured events (i.e., oxidation and/or reduction) take place and the resultant current flow can be measured as an indicator of analyte concentration.

The term "anodic potential" refers to the more positive potential applied to the anode, and "cathodic potential" refers to the less positive or negative potential applied to the cathode (vs. a reference electrode such as Ag/AgCl).

A "test sensor" refers to a combination of structures and reagents including all subcomponents such as plastics, spacers, and adhesives as well as the specific architectural components, such as, capillaries, measurement zones, and electrode structures. A test sensor can include the required components structures, and reagents for a single assay or it may contain the components, structures and reagents needed for multiple assays. The test sensor of this invention may also include a sample collection chamber and/or mixing chambers in addition to the measurement zone.

The term "measurement zone" is the region of the test sensor in the redox reversible conjugates which is in contact with the active electrode area and capable of being interrogated during the assay.

This region of the configurable test sensor design should remain virtually identical from assay to assay with the exception of the assay specific reagents and IDA electrode dimensions. Multiple assay designs would have multiple measurement zones except in the case of using multiple redox mediators with varied redox potentials as described in U.S. Pat. No. 6,294,062.

"Interfering substances" include any species including the analyte of interest that elevates or reduces the signal desired from the analyte. Interferents can be inherently part of the sample matrix such as ascorbic acid and uric acid that can be oxidized in blood or urine. Proteins or hydrophobic molecules such as THC can interfere with electron transfer to the electrodes by forming a passivation layer on the electrode surface reducing the expected response.

A "bipotentiostat" is the measurement engine that allows separate and independent control of the potential of two working electrodes "WE1" and "WE2" in the same electrochemical cell along with the reference and counter electrodes.

An "electrochemical label" as used herein refers to a chemical species capable of reversible oxidation and reduction in a liquid sample. Electrochemical labels can include complexes of transition metal ions, for example iron (ferrocene and ferrocene derivatives), ruthenium, and osmium. In preferred embodiments, the electrochemical label for the present invention is selected as an osmium organometallic species.

The "sample collection chamber" is the area first in contact with the specimen containing the analyte. Examples include a capillary fill zone, cuvette, cup, or other sample receiving vessel to receive the sample containing analyte. The sample collection chamber as used herein is a region that collects a volume of sample sufficient to subsequently run the desired assays. The sample collection chamber may immediately pass all or a portion of the sample to the sample receiving zone or measurement zone and run the assay, or it may hold the sample until the device is triggered at a later time to pass the sample to the appropriate zones. In selected embodiments, the sample collection, sample receiving, reaction chamber or zone, and the measurement zone are one and the same zone or region.

The "reaction chamber or zone" is the area in which the sample can interact with the reagents. This can be a simple hydrating or dissolution of a single reagent or a sequential scheme of reacting with multiple reagents. The sample receiving zone can facilitate mixing and can pass the sample to the measurement zone. In at least one embodiment, the sample receiving zone is one and the same as the measurement zone.

The term "antibody" refers to (a) any of the various classes or subclasses of immunoglobulin, e.g., IgG, IgM, derived from any of the animals conventionally used, e.g., sheep, rabbits, goats or mice; (b) monoclonal antibodies; (c) intact molecules or "fragments" of antibodies, monoclonal or polyclonal, the fragments being those which contain the binding region of the antibody, i.e., fragments; devoid of the Fc portion (e.g., Fab, Fab', $F(ab')_2$) or the so-called "half-molecule" fragments obtained by reductive cleavage of the disulfide bonds connecting the heavy chain components in the intact antibody. The preparations of such antibodies are well-known in the art.

In general, the present invention is directed to the detection and analysis of a wide variety of analytes. The analytes of interest can be found in a variety of sources, including humans, animals, plants, food, waste effluent, and ground water. The analytes may be of interest because they may be a therapeutic drug or abused substance whose in vivo concentration and activity are of interest for the well being and treatment of a patient. Other analytes of interest include analytes of environmental interest which includes monitoring water and food supplies for pesticides, herbicides, or other contaminants.

The diagnostic technique of this invention uses an electrochemical immunoassay to detect and analyze the analytes. The preferred immunoassay uses an electrochemically detectable label. In a preferred embodiment, the label is detected by measuring the current generated as the label undergoes multiple oxidation reduction cycles at or on the electrodes. Typically, the current generated by the oxidation/reduction of the detectable label is quite small and must be amplified to allow for an accurate and repeatable analysis of the desired analyte. The current can be amplified by diffusional recycling under steady state conditions and/or enzyme recycling.

The detection and analysis of the analytes can be conducted using a test kit that includes various components. Minimum components include a meter, test sensor, and sample. Preferably, a portable handheld meter configured to work with specific test sensor assays can simplify the assay method. In one embodiment, the meter is a portable handheld bipotentiostat designed for easy configurational changes to various test sensors. In another embodiment, the meter consists of a commercially available PDA or other portable computer device and a bipotentiostat module that plugs into or attaches to the device. With this configuration, software changes can be used with a variety of test sensor assays to configure the use of the same module to create assays for a diverse array of products and markets. The analysis is conducted with a small sample volume from about 4 μL to about 50 μL per assay. Sample collection volumes for the test sensor will vary depending on what is practical for the application. Blood collected from a lancet pricked finger will often be of volumes less than 15 μL but a urine sample collection device must conveniently handle larger volumes. Consequently, the test sensor configuration will vary but the underlying electrode structures and the measurement zones will in general remain the same from test sensor to test sensor except for the assay specific reagents such as the electrochemical conjugate and the affinity binding partner (antibody).

The active electrode area of the electrode structure includes at least a first working electrode, a second working electrode, a reference electrode, and a counter electrode. The first and second working electrodes are dimensioned to allow diffusional recycling with a redox reversible conjugates in the sample when predetermined anodic and cathodic potentials are simultaneously applied to the working electrodes. Electrodes dimensioned to allow diffusional recycling are typically in the form of arrays such as microdiscs, microholes, or microbands. In one embodiment, the electrodes are in the form of an interdigitated arrangement of microband electrodes with micron or submicron spacing. When the distance between two differently polarized electrodes are sufficiently close, the diffusion layers are superimposed. Redox species oxidized at one electrode diffuse to and are reduced by the neighboring electrode. This results in an amplified current signal due to the species being repeatedly oxidized and reduced.

The test sensor can contain a sample collection chamber and a sample receiving chamber for receiving the liquid sample. The sample collection chamber can include, for example, a capillary fill chamber, cuvette, cup, or other sample receiving vessel to receive the sample containing analyte. In one embodiment, the sample collection chamber and sample receiving chamber may be the same chamber. In yet another embodiment, the sample collection chamber, the sample receiving chamber, and the measurement zone may be the same chamber. Embodiments with separate sample collection chambers or zones can be designed to collect efficiently and conveniently the preferred method of sample collection for a particular test sensor assay. Some preferred sample collection methods include a capillary chamber to pull in the blood from a finger stick or a port introduction of the sample by other means including dipping into a bulk sample or via a syringe or pipette. In another embodiment, the test sensor would include a larger sample collection chamber such as a cup useful for the collection of groundwater, waste effluent, or urine. Test sensors with larger sample collection chambers are desired in various industries when it may be important to maintain additional samples and/or seal the sample with a tamper resistant seal. This provides particular advantages for samples that may have legal, evidentiary issues or for samples suspected of containing biohazard contaminants. Alternatively, the test sensor could contain only the measurement zone serving also as the sample collection and sample receiving zone. In all cases, the electrochemical immunoassay portion of the test sensor requires only a small sample sufficient to contact and dissolve with a predetermined amount of redox reversible conjugates and a specific binding partner.

The electrode structures can be supported on one or more walls of the chamber, wherein at least a portion of the electrode structure, the active electrode area, is in contacted with the liquid sample. The contact regions of the electrode structure enable the meter or measurement module to apply the respective cathodic and anodic potentials to the working electrodes to carry out the present method. The anodic and cathodic potentials are applied relative to the reference electrode—usually a Ag/AgCl ink using a bipotentiostat. The electrode structure optionally will include a counter electrode for current control. The bipotentiostat is utilized to apply a first cathodic potential to a first working electrode and a first anodic potential to a second working electrode; the first cathodic and anodic potentials correspond to those respective potentials necessary to establish current flow through the sample due to diffusional recycling of the first redox reversible conjugates. Optionally, the potential on one working electrode can be set at a first diffusible species dependent anodic potential and current flow is measured as the potential of the other working electrode is swept through a potential corresponding to the predetermined diffusible species dependent cathodic potential (or vice versa).

The cathodic and anodic potentials appropriate for each reversible redox species can be readily determined by empirical measurement such as cyclic voltammetry (CV). This technique was used to determine the redox potentials and reversibility of the electrochemical mediator and labels. In addition, a recycling CV was also used to measure the ability of an IDA electrode to recycle a known concentration of redox reversible conjugates and determine the effective amplification. A recycling CV is performed by fixing the first working electrode potential at either an oxidation or reduction potential and then scanning the second working electrode between oxidation and reduction. CVs and recycling CVs were both performed using a CHI 832A electrochemical detector from CH Instruments, Austin, Tex.

Preferred electrochemical mediators are redox reversible conjugates selected for several attributes including one or more of the following low redox potentials, fast mediation kinetics, fast electron transfer rate at the electrode surface, ease of analyte conjugation, stability, solubility, toxicity, and inhibition of the redox recycling upon pairing with the specific binding partner (antibody). Bipyridyl osmium complex conjugates as discussed in U.S. Pat. No. 6,352,824 and imidazole-osmium complex conjugates as discussed in U.S. Pat. No. 6,262,264 are both examples of mediators with appropriate properties. The mediators in the aforementioned patents generally meet the desired properties and can be viewed as a starting point in the selection of a mediator for assay development. Conjugates of mediators were prepared and evaluated accordingly as assays for various analytes of interest including amphetamine, theophylline, cocaine, PCP, morphine, THC, and methotrexate.

Although the previous class of electrochemical conjugates or labels performed well with most of the desired assays, certain electrochemical conjugates do not. As an example, the following osmium histamine linked drug conjugates, osmium THC-2 (compound 17), osmium THC-1 (compound 19) and osmium methotrexate (compound 21), all met many of the desirable electrochemical features but all suffered in terms of solubility and antibody recognition. The osmium methotrexate conjugate was not soluble in the aqueous PBST matrix and required the addition of DMF. A ratio of 30:70 DMF:PBST was used to solubilize the osmium methotrexate conjugate. To overcome these specific assay difficulties, additional conjugate structures were proposed and synthesized. A longer, more flexible and hydrophilic linker, herein called PEG-linker, was purchased as O—(N-Boc-2-aminoethyl)-O—(N-diglycolyl)-2-aminoethyl hexaethylene glycol (compound 33) from Nova Biochem. The synthesis of an osmium-PEG-amine derivative is shown as compound 36 and derived using the synthesis schemes of FIGS. 30 and 31. This compound was then used to prepare electrochemical labels for THC (compound 37) and methotrexate (compound 38) as shown in synthesis schemes of FIG. 32 and FIG. 33 respectively. Difficulties with the THC and methotrexate assays were somewhat expected due to their hydrophobic nature, lower required detection limits, and available antibodies compared to other assays developed.

In addition to the hydrophilic PEG linker, a second useful conjugate type was prepared to moderately improve the detection sensitivity. Osmium complexes with multiple redox centers were proposed. Synthetic schemes were prepared for 2 and 4 osmium redox centers per analyte binding site. It was expected that "D" the diffusion coefficient would decrease with these new conjugates due to the increase in the conjugate molecular weight. But by doubling or quadrupling the available redox sites, there was a potential for increased recycling.

The osmium-PEG-linkers for THC-1 and methotrexate achieved improved solubility in comparison with normal osmium the hydrophobic antigens. Both were able to be dissolved in a PBST matrix without the use of an organic solvent as previously used. It is also suggested that this linker may also achieve better accessibility to the antibody due to the long flexible and hydrophilic nature of the linker. The osmium-PEG-conjugates and the di-osmium conjugates performed reasonably well in electrochemical characterization including CVs and conjugate dose response curves. These new mediator conjugates perform well in many assays and offer specific improvements to overcome certain assay difficulties associated with mediators being used in the art, such as mediator conjugates of hydrophobic antigens including, for example, tetrahydrocannibinol and methotrexate antigens.

In aqueous solutions, the useable range of potentials of the first and second working electrode can be selected to be about 600 mV to −600 mV vs. Ag/AgCl reference electrode to avoid oxidation or reduction of water. Electrochemical labels with lower redox potentials are preferred to avoid interference from possible oxidizable interferents such as uric acid and ascorbic acid. U.S. Pat. No. 6,294,062 discusses that multiple mediators of differing redox potentials mixed together can be measured independently of each other on an IDA electrode if the reversible redox species are selected to be to have redox potentials differing by at least 50 mV. Additionally, multiple analytes can be measured with mediators of similar or different potentials if the different reversible redox species are separated or segregated into different measurement chamber. Measurement of steady state currents associated with a redox recycling of unbound mediator on an IDA electrode is proportionate to the concentration of analyte. The current can be measured at WE1, WE2, or both.

The present invention can be used to simultaneously measure two or more analytes in a single sample. In one preferred mode of operation, the kit includes a series of electrode sets or structures; each set of electrodes are disposed within a separate sample chamber. The liquid sample is supplied to the separate sample chambers. For example, a test sensor can include at least a second sample chamber supporting a second electrode set configured as described above for the first electrode set. Additionally, the separate sample chambers can contain different redox reversible conjugates.

The method includes detecting an analyte in a sample by measuring the concentration of an unbound electrochemical label which is correlated to the concentration of the desired analyte in the sample.

Table 1 shows possible detection ranges for analytes in comparison to blood glucose monitoring. Consequently, the diagnostic techniques should be highly sensitive. Affinity-based assay techniques can provide the sensitivity to detect these analytes.

TABLE 1

Analyte Concentrations Ranges

| Analyte | Typical Concentrations | Actionable values | Suggested Test Range |
|---|---|---|---|
| Glucose | 2-6 mM | >6 mM, <2.2 mM | 1-33 mM |
| Theophylline | 56-111 µM | >138 µM | 10-222 µM |
| Amphetamine | 220-230 nM | 3.5-7.0 µM | 1-10 µM (Cutoff 6.7 µM) |
| Morphine | 180-700 nM | 1.75-10.5 µM | 1-20 µM (Cutoff 1 or 7 µM) |
| Cocaine | 330-660 nM | >3.3 µM | 0.5-10 µM (Cutoff 1.0 µM) |
| Methotrexate (Chemotherapeutic agent) | Varies from time and amount of dose | (Post Dose) >10 µM (24 hr) >1 µM (48 hr) >0.1 µM (72 hr) | Varies over large range. Multi assay to cover specific ranges may be best approach |
| Tetrahydrocannabinol | Not Applicable | 160-640 nM | 50-1000 nM (Cutoff 160 nM) |
| Oxycodone | 48-127 nM | >320 nM | 50-1000 nM |
| Digitoxin (cardiac glycoside) | 13-39 nM | >39 nM | 2.6-85 nM |
| Digoxin (cardiac glycoside) | 1-2.6 nM | >3 nM | 0.22-6.44 nM |
| Atrazine (herbicide) | <15 nM | >15 nM | 0.5-25 nM |

Note:
Cutoff concentration: The specific concentration of drug or drug metabolite in the sample that is chosen as a limit to distinguish a positive from a negative test result. Cutoff levels are mandated for U.S. Federal Government employees but may vary for workplace testing and in specific countries

TABLE 2

| Analyte | Specific Binding Partner |
|---|---|
| Antigen (e.g., a drug) | Antibody |
| Antibody | Antigen |
| Hormone | Hormone Receptor |
| Hormone Receptor | Hormone |
| Polynucleotide | Complementary Polynucleotide Strand |
| Avidin | Biotin |
| Biotin | Avidin |
| Protein A | Immunoglobulin |
| Immunoglobulin | Protein A |
| Lectins | Specific Carbohydrates |
| Carbohydrate | Lectins |

In one form of the present invention, the binding group of the electrochemical label comprises an antigenic determinate, an epitope, or a ligand analog, typically, via one or more linker groups to form a "redox reversible conjugates" described above. The term "ligand analog" as used in the present invention includes within its meaning a chemical species capable of complexing with the same specific binding partner as the analyte being measured and can include the analyte itself. Low molecular weight species are most desirable in view of the diffusion-based electrochemical detection Recently, there have been significant advances in electrochemical affinity biosensor technology that relies on the information obtained from a complex between the analyte and a "specific binding partner". Such techniques typically employ a labeled ligand analog of a target analyte, where a ligand analog is selected so that it binds competitively with the analyte to the specific binding partner. The extent of binding of the labeled ligand analog to the specific binding partner can be measured and correlated with the presence and/or concentration of the analyte in the sample. Examples of analytes and their specific binding partners are listed in Table 2 below.

technique utilized in carrying out the present method. Consequently, it is desirable that the redox reversible conjugate having a molecular weight of less than about 50,000 Daltons, more preferably less than about 10,000 Daltons. Most preferably, the molecular weight of the redox reversible conjugate is between about 500 and about 5,000 Daltons.

Examples of ligand analogs for use in the present invention include, but are not restricted to: peptide hormones (e.g., thyroid stimulating hormone (TSH), luteinizing hormone (LH), follicle stimulating hormone (FSH), insulin and prolactin) or non-peptide hormones (e.g., steroid hormones such as cortisol, estradiol, progesterone, and testosterone) or thyroid hormones such as thyroxine (T4) and triiodothyronine), proteins (e.g., human chorionic gonadotropin (hCG), carcino-embryonic antigen (CEA) and alphafetoprotein (AFP), drugs (both drugs for therapeutic use, drugs of abuse and/or regulated drugs), such as amphetamine, sugars, toxins or vitamins and biowarfare agents. Specific examples of ligand analogs which can be included as ligand analogs in accordance with the present invention include, but are not restricted to: cocaine, amphetamine, morphine, barbiturate, theophylline, phenylcyclidine (PCP), tetrahydrocannabinol (THC), methotrexate, benzodiazepine, phenyloin, carbamazepine, phenobarbital, gentamicin, amikacin, vancomycin, tobramycin, procainamide, lidocaine, quinidine, valproic acid, digoxin, digitoxin, tricyclic antidepressants (TCA), such as: buprenorphine, amitrptyline, desipramine, imipramine, nortriptyline, doxepin, immunosuppressants. Warfare or biowarfare agents that can be included with the present invention include, but are not restricted to: racin, anthrax (B. anthracis.), small pox, botox, and botulinum toxin.

FIG. 1 is a diagrammatical illustration of a system or a diagnostic kit 10 for detecting and/or analyzing one or more analytes in a sample fluid. Kit 10 includes a test sensor 12, a measurement module 14, and a handheld or portable controller 16.

In the illustrated embodiment, test sensor 12 includes an electrode structure 22. The electrodes in the electrode structure can be parallel to each other and supported on the same wall of the detection chamber or opposing each other with one electrode supported on one wall and another electrode supported on an adjacent wall or an opposite wall of the detection chamber. In a preferred embodiment, the electrode set includes a multi-array electrode such as an interdigitated array (IDA). Each electrode in the IDA includes a plurality of "fingers" which interdigitate with the "fingers" of the other electrode. The individual electrodes in the IDAs can be either parallel to each other or opposing each other. In other embodiments, the multi-array electrode can be fabricated as a vertical interdigitated array electrode described more fully below.

In preferred embodiments, test sensor 12 provides a sequential analysis of one or more analytes in a sample solution. Preferably, the reagents supplied onto test sensor 12 are provided in dry form with the fluid in the test sample providing the medium for conducting the analysis.

Test sensor 12 can be provided as either a flexible strip or a rigid strip discussed more fully below. The rigid test sensor can be fabricated, for example, using integrated circuit technology on a silicon wafer.

Test sensor 12 includes a first end 26 and an opposite, second end 28. A sample port 30 is positioned on test sensor 12 adjacent first end 26. In alternative embodiments, a sample port 30 can be positioned on a side of test sensor 12.

Second end 28 includes a plurality of contact pads. In addition, second end 28 can include a physical "key" such as a projection, protuberance or notch 34 to require a unique orientation of test sensor 12 for the connection or insertion of second end 28 into measurement module 14. In other embodiments, second end 28 can include one or more electrical connections to ensure the correct orientation and/or insertion of the test sensor into the measurement module 14. Additionally, one or more of the electrical connections and contacts can be used to identify the specific test sensor either by production lot for quality control analysis and/or identification of the type of test sensor, which analyte(s) the test sensor is configured to analyze and/or the analyte(s) predicted concentration range.

Measurement module 14 includes a connection or receptacle 36 for receiving second end 28. Receptacle 36 includes a corresponding "lock" for the physical key, if present, and a corresponding number of electrical contacts to mate with the electrical or magnetic connectors and contacts on test sensor 12.

In one embodiment, measurement module 14 includes at least one bipotentiostat. The bipotentiostat can be configured to simultaneously apply and control the voltage of two different electrode sets on test sensor 12. In other embodiments, measurement module 14 can include two or more bipotentiostats, each bipotentiostat configured to apply and control the voltage of two different electrode sets. Consequently, the measurement module can include one or more programmable bipotentiostat(s) to control potentials on the electrode structures in contact with the sample. In still yet other embodiments, the bipotentiostat can be included either in a desktop or hand-held meter 16 described below.

Additionally, measurement module 14 can include hardware, software, or firmware providing instructions to run one or more analyses and identification of one or more selected analytes in a test sample.

Measurement module 14 also includes a connector 38 to operably couple measurement module 14 with portable controller 16. In the illustrated embodiment, measurement module 14 includes a connector 38, which is configured to be received within a receptacle 40 on portable controller 16.

Portable controller 16 can be provided in a wide variety of hand-held electronic devices. In one preferred embodiment, portable controller 16 is provided as one of a wide variety of Portable Digital Assistants (PDA), which are commercially available. In other embodiments, portable controller 16 can be provided as a portable (preferably dedicated) computer or CPU. Portable controller 16 includes a visual output screen 46 and can, but is not required to include, one or more input devices 44, buttons, switches, and the like. In addition, as is common with a wide variety of commercially-available PDAs, data input/output screen 46 can also allow input via a stylus 48.

In use, when measurement module 14 is operably connected to portable controller 16, a software program resident on measurement module 14 can be automatically uploaded to portable controller 16. The uploaded program begins running on portable controller 16, prompting users to input specific information and/or providing instructions to the users to run specified tests. In addition, the software can include one or more instructions or the capability for determining values for steady state current, storing these values, calculating analyte concentrations, data management, quality control, calibration, test sensor identification (production lot, analyte concentration range, and/or type of analyte), and connectivity to a centralized laboratory information system.

In one embodiment, controller 16 begins with a Drug Monitoring System screen with date and time. The next screen prompts the user to enter the operator identification. Thus, if desired, controller 16 could be set up so that only specified users with proper training could get access to run an assay. The operator identification can be entered as numbers or an alphanumeric code. The next command or next screen can be a main menu screen that allows selection of a specific Drug Test, Control Test, or Review Results, for example. Selecting "Drug Test" prompts the user to enter a patient identification or name. The next screen then allows the user to select the proper test(s) or conditions. Additionally controller 16 (or measurement module 14) can include recognition software or hardware to verify and identify the specific test sensor that is or should be used with either the patient or the selected test or test conditions. After selection of a specific test, the user is instructed to insert the test sensor or test sensors into the measurement module 14. Controller 16 can block a test if the tests selected and/or if the inserted test sensor is not compatible or recognized. If the test sensor is compatible or recognized, then the controller is ready for the sample to be supplied to the test sensor. Once the sample is applied, the test begins. The controller can signal the user when the test is completed and report the results at the end of the assay period. In preferred embodiments, the controller has the capability to report quantitative or qualitative values depending on the desired requirements for an assay. Results are saved in the instrument and a report can be printed via the IR port 41 of the instrument directly to a printer equipped to receive an IR signal. The data can also be downloaded via an IR port, hardwire connection and/or with a manual "hotsync" of the controller placed in a cradle.

Figure 2:
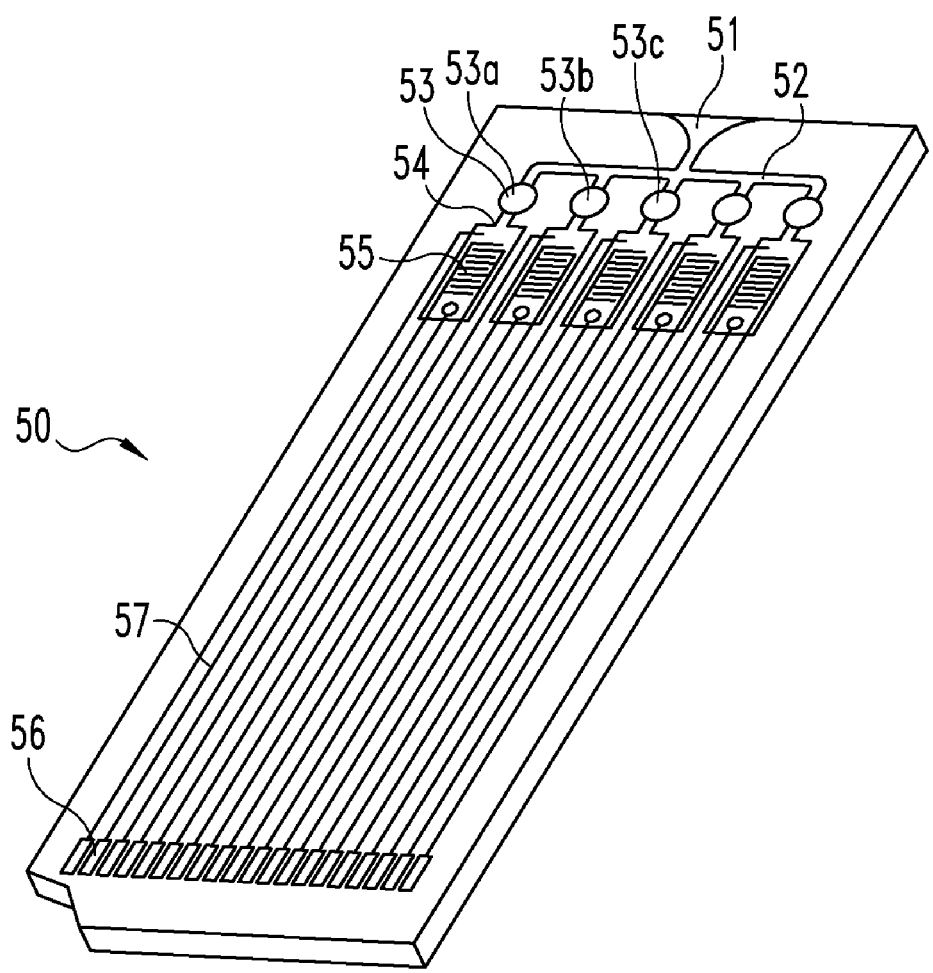
FIG. 2 is a perspective view of one embodiment of a test sensor having a planar array of electrodes useful for detecting and analyzing for a plurality of analytes of interest in accordance with the present invention.

FIG. 2 is a perspective view of one embodiment of a test sensor 50 for use with the present invention. Test sensor 50 is illustrated to analyze a plurality of different analytes in a single sample fluid. Test sensor 50 includes a single dosing or sample port 51 and a plurality of channels 52 leading to a plurality of reagent chambers 53. Different reagents, buffers, labeled ligand analogs, and the like are disposed in each different reagent chamber 53a, 53b, 53c . . . . It will be understood that two or more different reagent chambers, each containing a different reagent or sets of reagents, can be used for different assay methods, e.g., sequential binding or displacement binding technique. A channel 54 leads from the reagent chamber 53 to measurement zone 55. Again, a separate channel leads from each separate reagent chamber to a different detection chamber.

In the illustrated embodiment, soluble reagents, buffers, and/or labeled ligand analogs are dried but not immobilized onto a substrate or matrix. A portion of the fluid sample is drawn into sample port 51 typically by capillary action. The sample fluid progresses through channel 52 to each of the reagent chambers, where the analytes in the sample bind to a binding partner, a labeled binding partner in a direct binding analysis or conversely the analyte can displace a bound partner from an analyte, a derivative thereof, or labeled ligand analog. The sample fluid with the reaction product, from the reagent chamber, progresses to the detection chamber, where the resulting labeled ligand analog conjugate can be electrochemically detected.

In other embodiments, one or more of the reagents, buffers, and labeled ligands can be immobilized either in the reagent chamber of in another portion of the fluid circuit on the test sensor; for example, in the detection chamber.

Figure 3:
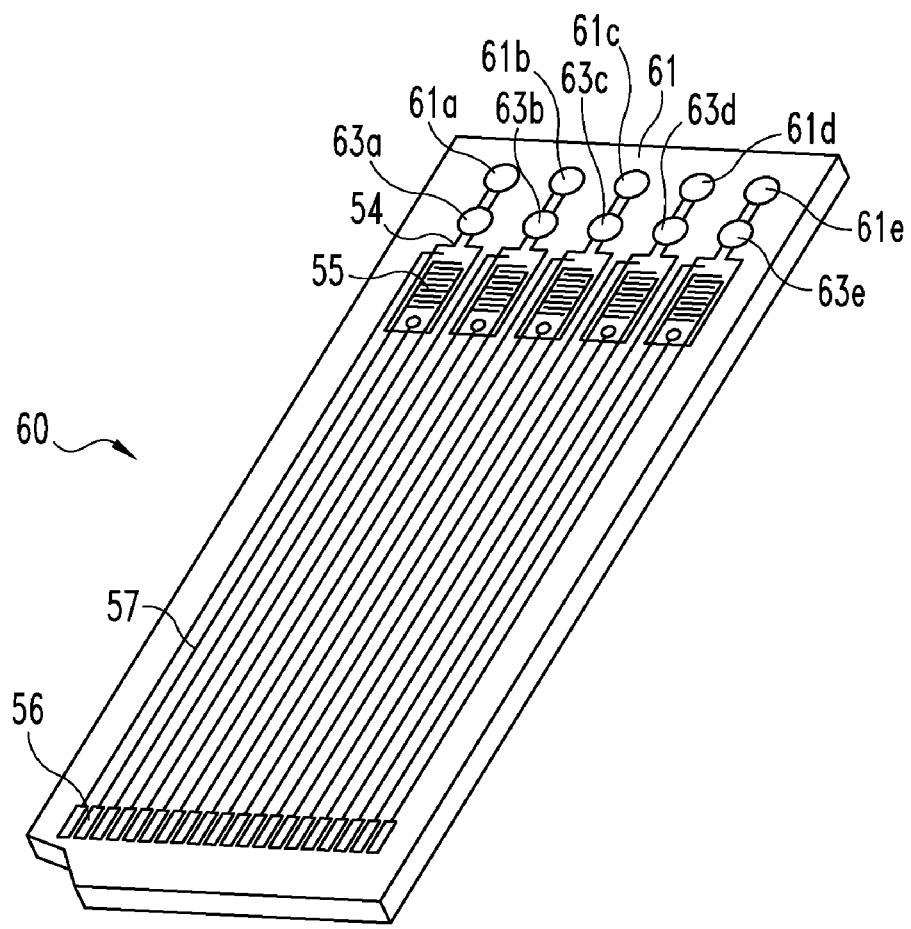
FIG. 3 is a perspective view of another embodiment of a test sensor having a planar array of electrodes useful for detecting and analyzing a plurality of analytes of interest with a plurality of sample ports in accordance with the present invention.

FIG. 3 is perspective view of an alternative embodiment of a test sensor 60 configured similar to test sensor 50, consequently the same reference numbers are used for similar structures. Test sensor 60 differs from sensor 50 by including separate dosing ports 61a, 61b, 61c, . . . one for each of the separate reagent chambers 63a, 63b, 63c. In this embodiment, different samples can be applied to the different ports 61a, 61b, 61c . . . and each of the different samples can be analyzed using the same reagents and conditions. Alternatively, the same bulk sample can be introduced to the different ports 61a, 61b, 61c . . . and the different reagent chambers 63a, 63b, and 63c can include different reagents to perform different analysis of the bulk sample.

Figure 4:
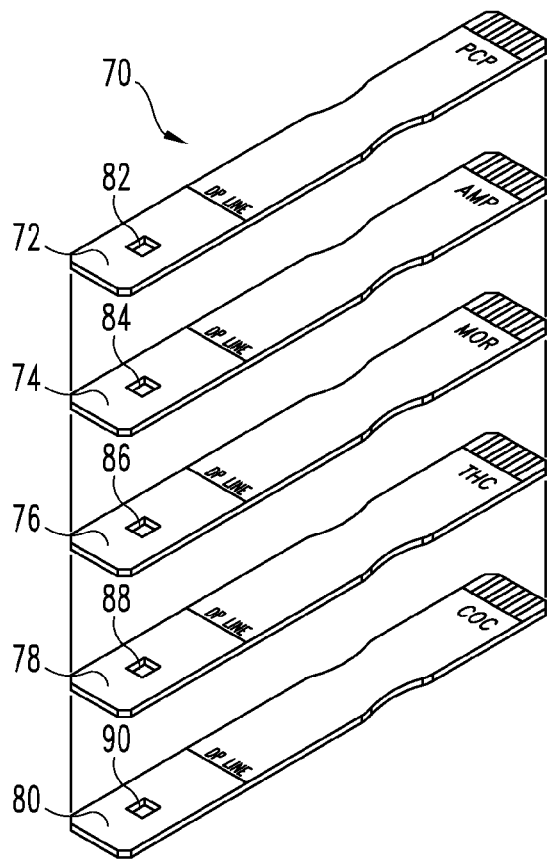
FIG. 4 is an exploded view of yet another embodiment of a test sensor useful for detecting and analyzing a plurality of analytes.
Figure 5:
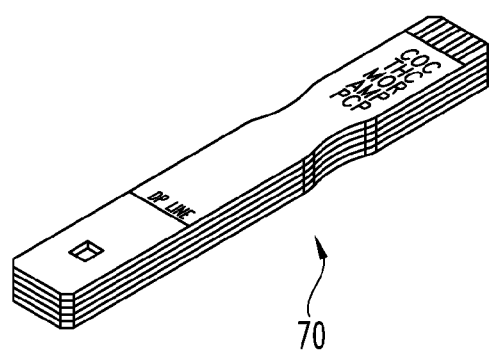
FIG. 5 is a perspective view of the test sensor of FIG. 4.

FIG. 4 is an exploded view of yet another embodiment of a test sensor 70 for use with the present invention; FIG. 5 is a perspective view of test sensor 70. Test sensor 70, similar to test sensors 50 and 60, includes a plurality of reagent chambers and electrode structures. Test sensor 70 includes a plurality of support strips 72, 74, 76, 78, and 80 laminated on top of each other. In the illustrated embodiment, each support includes a sample port, reaction chamber, measurement zone and an electrode structure. In one form, each of support strips 72, 74, 76, 78, and 80 includes a sample port 82, 84, 86, 88, and 90, respectively, that allow the sample to be introduced into a single sample port, for example, port 82. The introduced sample will flow and dose each assay of test sensor 70. Except for the sample ports, each support strip 72, 74, 76, 78, and 80 is separated from the adjacent test sensor by a layer that is impervious to the sample and reagents. In addition, each of the reaction chambers of the sensor can include the same or different reagents.

In use a sample is introduced into a single port such as port 82, where the sample flows to the remaining sample ports. The sample then flows to a reaction chamber and then to a measurement zone, where resulting species are interrogated. Test sensor 70 can be inserted into a meter that is configured to receive a laminated test sensor with electrode pads vertically spaced apart to provide a visual display of the results of the test(s).

Figure 6:
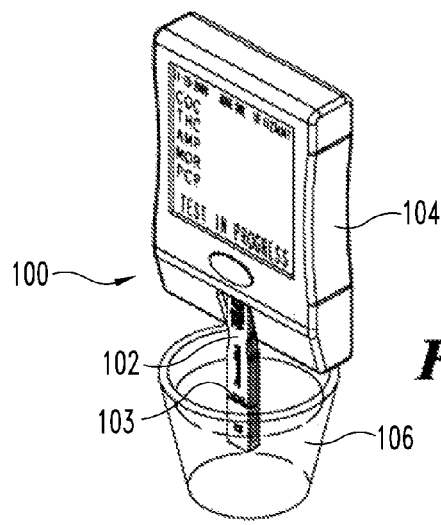
FIG. 6 is a test sensor configured for multi-analyte testing that can be dipped into the sample.

FIG. 6 illustrates one embodiment of a diagnostic kit 100 that includes a test sensor 102 and a meter 104. Test sensor 102 is inserted into the meter followed by dipping into the sample to the "dip line" 103. Test sensor 102 can be any of the test sensors described above.

Figure 7:
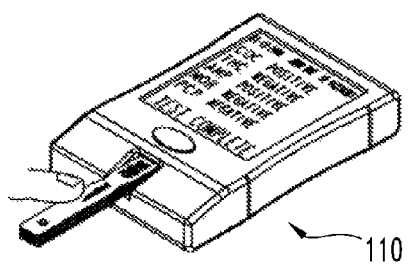
FIG. 7 is a perspective view of a test sensor and meter configured for single assay testing that can be dosed with blood from a finger pricked with a lancet.

FIG. 7 illustrates another embodiment of a diagnostic kit 110 configured for multi-analyte testing that can be dosed with a single sample, such as, with blood from a finger pricked with a lancet. The single sample can be analyzed for the presence and/or amount of many different analytes.

Figure 8:
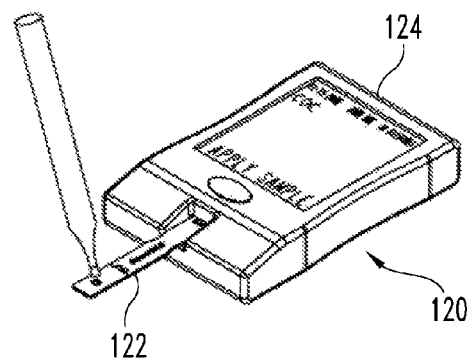
FIG. 8 shows a perspective view of a test sensor and meter configured for a single assay that can be dosed with a pipette.

FIG. 8 illustrates a diagnostic kit 120 with a test sensor 122 and meter 124 configured for single assay that can be dosed with a pipette.

Figure 9:
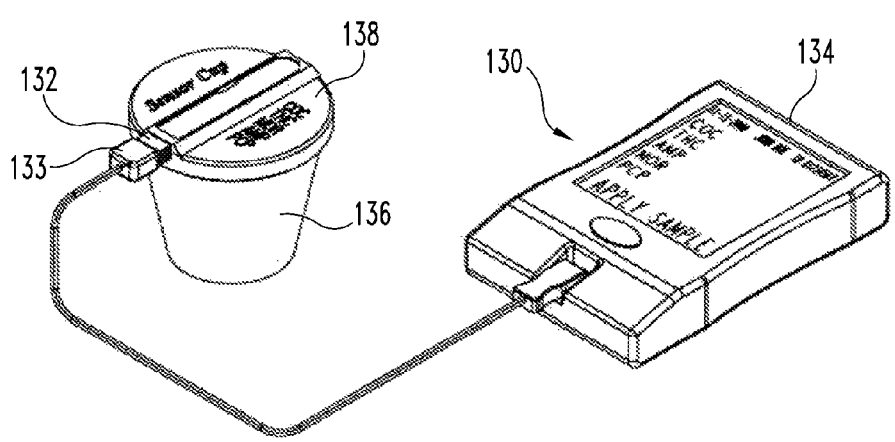
FIG. 9 shows a perspective view of a meter and test sensor configured for multi-analyte testing which includes the assay attached to a sample collection chamber.

FIG. 9 illustrates a diagnostic kit 130 that includes a test sensor 132 and meter 134 configured for multi-analyte testing. Test sensor 132 is fixedly mounted on a wall of a sample collection chamber 136. Connector 133 makes electrical connection to the contacts of test sensor 132. In the illustrated embodiment, the test sensor 132 is attached to the lid 138 of a cup. This embodiment provides particular advantages by allowing the collection of a sample. The collection chamber can then be sealed and stored or preserved as desired. Further, connection of connector 133 opens a seal between the sample application port and the collection chamber. The sample can be tested immediately upon collection or at a later time. In other embodiments, a test sensor can be mounted in or on another wall of the collection chamber 136. In other embodiments the test sensor 132 is removably mounted to the collection chamber 136.

Figure 10:
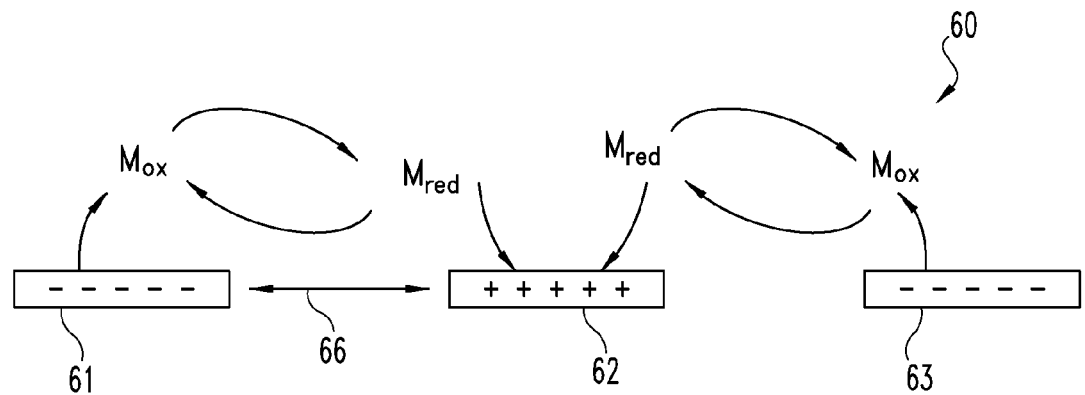
FIG. 10 is a partial cross-sectional view a pair of electrodes illustrating the conditions of steady-state current limited by diffusion of a reversible mediator (M) which is alternatively oxidized and reduced on the interdigitated electrode fingers.

FIG. 10 is a partial cross-sectional view of a microelectrode array 160 according to the present invention illustrating the conditions of steady-state current. The partial microelectrode array 160 includes two cathodes or reducing electrodes 161 and 163 and an anode or oxidation electrode 162. The mediator, M, is alternatively reduced at the cathode electrode 161 (or 163) and oxidized at the anode electrode 162. The gap between cathode electrode 161 and anode electrode 162 represented by reference line 166 can be selected to maintain a steady state current and, consequently, allow for signal amplification as discussed more fully below. As noted above, the electrode structure includes a reference electrode and at least first and second working electrodes dimensioned to allow diffusional recycling of the redox reversible conjugate in the sample when a predetermined potential is applied to the working electrodes. Smaller dimensions of finger widths W and gaps $W_g$ increase the redox recycling, but increasing the length and number of electrode pairs is also desirable for effective current amplification. The gap represented by reference line 166 can be selected as desired considering the analyte of interest and its concentration or predicted concentration in the sample. Typically the gap between adjacent electrodes is selected to be less than about 25 µm, preferably less than about 10 µm, more preferably less than about 2 µm. In cases where very low sensitivities are needed, submicron gaps are desired.

Figure 11:
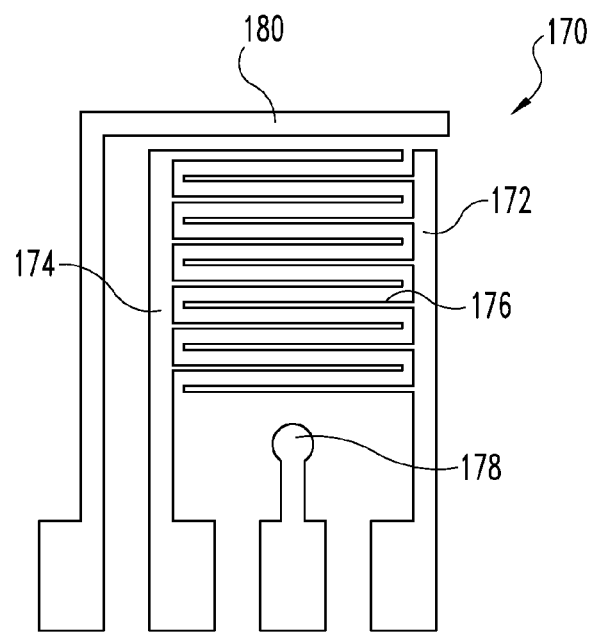
FIG. 11 is an enlarged plan view of a planar interdigitated array (IDA) electrode set suitable for measuring redox cycling of reversible mediators in accordance with the present invention.

FIG. 11 is a plan view of one embodiment of an Interdigitated Array (IDA) 170. IDA 170 is illustrated as a planar electrode structure suitable for measuring redox recycling with a bipotentiostat in accordance with this invention. IDA 170 includes two working electrodes 172 and 174 (as drawn) defining six pairs of electrode fingers 176. Also included in IDA 170 are a reference electrode 178 and counter electrode 180. The gap between two adjacent fingers represented by 166 of FIG. 10 and the total number of fingers can be selected for IDA 170 as desired for a particular analyte of application. In preferred embodiments, it is desirable to produce IDAs with more electrode pairs than shown in IDA 170. For example, in order to achieve the proper amplification it is most desirable to have at least 25 pairs of electrodes, more preferably at least 50 pairs of electrodes or 750 electrode pairs, and even greater than 1000 pairs of electrodes. Amplification increases with decreasing the width and gap and increasing the length and number of finger pairs. Each of the electrode structures in IDA 170 are dimensioned to allow diffusional recycling of a diffusible redox reversible mediator in the sample when the electrodes 172 and 174 are poised at predetermined anodic (oxidation) and cathodic (reduction) potentials.

Microelectrode arrays can be fabricated using a variety of technologies including but not limited to photolithography, electron beam lithography, ion beam milling, nanoimprint lithography, and laser ablation techniques described in WO 03/044511, which is incorporated by reference. Interdigitated electrode array (IDA) can be deposited on a variety of insulating substrates not limited to: glass, silicon, Upilex, Kapton, Kaladex, Melinex, or other polymeric substrates.

Improvements in meter construction and design for biosensor systems are described in U.S. Pat. Nos. 4,999,632; 5,243,516; 5,366,609; 5,120,420; 5,141,868; 5,192,415; 5,264,103; 5,352,351; 5,405,511; 5,437,999; 5,438,271; and 5,575,895, the disclosures of which are hereby incorporated by reference.

The size (or surface area) and number of electrode pairs can be selected depending upon the analyte(s), their concentration, and the sample medium among other factors. In addition, the present invention provides an empirical construct for selecting the size and/or number of pairs of electrode fingers for a given set of conditions. The construct is described more fully below.

In yet other embodiments, the components of array 170 can be sized to provide a macro electrode array. The electrode dimensions and the gap between the electrodes for the macro array can vary significantly and may be limited only by the size of the test sensor and the available sample volume.

Vertical IDA Electrodes

Figure 12:
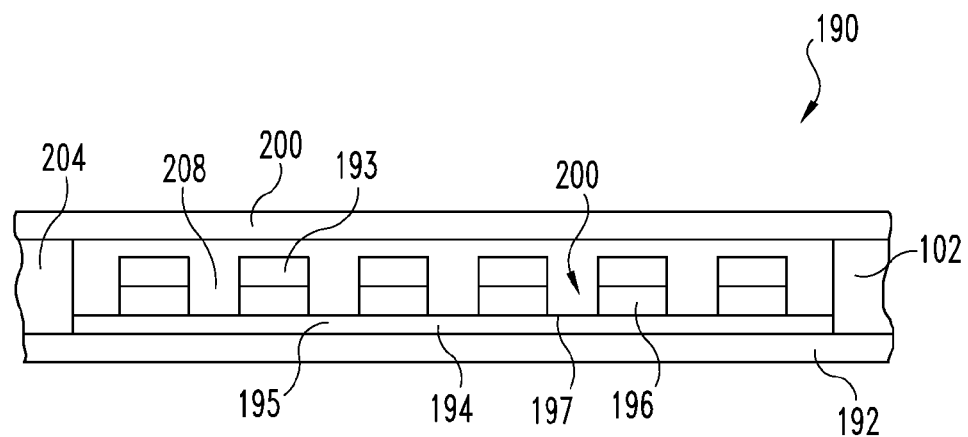
FIG. 12 is a partial cross-sectional of a vertical interdigitated array electrode set for reversible mediator measurement in accordance with the present invention.
Figure 13:
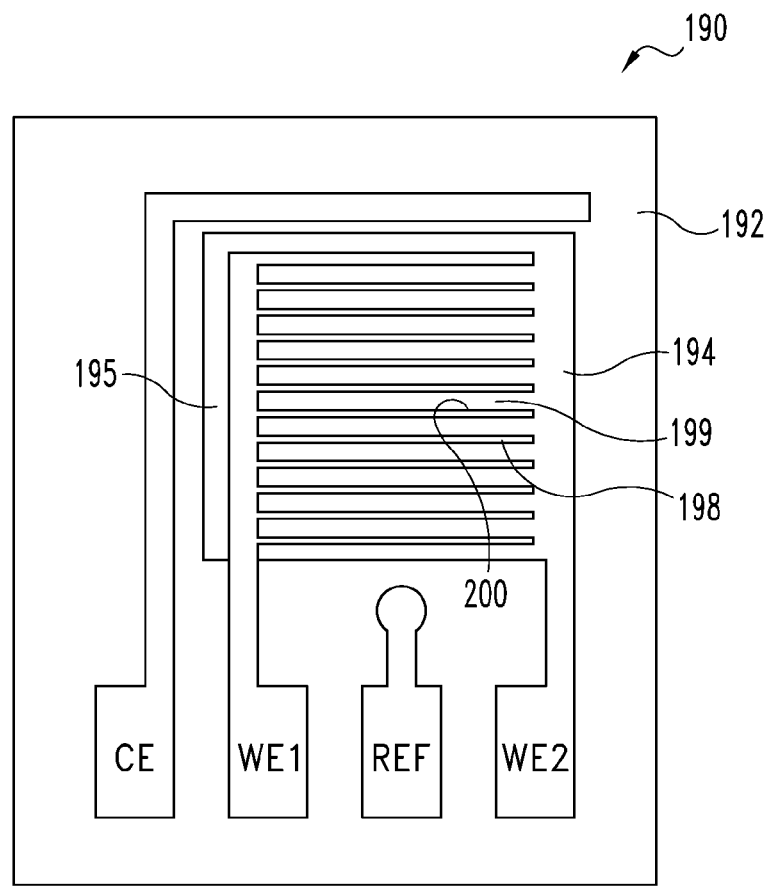
FIG. 13 is an enlarged plan view of a vertical interdigitated array electrode of FIG. 12.

FIG. 12 is a side or edge view of a vertical interdigitated array (VIDA) 190 in accordance with the present invention. FIG. 13 is a top plan view of one embodiment of array 190. Array 190 includes a base or insulative substrate 192 onto which is deposited an electrically first conductive material as conductive layer 194 to provide a first electrode 195. A dielectric insulative layer 196 is deposited on conductive layer 194 and substrate 192. A second conductive material 193 is deposited on top of the dielectric layer 196. A second dielectric layer (not shown) is then deposited and patterned onto the second conductive material 193 to define a plurality of non-conductive fingers (not shown). The exposed second conductive material is removed followed by the removal of the exposed dielectric layer. This leaves behind the second set of electrode fingers 193 deposited on top of the non-conductive finger 196 and patterned to define a plurality of electrode fingers 198.

The electrode gap of a VIDA is defined by the thickness of the dielectric insulator 196 sandwiched between the conductive layers, thus micron to submicron gaps can be produced using standard techniques that are not capable of submicron resolution. This can be achieved because the VIDA finger gap or feature size is not dependent upon the limits of the patterning techniques but is rather a function of how thin (or thick) the dielectric insulator that can be applied.

In one embodiment, the gap is selected to be less than about 1 µm. In other embodiments, the desired gap width is selected to be between 1 µm and 3 µM.

Sidewalls 202 and 204 and an upper plate or roof 206 can be fabricated over the vertical electrode array to define a detection chamber 208. The total volume of detection chamber 208 can be selected as desired and only limited by the desired size of the test sensor and the number of detection chambers formed on the strip.

The VIDA 190 provides additional advantages over those provided by the IDAs described above, including a higher density of electrode pairs per unit surface area. Consequently, smaller chambers can be fabricated that contain the same number of electrode pairs, each electrode having the same surface area as the planar IDA. Furthermore, a test sensor can include a larger number of the VIDA as a test sensor that includes only IDAs, again where the surface area of the two test sensors are the same and the chambers each contain the same number and sized electrode pairs. This can provide important improvements for test sensors, which are configured to simultaneously detect/analyze a number of different analytes.

In FIG. 12 illustrating a VIDA electrode, the dielectric layer 196 is free of holes in the regions between the two working electrodes. Typical VIDA designs involve the fabrication of a metal-dielectric-metal on a rigid or flexible substrate. The integrity of the dielectric layer is critical for the electrochemical function of the device. Breakdown of the inner dielectric will lead to electrical shorts and a nonfunctional device. Insulators can be deposited by various processes including sputtering and spin coated dielectrics. A dry etching technique can be used to remove the insulator layer in the desired regions down to the first conductive layer. The process of making VIDA electrodes is not limited the aforementioned procedure that was included only as an example.

Cell Constants

Solution resistivity is an intrinsic property of a solution determined by the combined concentrations and mobilities of all dissolved ions in a system. This resistivity ($\rho$) in Ohm×cm of a sample will be influenced the sample matrix and reagents that mix the sample including electrochemical labels, buffers, salts, and antibody to name a few examples.

When an electric field is applied between two electrodes in the cell, ions move until the double-layer at the electrode interfaces charges sufficiently to oppose and eventually cancel the applied field. The double-layer charging behaves like a capacitor in series with the solution resistance. The measured solution resistance will have a constant additional series resistance due to contact resistance and intrinsic electrode material resistance. High frequency resistance measured in an electrochemical cell is proportional to the intrinsic solution resistivity p and the proportionality constant is called the "cell constant". High frequency may be defined as a range of frequencies where the electrochemical cell's reactive (capacitive) properties may be safely ignored.

The cell constant is an important factor in the sensitivity of the cell to changes in solution resistivity, and varies widely with electrode configuration. The geometry of interest to this invention is an interdigitated array (IDA). Here, a number of coplanar anode and cathode pairs are repeatedly alternately interlaced or interdigitated to form a larger interdigitated array electrode. For an interdigitated array, the high frequency resistance is related to the solution's resistivity by Equation 1 below.

$$R = \frac{\rho}{mbG} \quad (1)$$

The cell constant for an IDA is therefore defined by Equation 2, where m is the number of microband electrode pairs of the IDA, b is the length of the bands in cm, and G is a dimensionless function of the electrode geometry finger width (W) and gap ($W_g$). G can be approximated as per the expression defined by Equation 3. The cell constant is a useful parameter of an electrode configuration that can be both calculated and measured. The cell constant of an IDA electrochemical cell depends on its architecture, especially the electrode geometry, although in some cases the top boundary of the cell (capillary height) can also play a role. Estimation of the cell constant for an IDA is derived from the equations and work of Aoki and others, but is only a function of the number of IDA electrode pairs and their dimensions. Therefore, the cell constant is a single value that can be used to compare various electrode geometries. Electrodes with the same cell constants will have similar characteristics in the application of electrodes of this invention.

$$\text{Cell } Const. = \frac{1}{mbG} \quad (2)$$

G may be estimated for an IDA from the approximation Equation 3 from Aoki.

$$G = \left(\frac{2}{\pi}\ln\left(2.55\left(1 + \frac{W}{W_g}\right)\right) - 0.19\left(\frac{W_g}{W + W_g}\right)^2\right) \quad (3)$$

where Wg is the width of the gap between adjacent working and counter-electrode bands and W is the width of each (electrode finger) microband. The model approximation assumes no array-edge effects, meaning the electrochemical cell, containing the array and electrolyte, is large enough so as not to distort electric field lines at the cell boundaries (i.e., IDA must have enough fingers to prevent the lack of a neighbor for the first and last finger from significantly altering the current). The model also assumes that the microband anode and cathode electrode fingers are the same width. As $W_g/(W+W_g)$ varies from 0.1 to 0.9, G varies from about 2.5 to about 0.5. When $W=W_g$, $W_g/(W+W_g)=0.5$ and G is about 1.

Many articles have appeared in the literature from Koichi Aoki and others to better understand, model and predict responses at interdigitated array electrodes. The following publications are a sample of many of the discussions and mathematical computations that have been published in the field: "Theory of chronoamperometric curves at microband electrodes", J. Electroanal. Chem., 225 (1987) 19-32; "Derivation of an approximate equation for chronoamperometric curves at microband electrodes and its experimental verification", J. Electroanal. Chem. 230 (1987) 61-67; "Quantitative analysis of reversible diffusion-controlled currents of redox soluble species at interdigitated array electrodes under steady-state conditions", J. Electroanal. Chem., 256 (1988) 269-282; "Time-dependence of diffusion-controlled currents of a soluble redox couple at interdigitated microarray" J. Electroanal. Chem., (1989) 11-20; and "Approximate models of interdigitated array electrodes for evaluating steady-state currents", J. Electroanal. Chem. 284 (1990) 35-42.

Equation 4 was also derived by the aforementioned literature and is used to evaluate reversible diffusion-controlled currents of redox soluble mediators on IDA electrodes under steady-state conditions. This equation was used to predict the slope for the IDA and VIDA electrodes of FIG. 15. In this equation, m is the number of microband electrode pairs of the IDA, b is the length of the band in cm, n is the number of electrons involved in the redox reaction, F is Faraday's constant [9.65E+04C/equiv], c is the bulk concentration of the redox molecule, D the diffusion constant of the redox molecule [For osmium free mediator, 5E-06 cm²/sec.], W is the width of the microband electrodes (anode or cathode) in cm where $W_a=W_c$, and Wg is the gap between respective anode and cathode electrodes.

$$|I| = mbnFcD\left(\frac{2}{\pi}\ln\left(2.55\left(1 + \frac{W}{W_g}\right)\right) - 0.19\left(\frac{W_g}{W + W_g}\right)^2\right) \quad (4)$$

One will note that there is a relationship between this equation to predict steady-state current, G, and the cell constant. The expression for the steady-state current can be rewritten as |I|=mbnFcDG. Rearrangement of the expression leads to the following relationship with cell constant (Equation 5 below). This implies that the steady state DC current is inversely proportional to an IDA electrode's cell constant. Smaller cell constants should provide a proportionately higher steady state DC current for a given concentration and diffusion coefficient. Smaller cell constants also produce faster transitions to steady state DC conditions.

$$\text{Cell } Const. = \frac{1}{mbG} = \frac{nFcD}{|I|} \quad (5)$$

Equation 4 for the steady state current may be normalized to a unit area by dividing the predicted current by the IDA electrode area of interdigitation (Area=2(W+$W_g$)mb100). Equation 6 shows the equation used to calculate normalized predicted slope in FIG. 15. The current is multiplied by $10^9$ to convert to nA and the area is multiplied by 100 to convert from cm² to mm².

$$\frac{I}{\text{Area}} = \frac{mbnFDc10^9}{2(W + W_g)mb100}\left(\frac{2}{\pi}\ln\left(2.55\left(1 + \frac{W}{W_g}\right)\right) - 0.19\left(\frac{W_g}{W + W_g}\right)^2\right) \quad (6)$$

FIG. 15 provides Table 3 listing of various embodiments of IDAs and VIDAs prepared. The electrode geometry for each electrode is evaluated. Equations 4 and 6 discussed above were used to model the specific electrodes in terms of predicted and normalized predicted slope. In addition, experimental values are shown from recycling CVs and amperometric bipotentiostat dose response curves performed with either a CHI 802A or CHI 832A bipotentiostat from CHI Instruments, Austin, Tex. Table 4 shows the cell constant for four of these electrodes, but using Equation 2 the cell constant for each electrode shown in FIG. 15 can be calculated including the VIDA electrodes.

Figure 16:
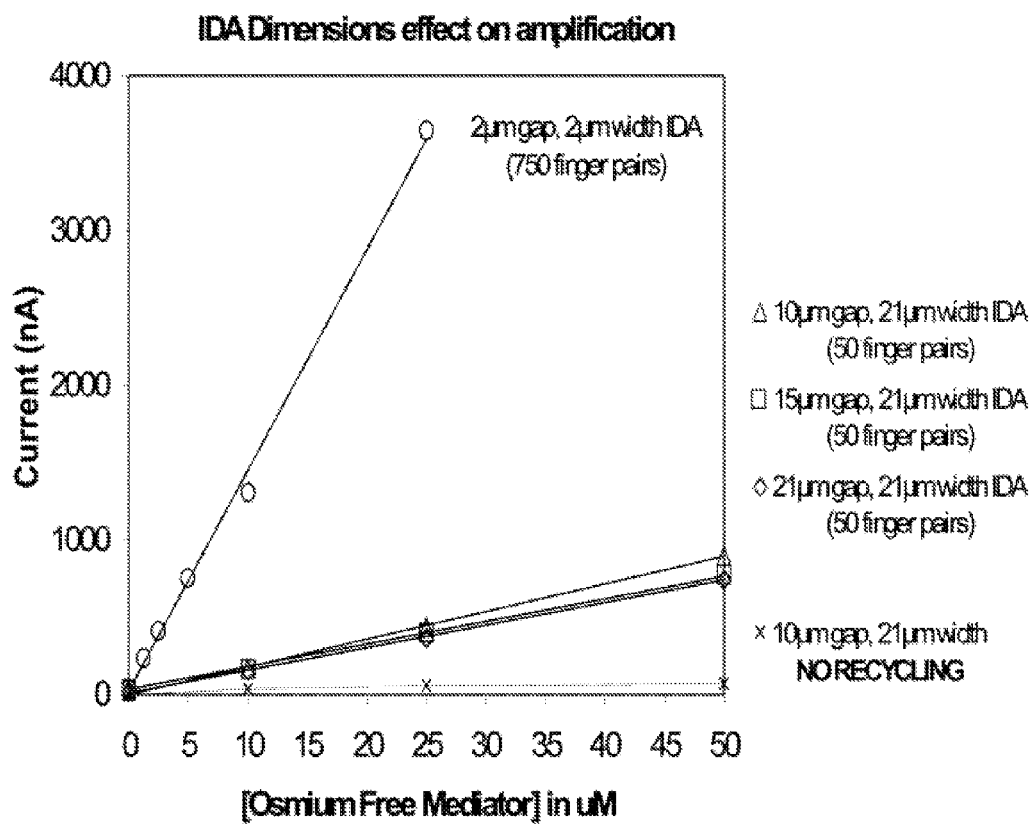
FIG. 16 is a graph illustrating the ability to increase the current amplification by decreasing the gap width between the electrodes in an IDA in accordance with the present invention.

In addition to using the equations to compare the predicted vs. experimental values, Equations 2, 4, and 6 were also used as a tool to design electrodes of proper dimensions in order to achieve electrodes that will achieve the desired response for specific immunoassays. In order to use the equations as a design tool, it was assumed that about 0.5-1 nA would be the low end detection sensitivity for a mass production bipotentiostat instrument. A prototype module meeting these criteria was designed and built to interface with a Handsprings Visor PDA. The planar IDA having 2 μm finger width and gap with 750 microband pairs each 6 mm in length listed in Table 3 of FIG. 15 was designed and constructed to improve the detection sensitivities to about 5 nM in the ideal case (1000 nM/215 nA=4.65 nM/nA). This 2 μm IDA design achieved significantly improved amplification compared to the electrodes with 10, 15, and 21 μm gaps as shown in FIG. 16. Assuming a 1 nA resolution and the measured slope of 152 nA/μM, the sensitivity would be about 7 nM.

Figure 49:
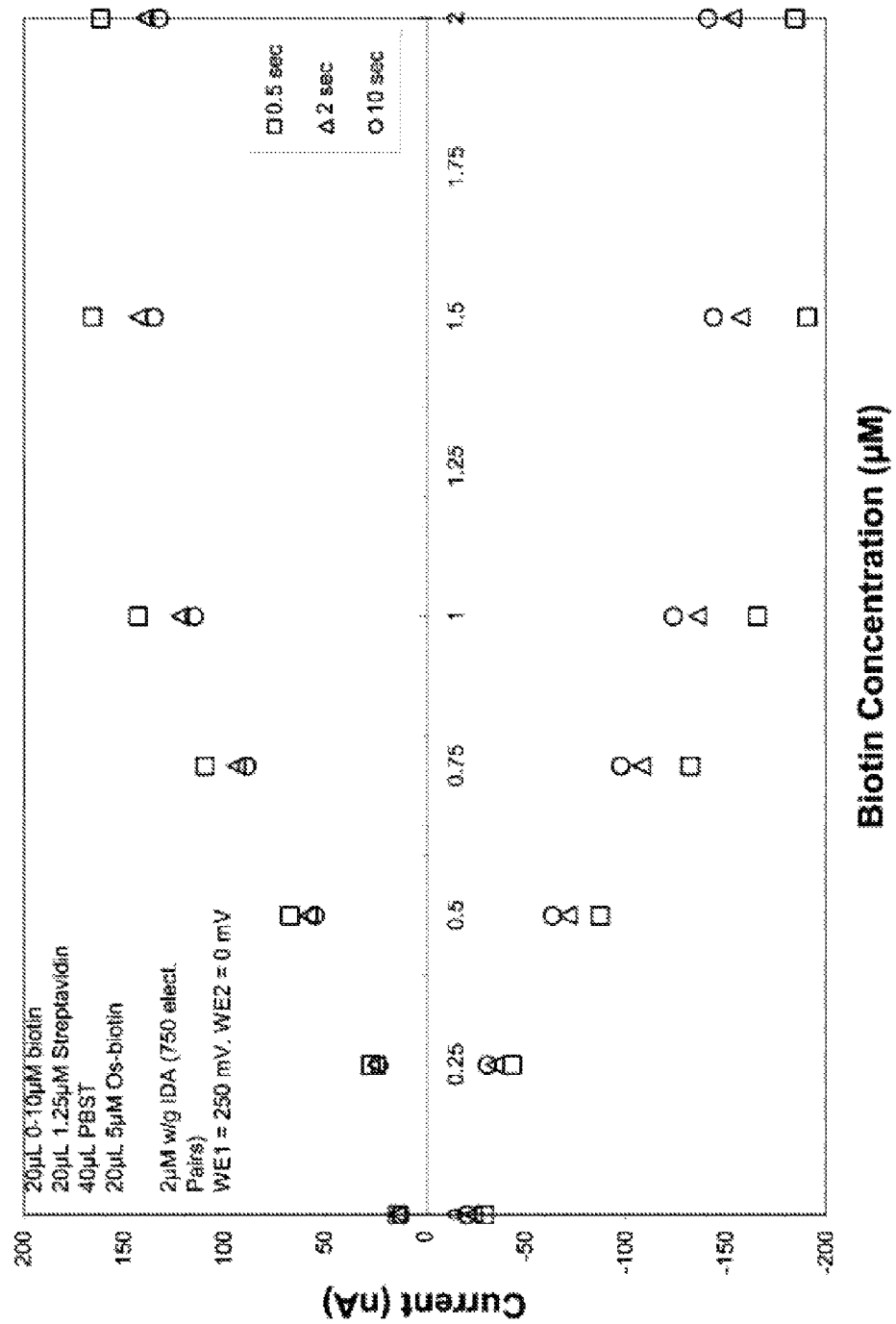
FIG. 49 is a plot of the steady-state response recorded at 0.5, 2, and 10 seconds after sample introduction for a biotin assay on a 2 μm IDA electrode.

FIG. 49 is a graph obtained from an osmium biotin assay prepared using the aforementioned 750 finger, 2 μm IDA electrode. The assay was configured for analyte measurement up to about 1000 nM based on the concentration of osmium biotin. The lowest level tested with this assay was 250 nM which was easily distinguished. Extrapolating the sensitivity to a 1 nA resolution provides an assay with a sensitivity of about 20 nM.

Figure 14:
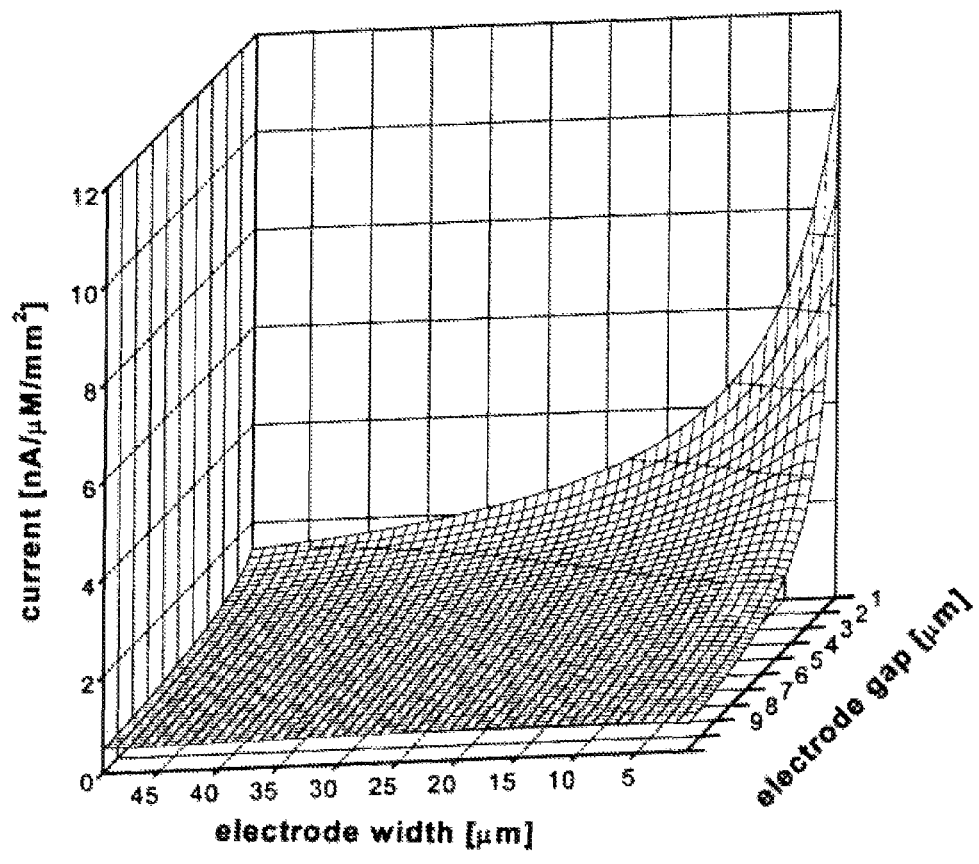
FIG. 14 is a three-dimensional plot of an electrical current vs. electrode dimensions for a planar IDA normalized for physical electrode area.

The three-dimensional plot shown in FIG. 14 shows normalized current vs. electrode dimensions for a series of planar IDAs of varying W and $W_g$. FIG. 14 shows that even with μm spaced IDAs, significant improvements in normalized currents can be made by decreasing W and $W_g$.

FIG. 16 is a graph plotting the current (in nA) measured on different IDA electrodes using the osmium free mediator (Bis(2,2'-Bipyridyl)Imidazole Chloro Osmium (III)dichloride). The IDAs were prepared as described herein and included electrode structures with 50 finger pairs each having a width (W) of about 21 μm and a gap ($W_g$) of 10, 15, and 21 μm. Another electrode structure had 750 finger pairs each having $W=W_g=2$ μm. All electrodes had a finger length (b) of 6 mm. This plot illustrates the magnitude of IDA amplification that were tested on different IDA electrode configurations. One feature of the IDA electrodes of the present invention is that rather large electrode areas (36 mm$^2$) and large number of fingers (750 pairs) can be fabricated and used for electrochemical immunoassays. From the graphs and equations it was observed that decreasing W and $W_g$ and increasing the number of fingers all can contribute to an increase in the measurable current on an IDA. FIG. 16 also illustrates the particularly small current obtained for an IDA when there is no redox recycling.

The "Cell Constant" is a useful value that can be both calculated and measured for a particular electrode configuration. The characteristics of two electrodes of the same cell constants should function similarly in the application of electrodes of this invention and can be used to compare various electrode configurations. Electrodes of interest for this invention are electrodes with about equal or smaller cell constants than those used to perform the homogeneous electrochemical immunoassays of this invention as shown in Table 4. Preferably the IDA cell constant for electrodes of the present invention is less than about 0.03 cm$^{-1}$ for analytes at high concentrations such as theophylline, even more preferred would be electrode structures with a cell constant of less than about 0.02 cm$^{-1}$, and most preferably smaller than about 0.002 cm$^{-1}$. IDA electrodes whose cell constants are less than about 0.0025 cm$^{-1}$ provide good redox recycling and amplification with the osmium electrochemical mediator conjugates discussed herein for homogeneous electrochemical immunoassays. Table 4 below lists the cell constants for electrodes of this invention along with the cell constants for some of the typical IDA electrodes that have been reported and studied for various electrochemical measurements. It is apparent from the table that the electrodes that are preferred for this invention have smaller cell constants than those commonly described in the literature although not necessarily smaller electrode gaps and widths. Although most researchers are moving towards more closely spaced IDA electrode widths and gaps, they have also often significantly reduced the finger length and thus the electrode cells are much smaller in overall dimensions. Thus, the small cell constants desired for this invention has usually not been realized.

Techniques such as E-beam lithography are becoming more commonly used to produce IDA electrodes with small features. At the present time, this technique is not amenable to high volume, low cost disposable sensors. The preferred electrodes of this invention are designed to achieve the required signal amplification based on the required immunoassay sensitivity. Electrodes that are amenable to high speed reel to reel processing such as standard photolithography techniques and laser ablation are most preferred for disposable immunoassay sensors. Designs that minimize the cell constants, not necessarily the smallest electrode features, are the preferred electrode designs. Small electrode features are desirable if the cell constants are also decreased which can be achieved by adjusting the length and/or number of IDA fingers.

TABLE 4

| Electrode structures of invention or cited in literature. | m = pairs of microband electrodes | W = Electrode width (μm) | $W_g$ = Electrode gap (μm) | b = length of band (cm) | Cell Constant (cm$^{-1}$) |
| --- | --- | --- | --- | --- | --- |
| Immunosensor electrodes per this invention | 750 | 2 | 2 | 0.6 | 0.0022 |
|  | 150 | 5 | 5 | 0.3 | 0.0215 |
|  | 50 | 21 | 10 | 0.6 | 0.0254 |
|  | 50 | 21 | 15 | 0.6 | 0.0290 |
|  | 50 | 21 | 21 | 0.6 | 0.0323 |
| J. Electroanal. Chem., 256 (1988) 269-282 | 25 | 10 | 5 | 0.2 | 0.1546 |
|  | 50 | 5 | 5 | 0.2 | 0.0970 |
|  | 50 | 3 | 5 | 0.2 | 0.1132 |
|  | 25 | 10 | 2 | 0.2 | 0.1152 |

TABLE 4-continued

| Electrode structures of invention or cited in literature. | m = pairs of microband electrodes | W = Electrode width (μm) | $W_g$ = Electrode gap (μm) | b = length of band (cm) | Cell Constant ($cm^{-1}$) |
|---|---|---|---|---|---|
| | 50 | 5 | 2 | 0.2 | 0.0718 |
| | 50 | 3 | 2 | 0.2 | 0.0850 |
| Analytica | 70 | 3 | 1 | 0.09 | 0.1074 |
| Chimica Acta | 35 | 1.5 | 0.7 | 0.09 | 0.2399 |
| 305 (1995) | 35 | 1.5 | 0.5 | 0.09 | 0.2148 |
| 126-136 | 35 | 1.5 | 0.3 | 0.09 | 0.1828 |
| | 224 | 1 | 0.5 | 0.09 | 0.0383 |

Enzyme Amplification

As an alternative to IDA amplification, homogeneous electrochemical immunoassays can also be developed with enzyme amplification. For some antigens, the enzyme amplification was the preferred method since redox recycling of the prepared mediator did not recycle properly with the conjugate. One example was with an osmium morphine conjugate shown below.

Assay Schemes

Various assay schemes of this invention are described below. All of these schemes require that the reagents are dried in one or more regions of the test sensor. In order for the assays to be viable, fast solubility of the reagents are required with the addition of sample. For this reason, it is highly desirable that the electrochemical labels, binding partners, and other supporting reagents solubilize in the sample matrix.

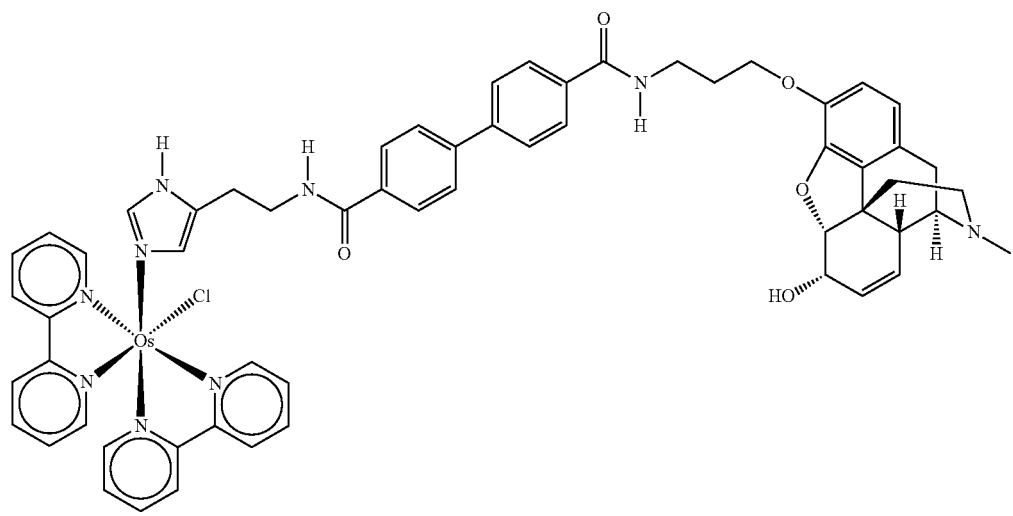

Several examples of enzyme assays were developed including: cocaine, morphine, THC, and biotin. The premise for enzyme amplification is that the electrochemical mediator label is reduced by the enzyme and oxidized on the electrode surface. Since enzymes are very efficient, this method competes well with IDA amplification techniques and is applicable to many assays. There are, however, several disadvantages with enzyme amplification including the ability to amplify sources of noise such as interfering substances. Addition of enzyme to the device also requires additional reagents to ensure enzyme stability. In addition, one must also balance the preferred pH of the enzyme vs. antibody. Advantages include simpler electrode structures similar to those used in glucose sensors.

For this reason, conjugates of hydrophobic antigens will often require the use of hydrophilic linkers to improve the solubility of the reagent such as the osmium-PEG-THC-2 (compound 37) and PEG-methotrexate (compound 38). In addition, the hydrophobic nature of the antigen itself in the sample and on the conjugate is also a concern for nonspecific binding and hydrophobic interactions which can lead to a diminished conjugate response and assay result due to less antigen available for binding. Conjugates of hydrophobic antigens may also aggregate or form micelles since they are hydrophilic on one end and hydrophobic on the other. Electrode fouling or contamination which inhibits the electrochemistry is also a concern. The use of hydroxypropyl-β-cyclodextrin added to the reagents has been shown to greatly improve assays with these concerns possibly allowing the hydrophobic portion to go inside the cavity of cyclodextrin. It has also been shown that the use of the hydroxypropyl-β-cyclodextrin does not appear to inhibit the binding events.

Several assay schemes can be used in accordance with the present invention. The schemes include both homogeneous and heterogeneous immunoassay methods. The preferred method is the homogeneous competitive immunoassay that enables the direct measurement of unbound mediator conjugates without separation from the bound mediator conjugate. Thus the immunoassay can be carried out in one reaction mixture. Heterogeneous immunoassays, which will not be discussed in detail, require the use of a separation step to separate bound mediator conjugates from the free labeled.

Homogeneous immunoassays can be more readily adapted to a "point of care" or "in field" device of this invention. Two types of competitive binding assays have been employed. The first competitive binding assay is a displacement assay where the mediator labeled antigen is pre-bound to the antibody (or other binding partner). Then with the addition of antigen under non equilibrium conditions, the mediator labeled antigen is displaced. The assay can then measure the amount of unbound mediator label and correlate it to the concentration of the analyte. The second competitive binding assay is one in which the antigen is first brought in contact with excess antibody (or other binding partner) followed by the addition of the mediator labeled antigen which binds to the remaining antibody (or other binding partner). As with the displacement assay, the assay can then measure the amount of unbound mediator label and correlate it to the concentration of the analyte.

The specific activity of the electrochemical mediator labeled antigen is modulated according to the analyte concentration in the sample. The resulting current will be a function of the amount of analyte present.

Figure 17:
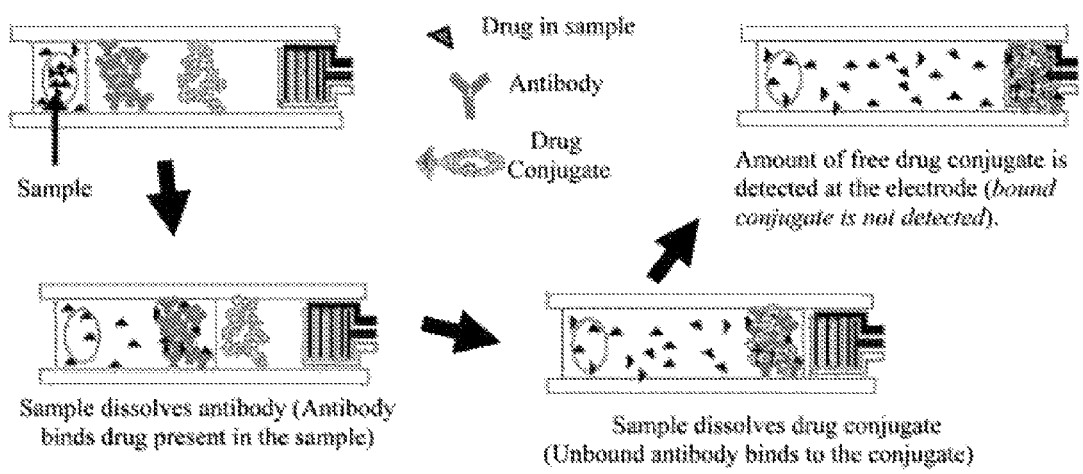
FIG. 17 is a diagram illustrating one embodiment of a sequential binding assay in accordance with the present invention.

FIG. 17 illustrates one embodiment of a competitive electrochemical homogeneous immunoassay test sensor that uses sequential binding. The figure illustrates a capillary test sensor where different reagents and the electrode structure are located. In this embodiment, the reagents (antibody and conjugate) are dried in a soluble matrix in locations upstream of the measurement zone. The measurement zone also includes the active electrode areas. The sample which may contain antigen is applied to a sample application port in sufficient volume to fill the capillary. As the sample fills the capillary and dissolves the reagents, the various binding events take place. When the sample and reagents reach the measurement zone, unbound mediator conjugate can be measured. Several variations of this basic system can be envisioned and included as part of this invention. In another embodiment, the reagents are mixed together and dried in the measurement zone either on the active electrode surface or on another surface of the measurement zone. In this configuration, no additional chambers or regions are required.

The illustrated homogeneous electrochemical immunoassay is based on specific affinity between antigens and antibodies. The antigen of interest (e.g. drug, peptide, or biotin) is labeled with an electroactive redox mediator to yield the redox reversible mediator labeled antigen (mediator conjugate). The sample being assayed is mixed with a predicted excess of the antibody to the antigen of interest. If the antigen is present in the sample, binding between the antigen and the antibody occurs. The resulting mixture of bound antigen-antibody and the excess unbound antibody is then combined with the redox reversible mediator labeled antigen. The unbound antibody binds to the antigen of the redox reversible conjugates to form a bound complex. The resulting mixture contains the redox reversible unbound conjugate, and the bound conjugate. The redox recycling of the bound conjugate is inhibited by the binding of the large molecular weight binding partner. In this embodiment, a predetermined amount of the specific antibody to the antigen of interest is combined with the sample, and thereafter, is added to a predetermined amount of the redox reversible conjugate. Applying a potential selected to induce the unbound redox reversible label to undergo redox recycling at the electrodes generates a current, which can be measured and correlated with analyte concentration.

The above illustration is based on specific affinity between antigens and antibodies. It will be understood that any analyte of interest and its specific binding partner can be used in place of the antigen/antibody combination.

In alternative embodiments, it is also possible to combine the predetermined amounts of the antibody with the redox reversible conjugate to form the respective complexes prior to combining those components with the liquid sample. In the latter case, the redox reversible conjugate will be displaced from its respective antibody by the corresponding antigen to provide a concentration of the redox reversible conjugates proportionate to the concentration of antigen in the liquid sample.

The reagents, that is, the predetermined amounts of the antibody for the antigen and the predetermined amounts of the corresponding redox reversible conjugate can, for example, be deposited in a vessel for receiving a predetermined volume of the liquid sample. The liquid sample is added to the vessel, and thereafter, or simultaneously, the liquid sample is contacted with the electrode structure.

Two homogeneous immunoassay formats can be implemented for assays: displacement and, sequential binding. Both assays electrochemically detect the amount of free (unbound) conjugate at the end of the assay sequence. Interdigitated array (IDA) electrodes or enzymes are used to amplify the current signal through redox cycling of the mediator label. Measured current due to redox cycling is proportional to the amount of free (unbound) conjugate and increases with analyte concentration. In the case of IDA amplification, a steady-state response is obtained within seconds of applying the sample and the proper redox potentials to the first and second working electrodes via a bipotentiostat.

Recycling with a bipotentiostat should result in two measurements that are equal in magnitude but opposite in sign. This provides distinct advantages in determining if there is an interferent effect due to a non recycling interferent which would cause deviation from the expected value. Typically when interferents are present in low enough concentrations and when they do not undergo redox recycling, the potential interferents are not present in the final steady state current after a short period of time. Non recycling interferents at concentration of 10 to 100 times the concentration of the desired analyte can still be negligible when using redox recycling measurements since the interferent does not recycle.

Interferents at significantly higher concentration, i.e. as is possible with ascorbic acid in urine, can show a large increase in the oxidation response and a smaller decrease in the reduction response from the expected result. It is expected that by use of both the oxidation and reduction response, the analyte of interest may be able to be corrected by mathematical computations.

Ascorbic acid (Vitamin C) concentrations in biological samples can vary dramatically. In random urine samples, the concentration can range between 60-400 µM. In plasma the range is 34-91 µM and in whole blood 40-114 µM. Ascorbic acid is a strong reducing agent, thus it is readily oxidized and can be a source of electrochemical interference with clinical tests.

In one study, the effect of ascorbic acid was studied on 21 µm IDA electrodes using osmium free mediator at 1, 5, and 10 µM. The ascorbic acid was varied at 100, 200, and 400 µM. Measurements were made using a CHI 832A bipotentiostat with WE1=250 mV, WE2=0 mV. The 100 µM sample showed little deviation from the control but the 200 and 400 µM severely shows the reductive properties of ascorbic acid. In comparison to the control, the 200 and 400 µM samples, the oxidation currents were greatly increased and the reduction currents were diminished. For oxidation, an increase in the slope of the OSFM response was observed as well as an increase in the Y intercept. For reduction the opposite trend was observed, a decrease in the slope and decrease in the Y intercept. It is expected that faster recycling IDA electrodes (electrodes with smaller W and $W_g$) would have less interferences from non redox recycling interferents.

Sample Treatment

The method can be performed on liquid samples comprising biological fluids such as saliva, urine, or blood, or the liquid sample can be derived from environmental sources. The liquid samples can be analyzed neat "as is" or pre-processed such as diluted with a buffered solution, concentrated or otherwise processed to optimize detection of the targeted analyte(s). Thus, for example, blood samples can be lysed and/or otherwise denatured to solubilize cellular components. In another example urine samples can be mixed with a predetermined amount of ascorbate oxidase. Hydroxypropyl-β-cyclodextrin may also be added to samples containing an analyte of hydrophobic nature to minimize nonspecific binding of the analyte to the surface of the sample collection containers, reagent, or measurement zones. The method can be performed using widely variant sample handling techniques.

The present invention includes at least one electrochemical label for each analyte to be detected and/or analyzed. Illustrative examples of an osmium electrochemical label for use in this invention are complexes of the Compound 1:

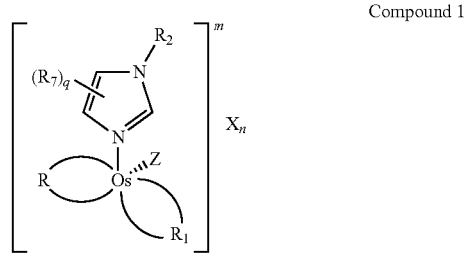

Compound 1 wherein R and $R_1$ are the same or different and each can be selected from: 2,2'-bipyridyl, 4,4'-disubstituted-2,2'-bipyridyl, 5-5'-disubstituted-2,2'-bipyridyl, 1,10-phenanthrolinyl, 4,7-disubstituted-1,10-phenanthrolinyl, or 5,6-disubstituted-1,10-phenanthrolinyl, wherein each substituent is a methyl, ethyl, or phenyl group, and where the R and $R_1$ groups are coordinated to Os through their nitrogen atoms; q is 1 or 0; $R_7$ is B-$(L)_k$-Q$(CH_2)_i$; $R_2$ is hydrogen, methyl, or ethyl when q is 1, and $R_2$ is B-$(L)_k$-Q$(CH_2)_i$— when q is 0; for the group B-$(L)_k$-Q$(CH_2)_i$: Q is O, S, or $NR_4$, wherein $R_4$ is hydrogen, methyl or ethyl; -L- is a divalent linker; k is the integer 1 or 0; i is an integer 1, 2, 3, 4, 5 or 6; and B a group comprising a ligand capable of binding to a specific analyte binding partner; Z is chloro or bromo; m is +1 or +2; X is counter ion such as a mono- or divalent anion, e.g., chloride, bromide, iodide, fluoride, tetrafluoroborate, perchlorate, nitrate, sulfate, carbonate, or sulfite; and n is selected to provide a neutral salt.

A second illustrative example of an osmium electrochemical label for use with the present invention is represented by Compound 2:

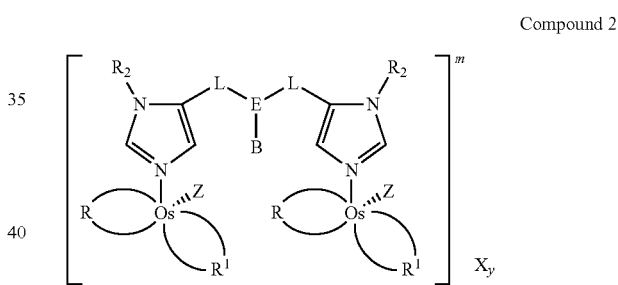

Compound 2 wherein R and $R^1$ are the same or different and each can be selected from: 2,2'-bipyridyl, 4,4'-disubstituted-2,2'-bipyridyl, 5-5'-disubstituted-2,2'-bipyridyl, 1,10-phenanthrolinyl, 4,7-disubstituted-1,10-phenanthrolinyl, 5,6-disubstituted-1,10-phenanthrolinyl, or N,N'-dimethyl 2,2'-biimidazole, wherein each substituent is a methyl, ethyl, or phenyl group, and where the R and $R^1$ groups are coordinated to osmium through their nitrogen atoms; $R^2$ is hydrogen, methyl, or ethyl; -L- is a linker; E is a trivalent linker; B is a group comprising a ligand capable of binding to a specific analyte binding partner; Z is chloro or bromo; X is a counter ion; and y is selected to provide a neutral salt; and m is 2 to 4.

A third illustrative example of an osmium electrochemical label for use with the present invention is represented by Compound 3.

Compound 3

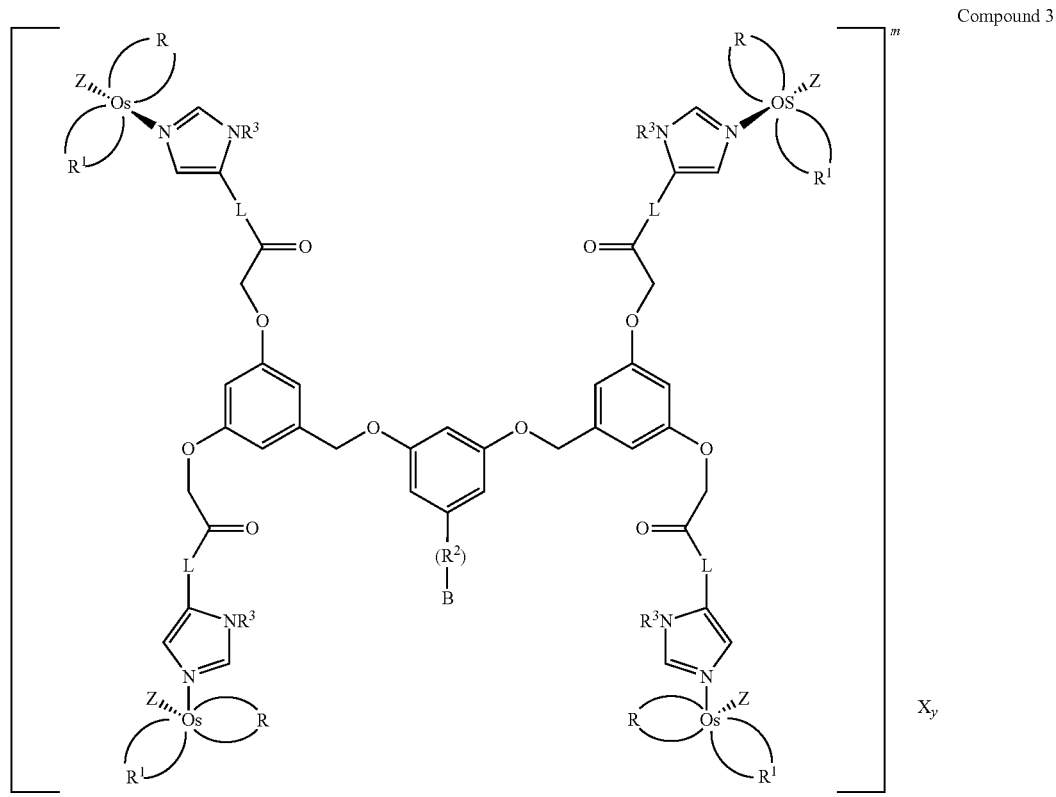

wherein, R and R[1] are the same or different and each can be selected from: 2,2'-bipyridyl, 4,4'-disubstituted-2,2'-bipyridyl, 5-5'-disubstituted-2,2'-bipyridyl, 1,10-phenanthrolinyl, 4,7-disubstituted-1,10-phenanthrolinyl, 5,6-disubstituted-1,10-phenanthrolinyl, or N,N'-dimethyl 2,2'-biimidazole, wherein each substituent is a methyl, ethyl, or phenyl group, and where the R and R[1] groups are coordinated to Os through their nitrogen atoms, R[2] is a saturated or unsaturated, substituted or unsubstituted, straight or branched chain, hydrocarbyl group having 1-10 carbon atoms; —R[3] is H, CH$_3$ or C$_2$H$_5$; L is (CH$_2$)$_i$Q wherein i is an integer between 1 and 10, and Q is O, S, or NR[3]; B is a group comprising a ligand capable of binding to a specific analyte binding partner; X is a counter ion; y is selected to provide a neutral salt; and m is from 4-8.

A fourth illustrative example of an osmium electrochemical label for use with the present invention is represented by Compound 4 below.

Compound 4

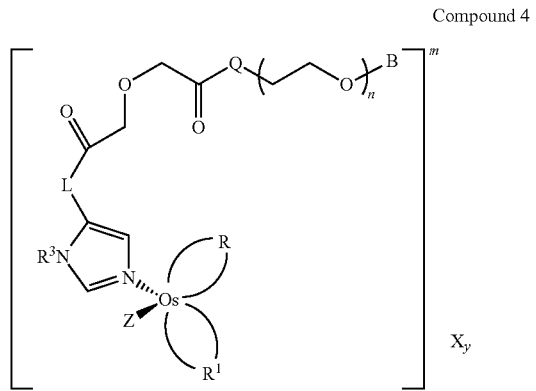

wherein, R and R$_1$ are the same or different and each can be selected from: 2,2'-bipyridyl, 4,4'-disubstituted-2,2'-bipyridyl, 5-5'-disubstituted-2,2'-bipyridyl, 1,10-phenanthrolinyl, 4,7-disubstituted-1,10-phenanthrolinyl, 5,6-disubstituted-1,10-phenanthrolinyl, or N,N'-dimethyl 2-2'-biimidazole wherein each substituent is a methyl, ethyl, or phenyl group, and where the R and R[1] groups are coordinated to Os through their nitrogen atoms; R[3] is H, CH$_3$ or C$_2$H$_5$; L is (CH$_2$)$_i$Q, wherein i is an integer 1-10 and Q is O or NR[3]; B is a group comprising a ligand capable of binding to a specific analyte binding partner; Z is chlorine or bromine; X is a counter ion; y is selected to provide a neutral salt; and m is 1 or 2.

The precursor to compound 4 (where the B substituent is replaced with A: —(CH$_2$)$_j$—NR[3], —(CH$_2$)$_j$—SH, or an activated ester wherein j is an integer between 1-5) is also included within the scope of the present invention.

As illustrated above for Compounds 1, 2, and 3 the osmium mediator conjugate(s) can be envisioned to comprise at least two and optionally three components. The osmium mediator conjugate can include one or more organometallic osmium group(s), one or more linking groups, and a ligand analog. The organometallic osmium species by itself, either as a free salt or with a neutral imidazole group, is electrochemically detectable. The di-chelating ligand on the osmium center, i.e., the bipyridyl and phenanthrolinyl ligands, can be varied as desired to provide a conjugate having the desired properties including redox potential and solubility. For example, for some fluid samples or specific analytes it may be desirable to employ an osmium conjugate that exhibits increased hydrophobicity. Varying the di-chelating ligands from a 2,2'-bipyridyl ligand to a 1,10-phenanthrolinyl ligand increases the hydrophobicity of the osmium complex; similarly, adding alkyl substituents to the di-chelating ligand also increases the hydrophobicity of the osmium complex.

The linking group L for use in the present invention can be selected depending upon a variety of factors including the particular analyte to be analyzed, its concentration, and the sample medium. In preferred embodiments, the linking groups can be selected based upon the particular analyte(s) of interest, its (or their) concentration in the sample medium, and the sample medium itself. The linking groups of the present invention can also be divalent linking groups. In one form, the linking group of the present invention can be selected to be hydrophilic. It has been determined that appropriate selection of the linking group can greatly influence the detection and analysis of particular analytes. For example, highly hydrophilic analytes can influence the mobility of the redox reversible conjugate in the sample medium in the reaction chamber. This, in turn, can affect the current amplification via either diffusional recycling under steady state conditions and/or enzyme recycling.

There are many types of conjugation chemistry that can be employed to link the osmium mediator to a ligand analog. The following conjugation chemistries employed for the preparation of osmium mediator-peptide conjugates have also been commonly used for preparing protein conjugates: 1) formation of amide bond by reactive ester with primary amine; and 2) formation of thioether bond by maleimide with sulfhydryl group; and formation of a urea or thio urea linkage by reaction of an amino group of osmium mediator with an isocyanate or isothiocyanate functionality of the drug derivatives Amide bond is preferred over thioether bond because amide bond is generally more stable. Based on the preferred conjugation chemistry, the ligand on the osmium mediator can be functionalized with either a primary amine group or a carboxylic acid group. The best location for these functional groups is believed to be the C-4 or C-5 positions on the imidazole ligand of the osmium mediator; however, functionalization through the non-osmium-complexed imidazole ring nitrogen atom can also be carried out.

In some osmium mediators, the amine group on the histamine ligand can be directly attached to the ligand analog, if a suitable reactive group exists or can be provided on the ligand analog. For example, the amine group on histamine ligand of osmium mediator readily reacts with an activated carboxyl group on methotrexate.

In one preferred embodiment of the present invention, one or more of the divalent linking groups is selected to exhibit sufficient hydrophilicity to enhance the mobility of the redox recycling conjugate in an aqueous medium. Examples of di-valent linking groups include: polyethylene glycol PEG either as a monomer, dimer, oligomer or short chain polymer.

In alternative embodiments, the linker itself can be connected to one or more crosslinking groups. For example, in the species illustrated above for either Compound 1, 2, or 3 a histadyl group (derived from histamine) is first attached to the osmium metal center. The histamine itself is a first linking group or moiety. It will be understood that a wide variety of linking groups can be used with the osmium complex. The resulting complexes are considered to be included within the scope of the present invention.

For the purpose of promoting further understanding and appreciation of the present invention and its advantages, the following examples are provided. It will be understood, however, that these examples are illustrative and not limiting in any fashion.

EXAMPLES

The term "Osmium Free Mediator" or "Free Mediator" or "OSFM" all refer to the use of bis(2,2'-bipyridyl)imidazole chloro osmium (III)dichloride, which is described in U.S. Pat. No. 5,589,326. This mediator is often used as a model electrochemical mediator to evaluate and compare redox amplification on various IDA electrodes. The structure of this mediator is shown below.

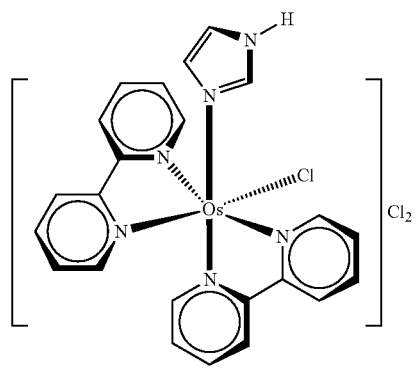

The notation "PBS" refers to a Phosphate Buffer Saline matrix consisting of 10 mM Potassium Phosphate Buffer, 2.7 mM Potassium Chloride, and 137 mM Sodium Chloride prepared from Sigma product #P4417 or a similar saline buffer matrix.

The notation "PBST" refers to a Phosphate Buffer Saline matrix consisting of 10 mM Potassium Phosphate Buffer, 2.7 mM Potassium Chloride, 137 mM Sodium Chloride, and about 0.1% to 0.5% Tween 20.

Reference to an "external Ag/AgCl" refers to a commercially available Ag/AgCl electrode such as the RE 803 mini-reference electrode from Abtech Scientific Inc., Richmond, Va.

The term "internal Ag/AgCl" refers to a Ag/AgCl ink applied to the sample contact region of a one of the electrodes of the electrode cell. In most cases this was a commercially available ink (product E2414) from Ercon, Wareham, Mass. The internal reference electrode as constructed on our electrodes had a potential shift in comparisons to the external Ag/AgCl reference electrode by about 100 mV.

Preparation of Osmium Electrochemical Labels

The bis(2,2'-bipyridyl)imidazolyl chloro osmium (III)dichloride (Osmium Free Mediator) has been shown to be an excellent electron mediator for many oxidoreductase enzymes (U.S. Pat. No. 5,589,326). It has fast mediation kinetics (about 500 times faster than ferricyanide with glucose oxidase) and a relatively low redox potential (+150 mV vs. Ag/AgCl). It has also a very fast electron transfer rate at electrode surfaces. Importantly, the organic ligands on the osmium conjugate can be functionalized so that it can be covalently linked to other molecules without detrimental effects on redox properties of the osmium center. These unique properties of osmium conjugate make it an ideal electrochemical label for affinity sensors. The osmium mediators can be prepared according to the procedure described in U.S. Pat. Nos. 6,294,062; 6,352,824; and 6,262,264, which are incorporated by reference in their entirety herein.

Osmium mediators with these new ligands were synthesized using the same or similar procedure used to synthesize the osmium free mediator. Their synthesis consists of two major process steps as outlined below. Details of these processing steps are described below.

The first process step involves the synthesis of osmium intermediate, cis-bis(2,2'-bipyridyl)dichloroosmium(II), from commercially-available osmium salt using the following scheme. The intermediate product is isolated through recrystallization in an ice bath.

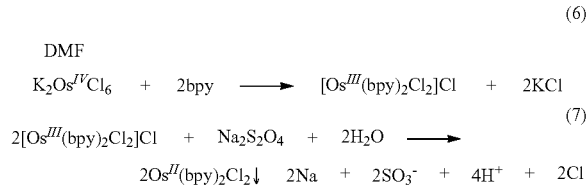

(6)

(7)

The second process step involves the reaction between the osmium intermediate and histamine to produce the desired osmium mediators. The desired product is then precipitated out from solution by addition of ammonium tetrafluoroborate.

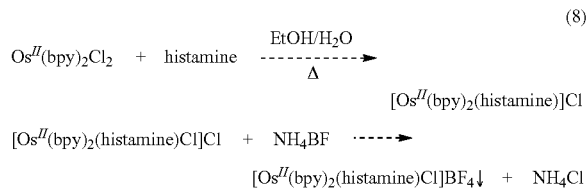

(8)

These osmium mediators can also be easily converted to the oxidized form, i.e., Os (III) using nitrosonium tetrafluoroborate. However, this is unnecessary since the osmium reverts back to the reduced form at alkaline conditions during conjugation reactions and the affinity assays do not require the oxidized form of Os (III) for the detection on the biosensor.

The free amino group of histamine in the osmium mediator (compound 5) was used to couple to the activated ester of drug derivative in general to give drug-osmium conjugates. Similar osmium conjugates have been prepared for HbA1c and HbA$_0$ peptides as described in U.S. Pat. No. 6,262,264.

Figure 18:
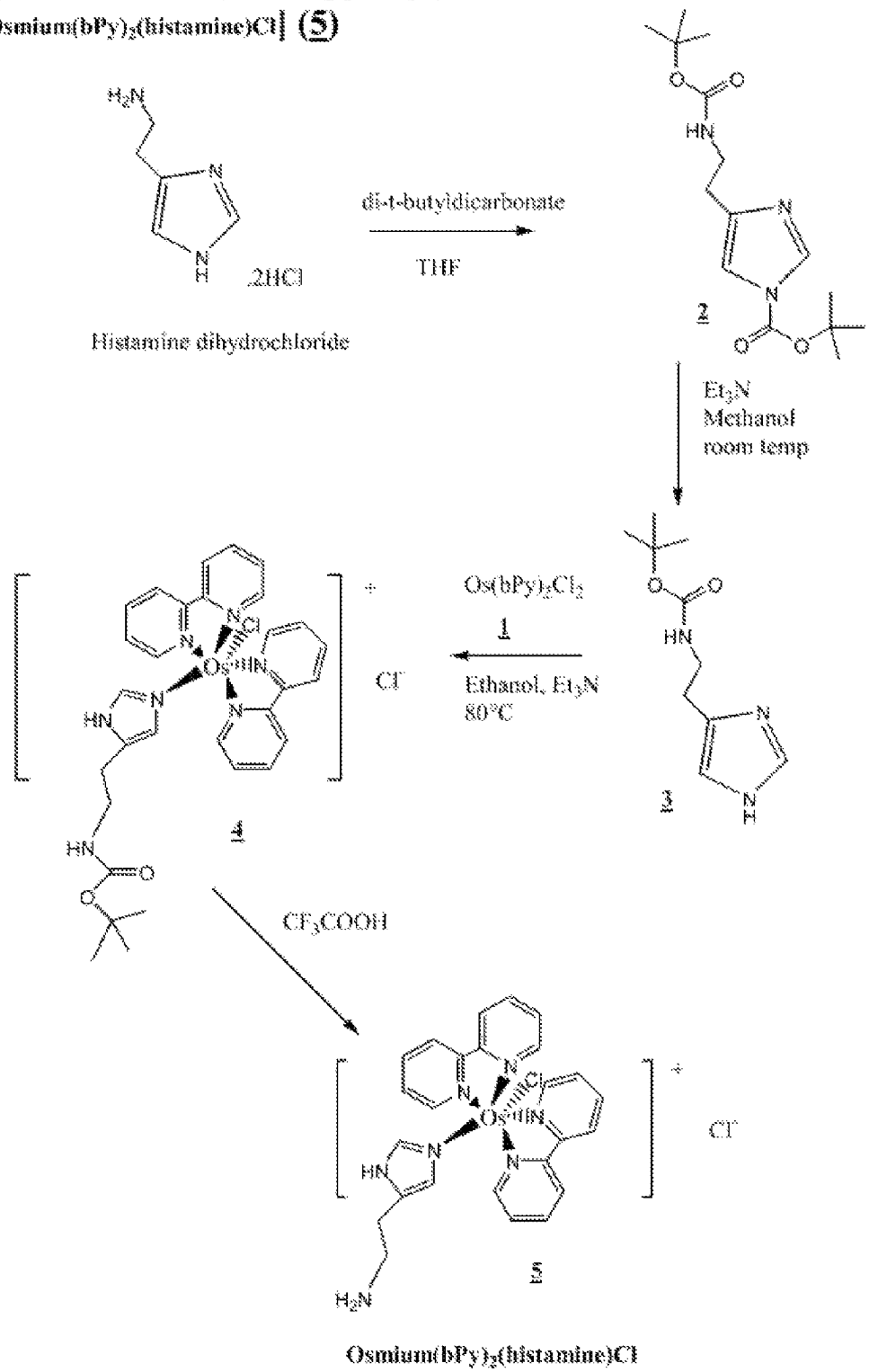
FIG. 18 illustrates one synthetic scheme for the preparation of an Os(bipyridyl)histamine electrochemical label in accordance with the present invention.

FIG. 18 illustrates an improved procedure for the synthesis of the key intermediate, bis(2,2'-bipyridyl)-histamine-chloro-osmium mediator (compound 5). The original procedure involves the reaction of histamine with cis-bis(2,2'-bipyridyl)dichloroosmium(II) in ethanol at a reflux condition. However, poor yield of the resulting desired product led to an alternative synthetic route using a protected histamine derivative as the starting material. Use of protecting groups in the organic chemistry is well-known in the art ("Protecting Groups in Organic Synthesis" by T. W. Green, John Wiley & Sons, 1981).

Thus, the primary amino group of histamine can be protected with a suitable protecting group, most preferably by using a tert-butoxycarbonyl protecting group (t-BOC) or trifluoroacetamido group. The histamine dihydrochloride was reacted with di-t-butyldicarbonate in THF to give di-t-BOC protected histamine derivative. The t-BOC group from the imidazole nitrogen was selectively removed by reaction with triethyl amine in methanol. The mono protected histamine was coupled with Os$^{II}$(bPy)$_2$Cl$_2$ to give protected histamine complex (compound 4). The t-BOC group of protected histamine was deprotected by reaction with trifluoroactic acid to give osmium (bPy)$_2$(histamine)Cl (compound 5).

Figure 19:
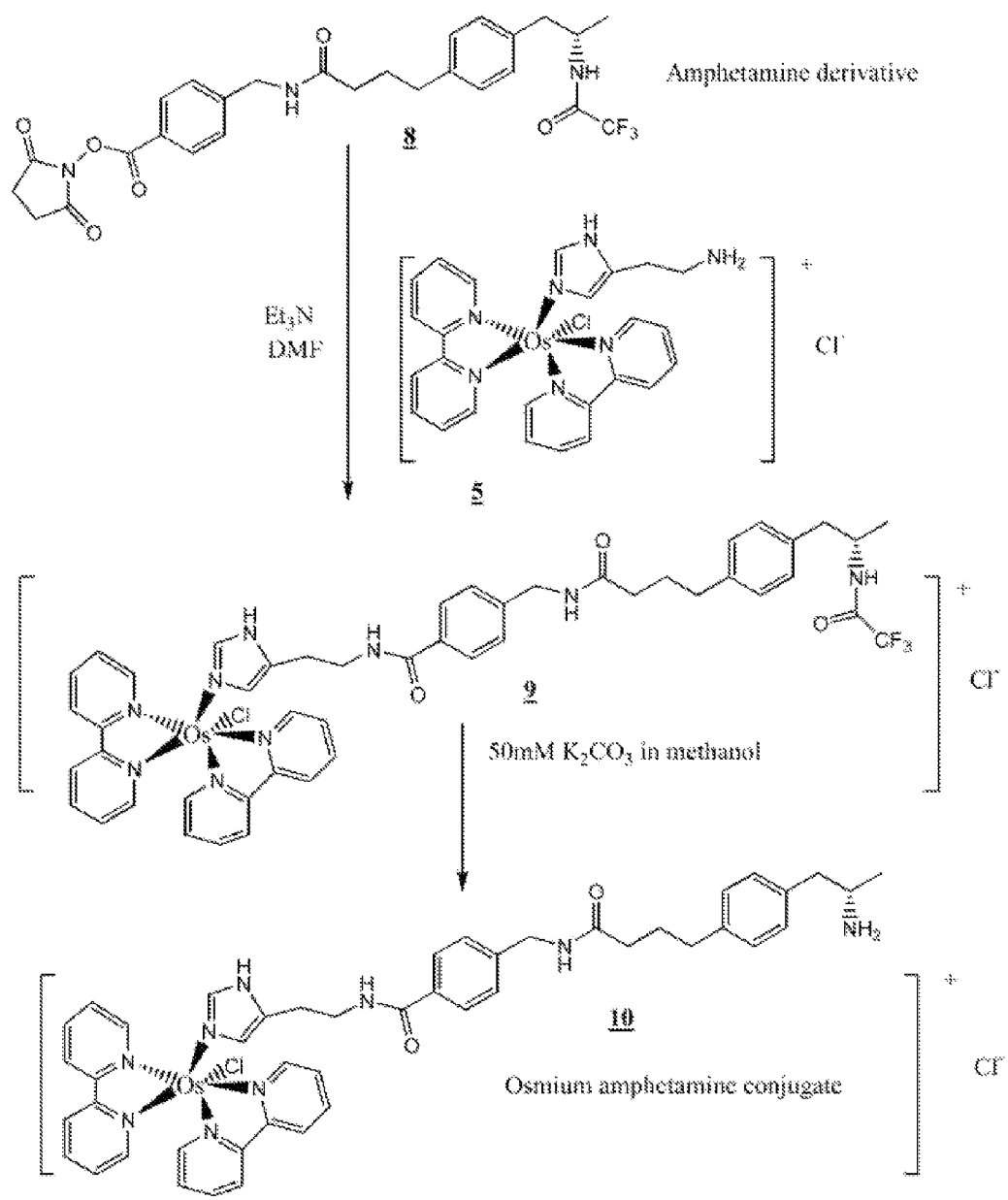
FIG. 19 illustrates a synthetic scheme for the preparation of an osmium-amphetamine conjugate in accordance with the present invention.

Several osmium histamine drug conjugates have been prepared. A representative example is the reaction of osmium (bPy)$_2$(histamine)Cl (compound 5) with an amphetamine NHS ester (compound 8) as shown in FIG. 19. The trifluoroacetamido group of the resulting osmium-amphetamine complex has been deprotected by reaction with 50 mM potassium carbonate to give amphetamine osmium conjugate (compound 10).

Figure 20:
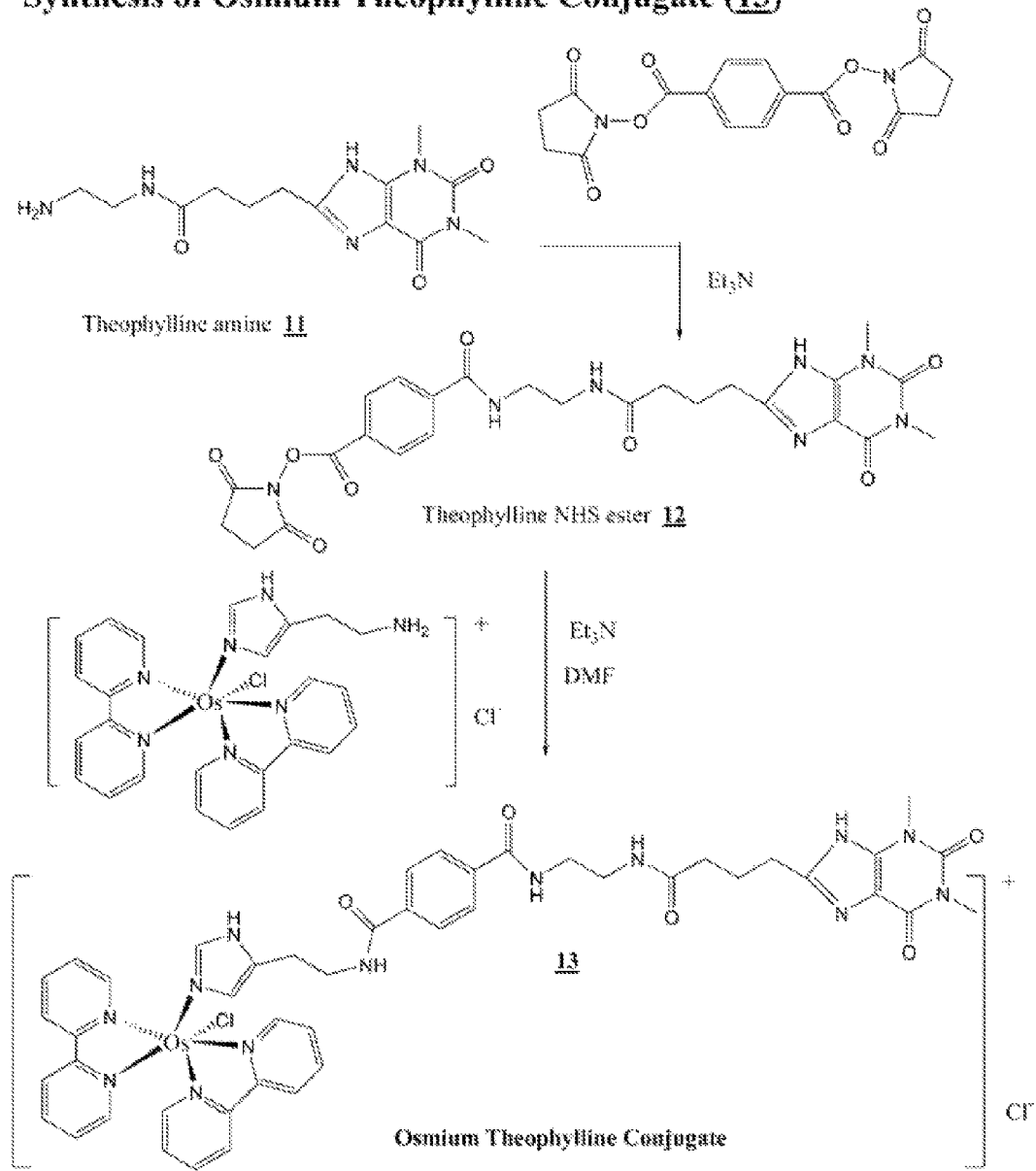
FIG. 20 illustrates a synthetic scheme for the preparation of an osmium-theophylline conjugate in accordance with the present invention.

The osmium theophylline conjugate (compound 13) was prepared as illustrated in FIG. 20. Theophylline amine (compound 11) was prepared according to the procedure published in WO 87/07955. Theophylline amine (compound 11) was reacted with terephthalic acid di-N-hydroxysuccinimide ester in the presence of triethyl amine to give theophylline N-hydroxysuccinimide ester (compound 12). This activated ester was coupled with osmium (bipy)$_2$(histamine)Cl (compound 5) in the presence of triethyl amine to provide the osmium theophylline conjugate (compound 13).

Figure 21:
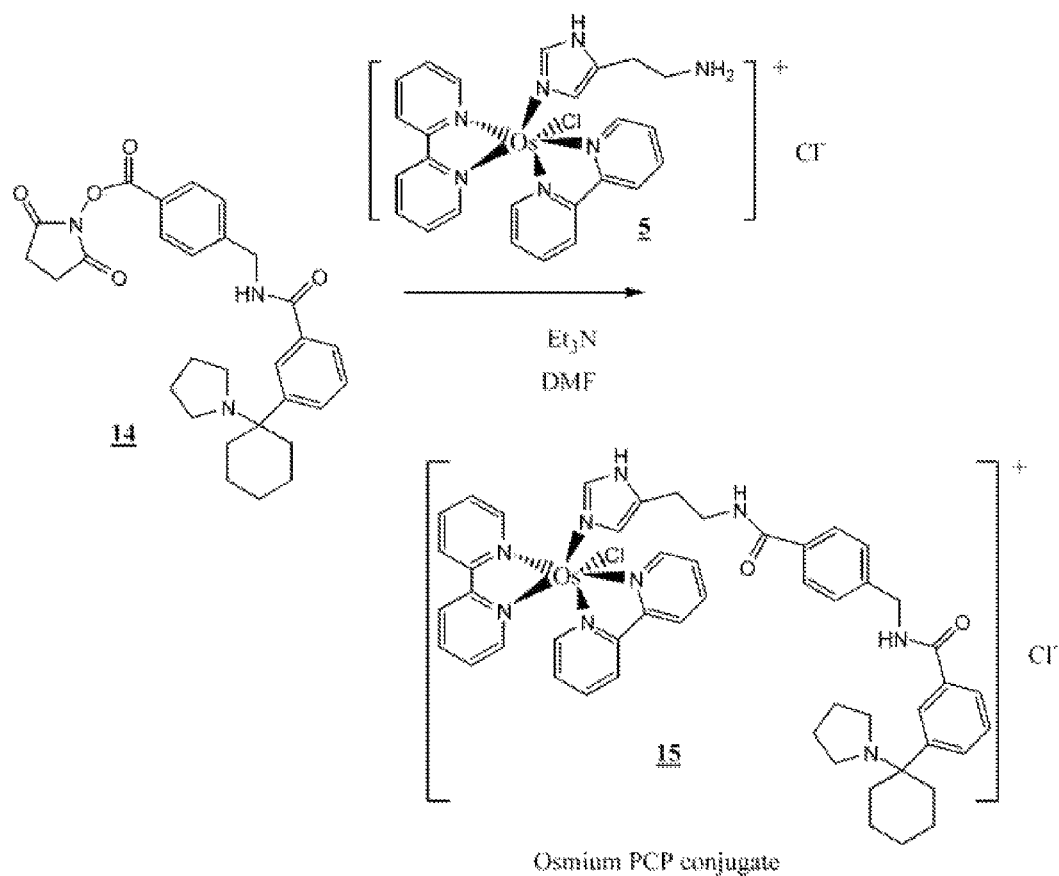
FIG. 21 illustrates a synthetic scheme for the preparation of an osmium-PCP conjugate in accordance with the present invention.

The PCP NHS ester (compound 14) was used to synthesize PCP-Osmium complex (compound 15) which is shown in FIG. 21. The PCP NHS ester (Compound 14) was prepared according to the procedures published in U.S. Pat. No. 5,939,332.

Figure 22:
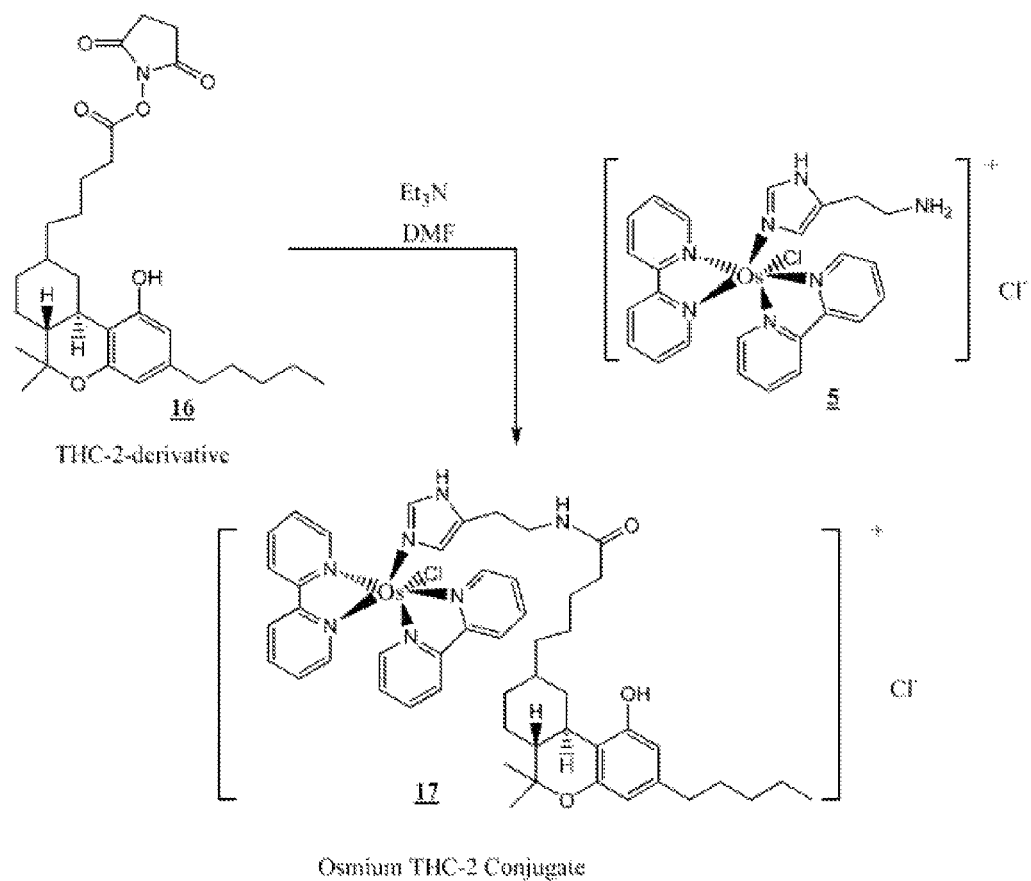
FIG. 22 illustrates a synthetic scheme for the preparation of an osmium-THC-2 conjugate in accordance with the present invention.

The synthesis of osmium THC-2 conjugate (compound 17) is described in FIG. 22. The synthesis of THC-2 derivative (compound 16) is described in EP 0736529A1.

Figure 23:
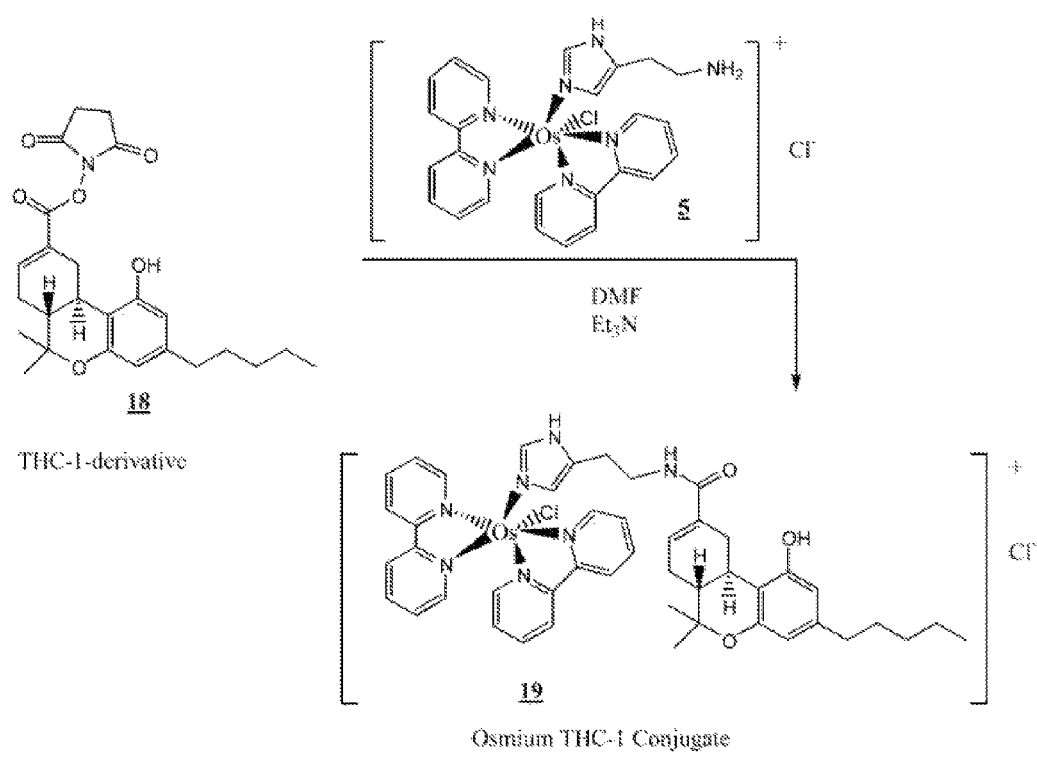
FIG. 23 illustrates a synthetic scheme for the preparation of an osmium-THC-1 conjugate in accordance with the present invention.

The synthesis of osmium THC-1 conjugate (compound 19), is described in FIG. 23. The synthesis of THC-1 derivative (compound 18) is described in *J. Org. Chem.* 1986, 51, 5463-5465.

Figure 24:
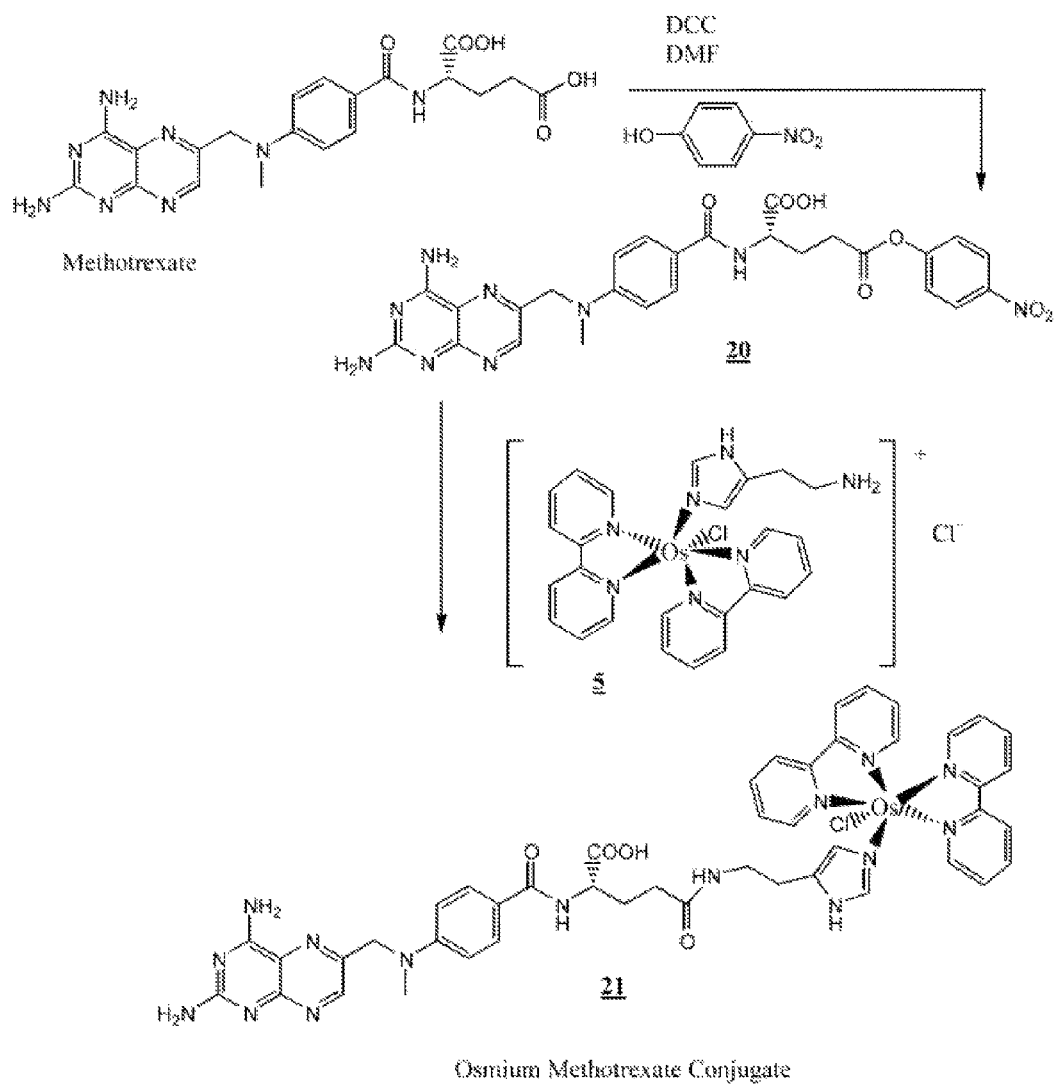
FIG. 24 illustrates a synthetic scheme for the preparation of an osmium-methotrexate conjugate in accordance with the present invention.
Figure 25:
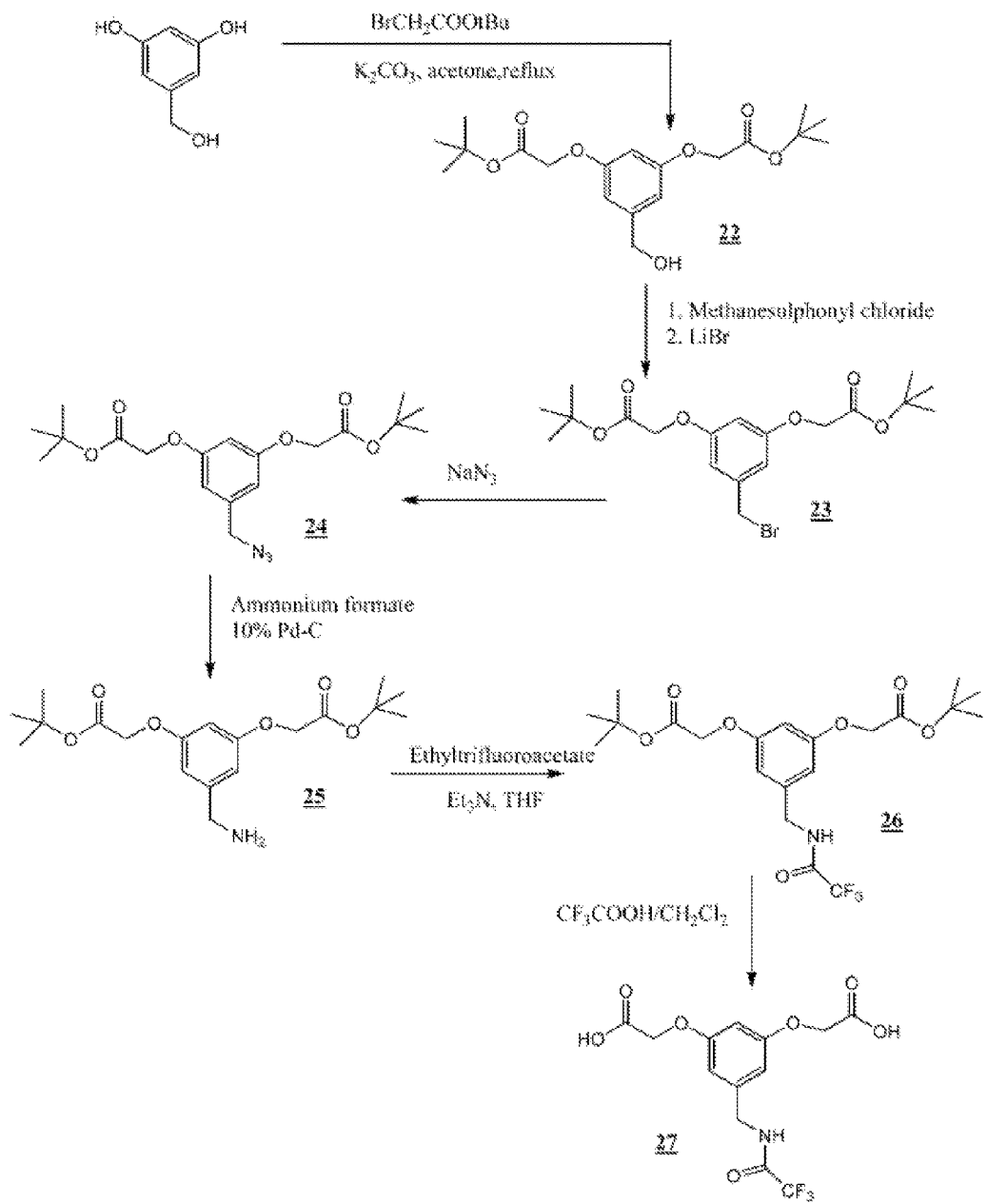
FIG. 25 illustrates a synthetic scheme for the preparation of an aromatic trifluoroacetamido protected linker for use in accordance with the present invention.
Figure 26:
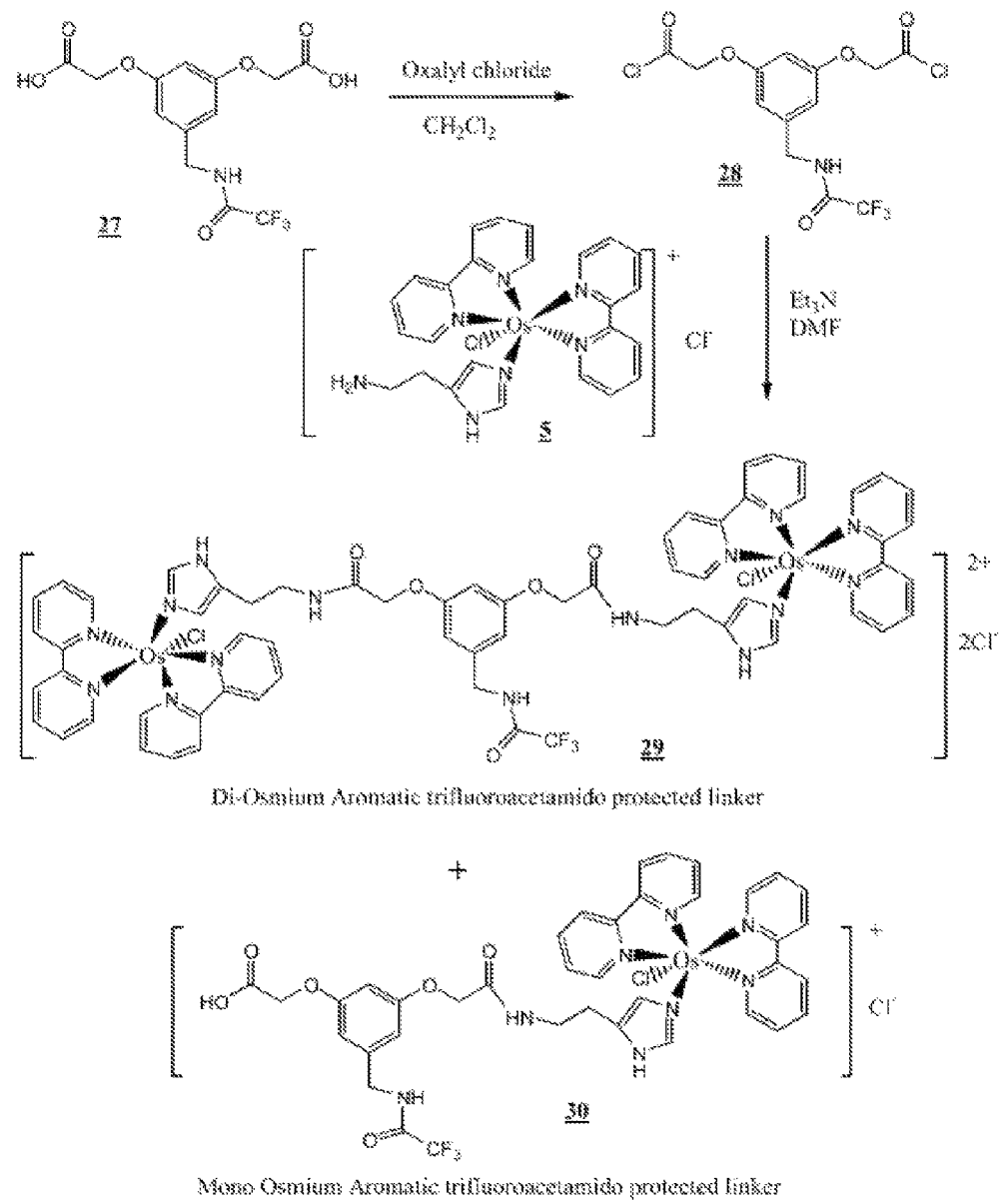
FIG. 26 illustrates a synthetic scheme for the preparation of a di-osmium aromatic trifluoroacetamido and mono osmium aromatic trifluoroacetamido protected linker or electrochemical label in accordance with the present invention.
Figure 27:
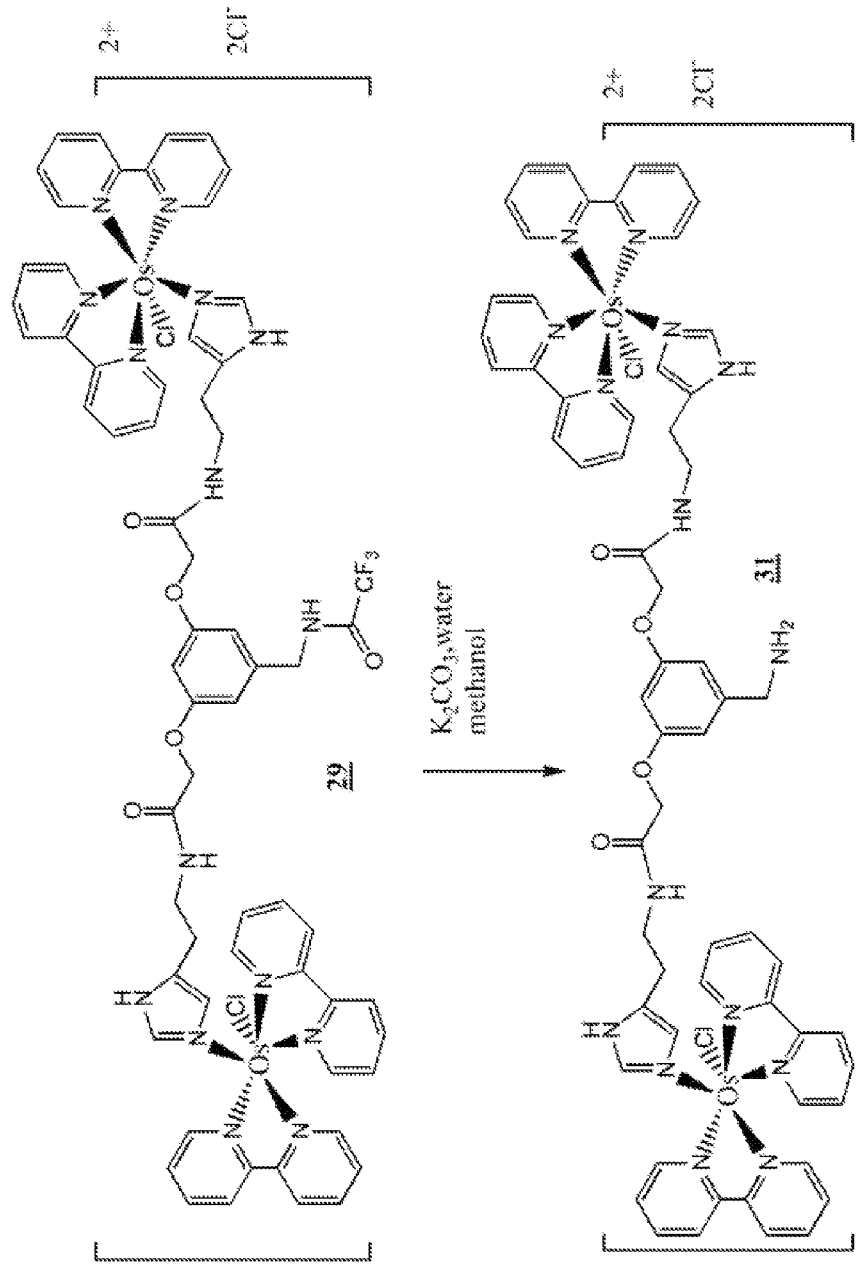
FIG. 27 illustrates a synthetic scheme for the preparation of a di-osmium electrochemical label with an aromatic linker in accordance with the present invention.
Figure 28:
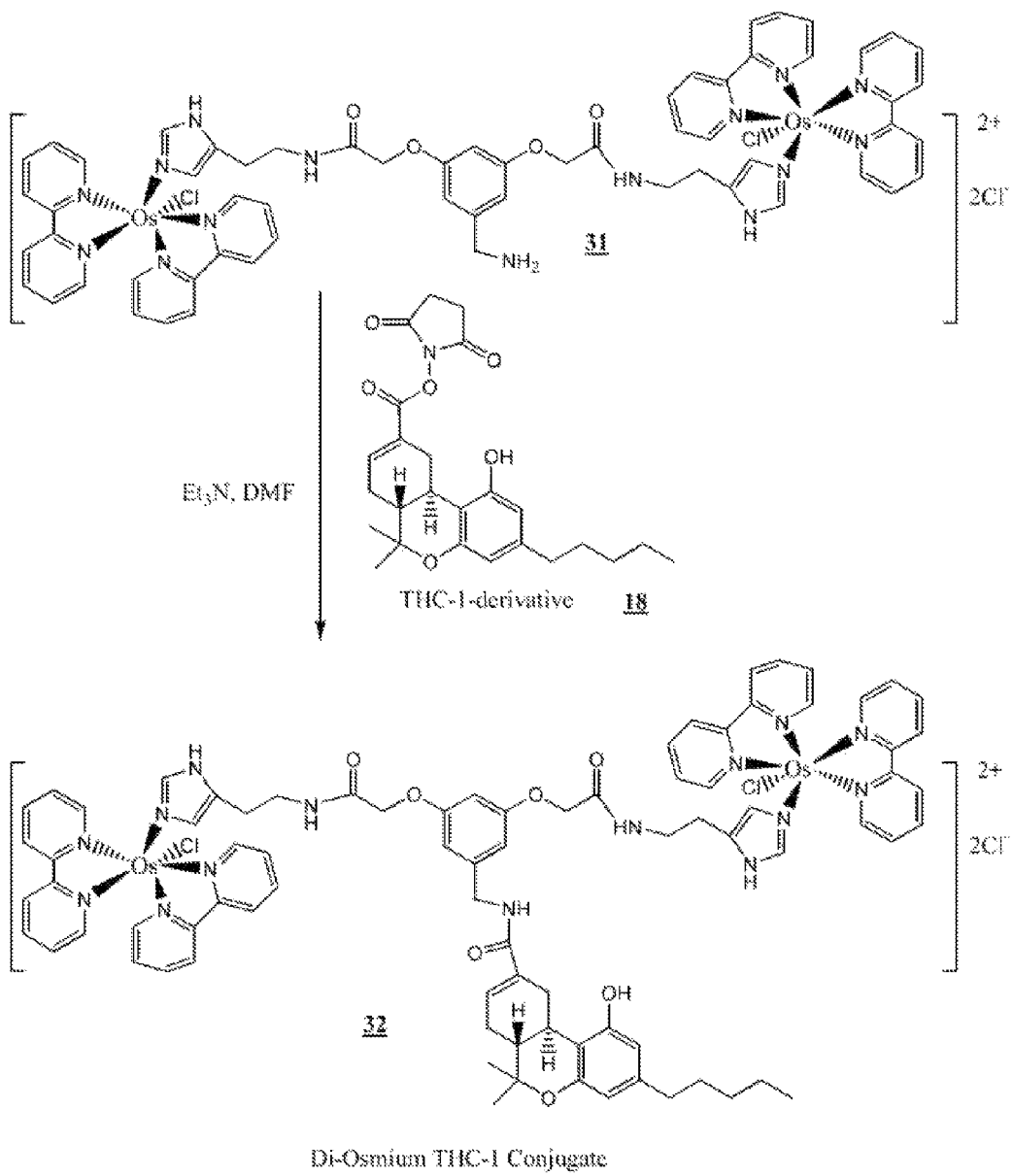
FIG. 28 illustrates a synthetic scheme for the preparation of a di-osmium THC-1 conjugate in accordance with the present invention.
Figure 29:
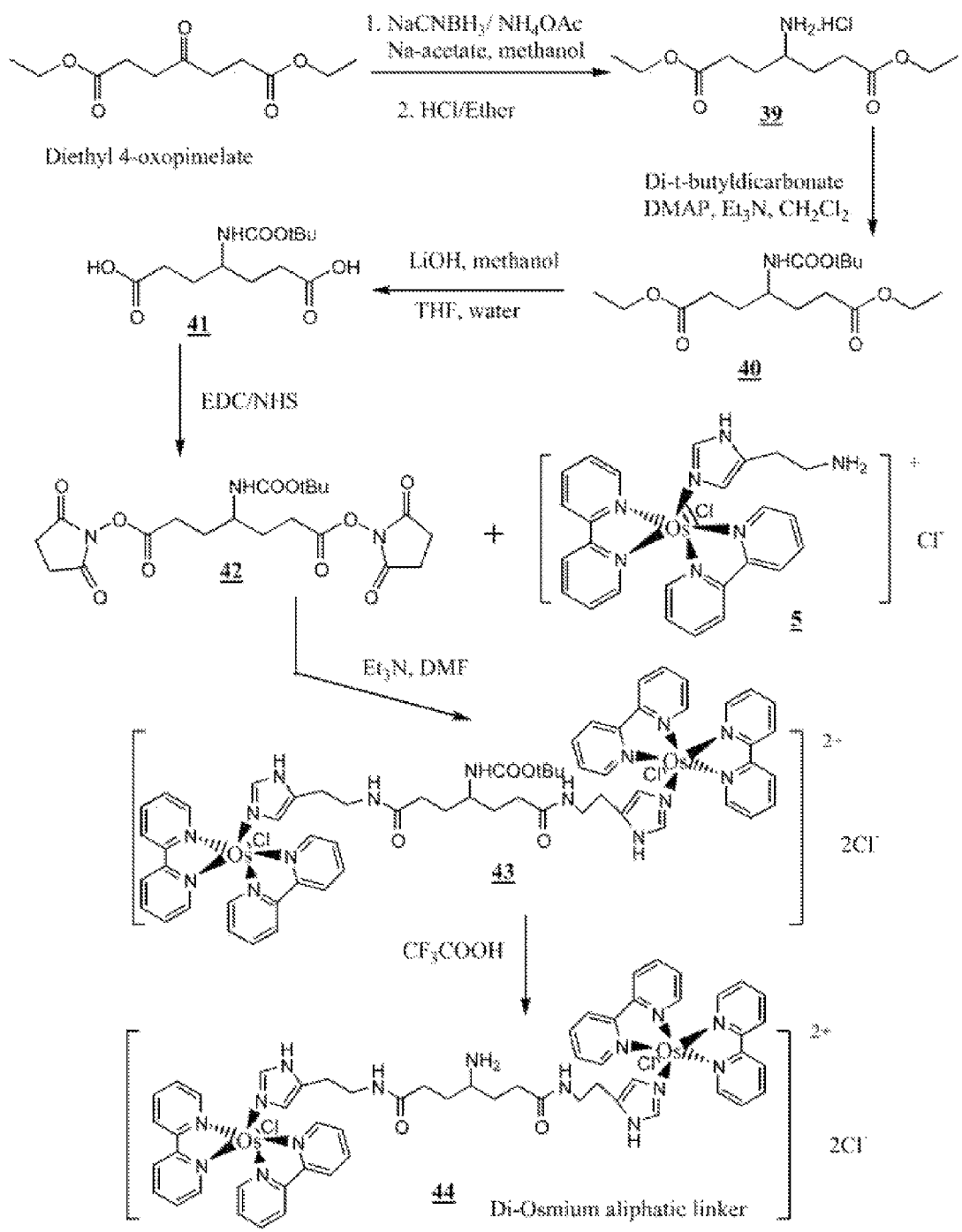
FIG. 29 illustrates a synthetic scheme for the preparation of a di-osmium electrochemical label with an aliphatic linker in accordance with the present invention.

The synthesis scheme of osmium methotrexate conjugate is shown in FIG. 24.

In one embodiment, the invention uses multi-osmium mediators. It was discovered that the use of multi-osmium mediators improves the detection sensitivity in the assays. Syntheses of osmium drug conjugates with multiple osmium redox centers were designed. Multi-functionalized aliphatic and aromatic linkers were designed to couple to osmium mediator amine with an additional different protected functionality. These mono-protected multi-osmium labels were deprotected and can be used to couple to drugs or other analytes of interest. As an example, a di-osmium THC-1 conjugate was prepared as shown in FIGS. 25-28. Thus, 3,5-dihydroxy benzyl alcohol was reacted with suitably protected halo alkylating reagent, most preferably t-butyl bromo acetate in the presence of a base, most preferably potassium carbonate to give disubstituted product of compound 22. The benzyl alcohol functionality of compound 22 was converted to a mesylate group followed by conversion to an azido group through a series of substitution reactions. The azide group of compound 24 was converted to an amino functionality by hydrogenation followed by protection as a trifluoroactamido group providing compound 26. The t-butyl ester functionalities were removed by treatment with trifluoroacetic acid to provide the corresponding diacid compound 27. This was converted to diacid chloride and reacted with osmium histamine amine of compound 5 to give the desired di-osmium aromatic linked mono-trifluoroacetamide (compound 29). A monosubstituted product was also isolated (compound 30) and evaluated for comparison purposes in the detection sensitivity measurement for electrochemical assay. The trifluoroacetamido group of compound 29 can be removed under basic conditions, most preferably aqueous potassium carbonate to give diosmium mediator 31 which can be coupled to an antigen (i.e. drug derivative; see FIG. 28) with the proper activating group.

Similarly a di-osmium complex with an aliphatic linker was also prepared. The aliphatic linker can be coupling to a suitably activated antigen (e.g. drug derivative) as shown in FIG. 30.

Figure 30:
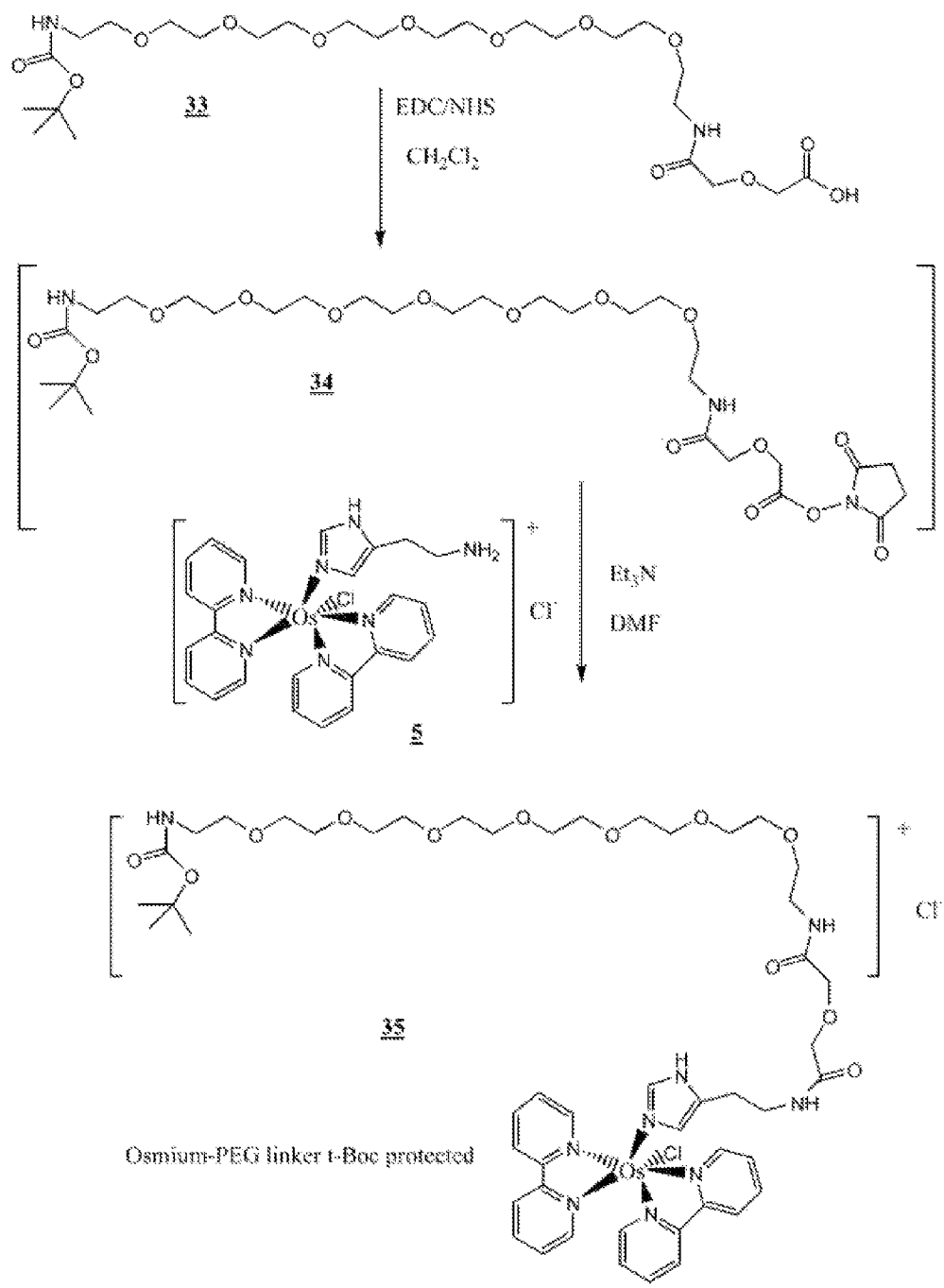
FIGS. 30 and 31 illustrate a synthetic scheme for the preparation of an osmium-PEG (linker) electrochemical label in accordance with the present invention.
Figure 31:
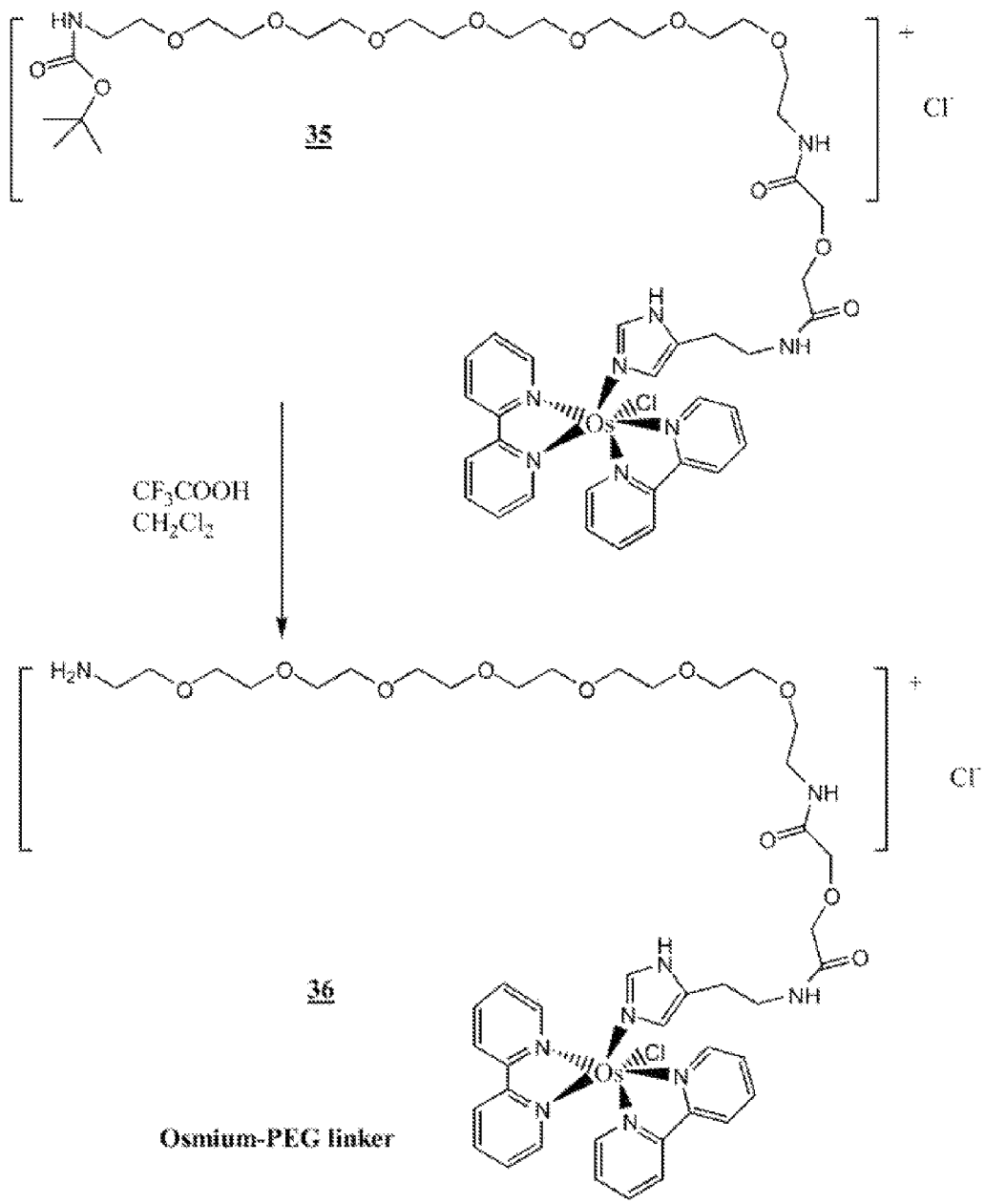
Figure 32:
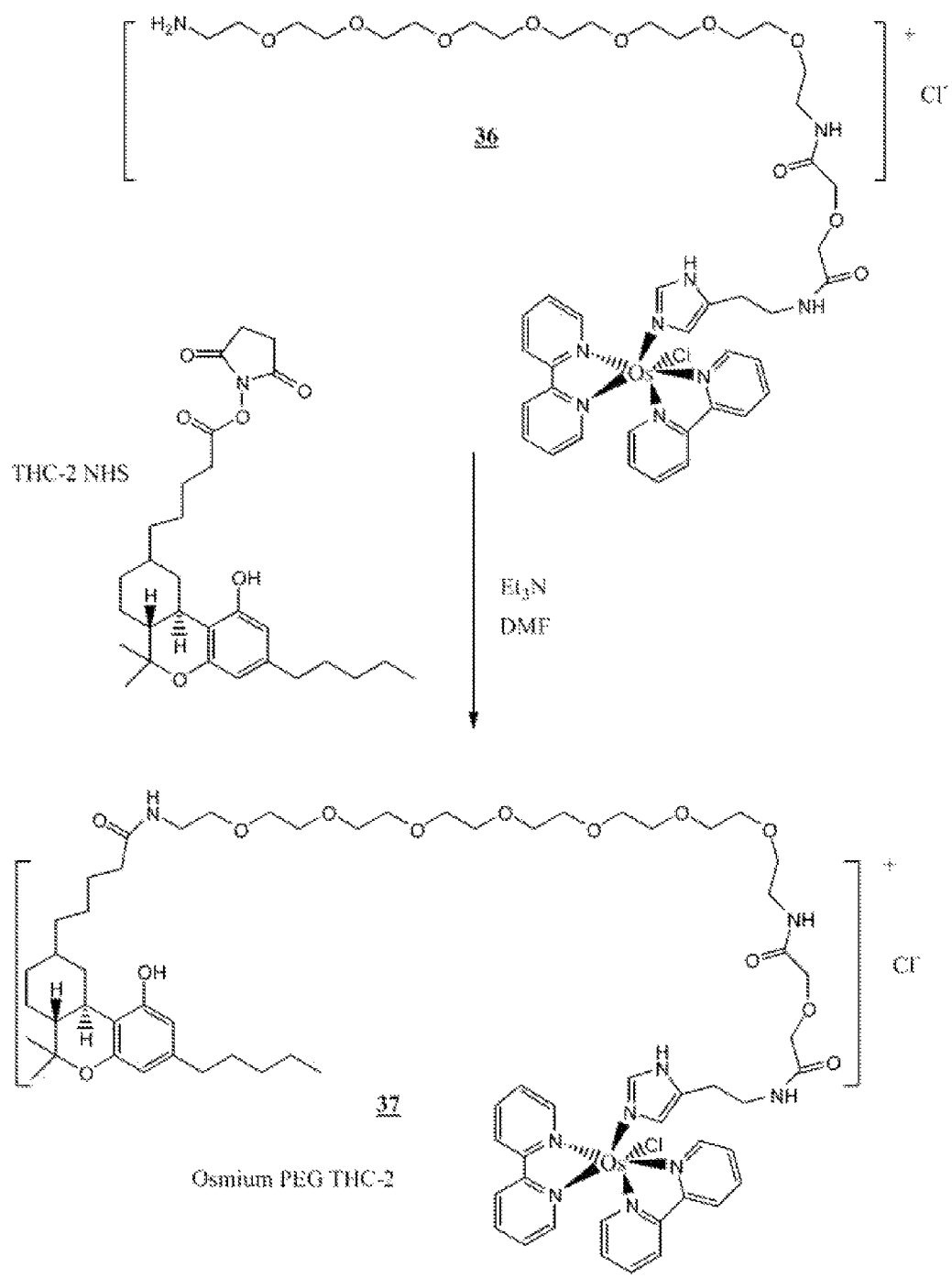
FIG. 32 illustrates a synthetic scheme for the preparation of an osmium PEG THC-2 conjugate in accordance with the present invention.

In another embodiment of the invention an osmium complex with a hydrophilic linker was prepared as shown in FIGS. 30-32. The osmium histamine mediator with hydrophilic linker has been suggested to overcome assay development difficulties seen with the hydrophobic analytes such as THC. A commercially available hydrophilic linker with proper functionalities is available (compound 33). This PEG linker has a protected amino functionality and a free carboxylic acid. The acid group of the PEG linker can be converted to an activated ester, preferably a N-hydroxysuccinimide ester and can be coupled to osmium histamine amino derivative (compound 5) in the presence of a base, preferably triethylamine to give compound 35. The t-BOC functionality of compound 35 was removed under acidic conditions, preferably using trifluoroacetic acid. The free amino group of the osmium PEG linker (compound 36) can be reacted with an activated ester linked drug, as example, THC-2-NHS (compound 16) to give the osmium-PEG-THC conjugate (compound 37).

Figure 33:
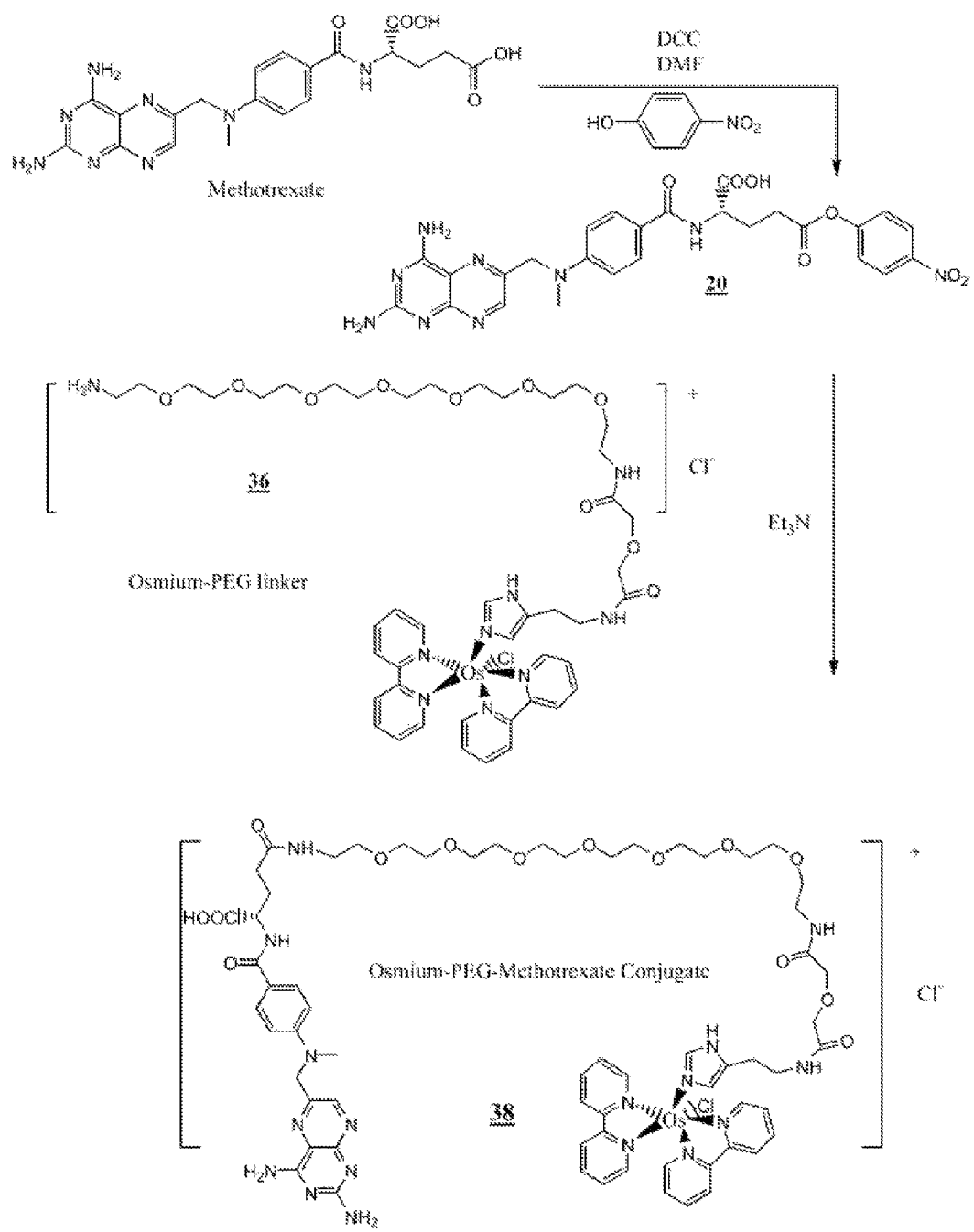
FIG. 33 illustrates a synthetic scheme for the preparation of an osmium PEG methotrexate conjugate in accordance with the present invention.

Osmium-PEG linker (compound 36) was coupled to methotrexate according to scheme shown in FIG. 33.

Figure 34:
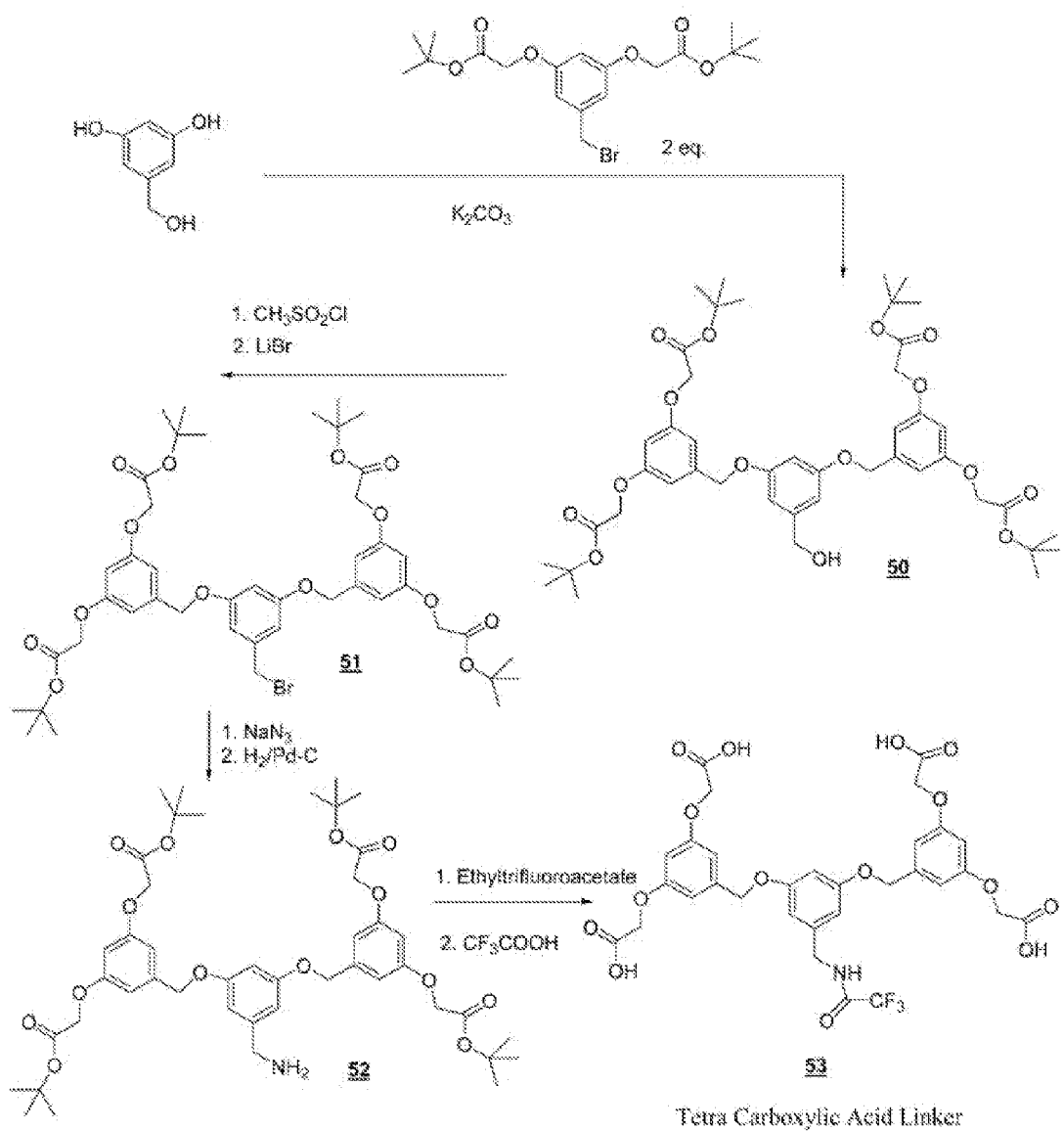
FIG. 34 illustrates a synthetic scheme for the preparation of a tetra carboxylic acid linker group in accordance with the present invention.
Figure 35:
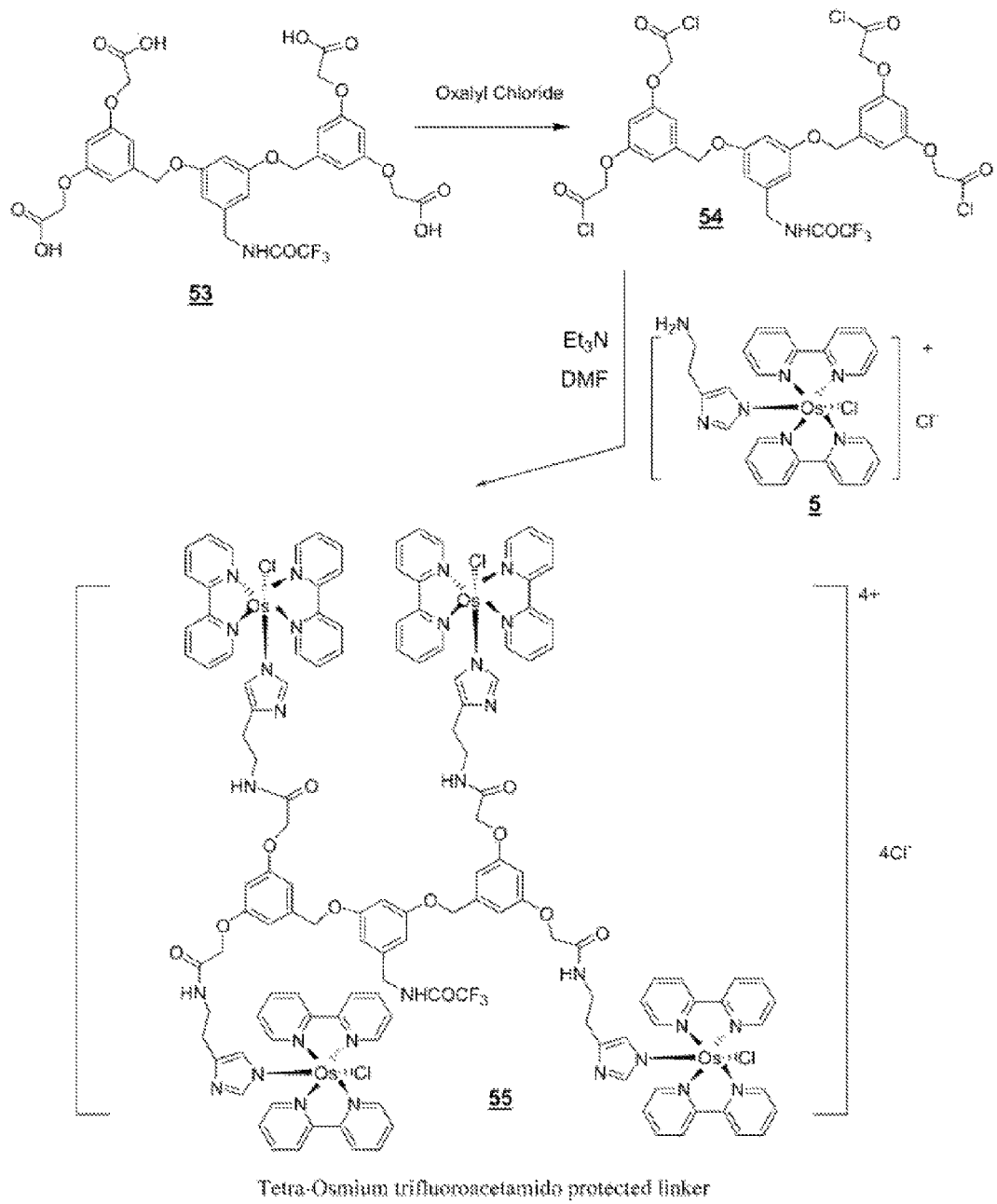
FIG. 35 illustrates a synthetic scheme for the preparation of the protected precursor of the tetra-osmium trifluoroacetamido electrochemical label in accordance with the present invention.
Figure 36:
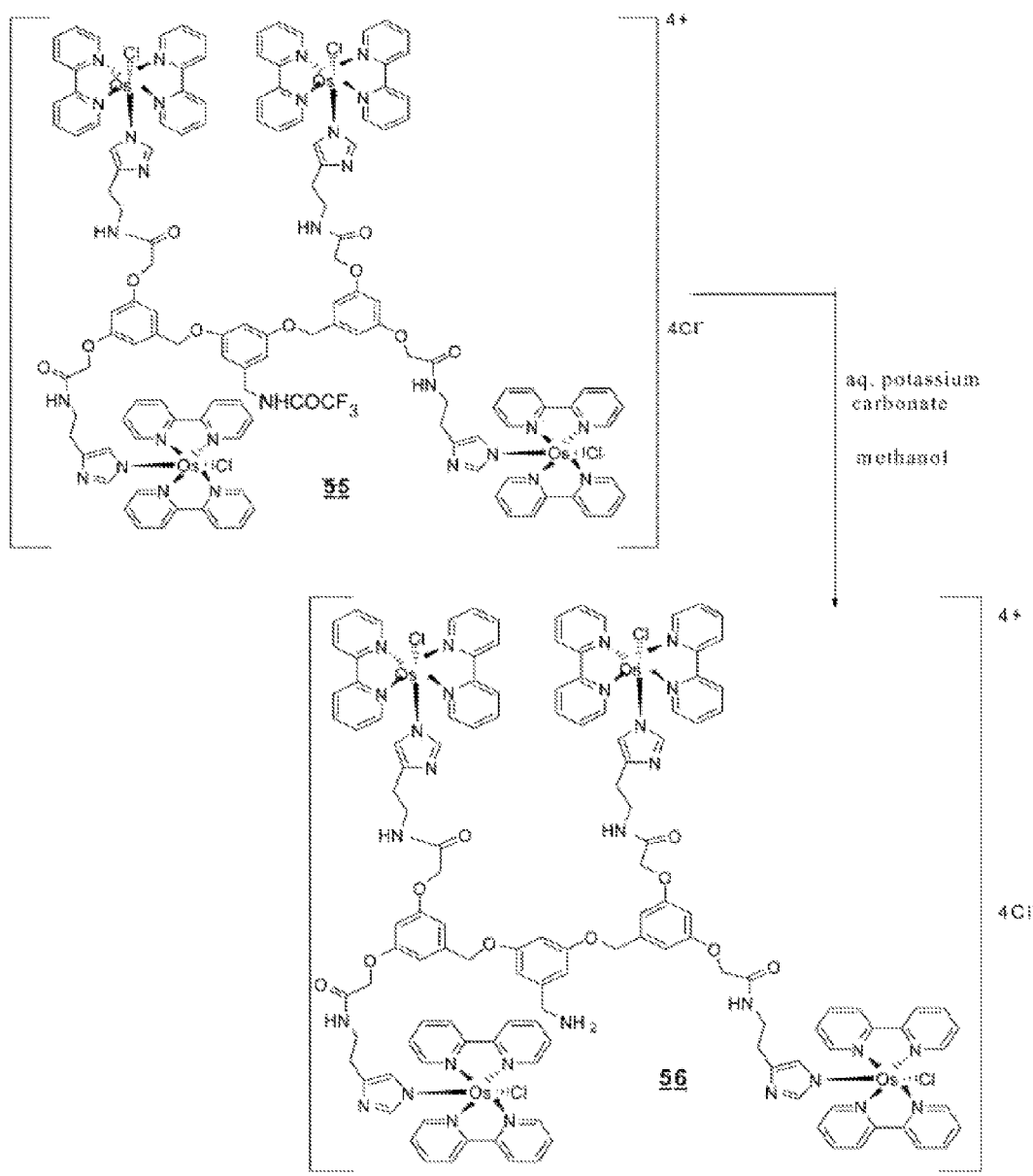
FIG. 36 illustrates a synthetic scheme for the deprotection of the tetra carboxylic acid linker of a tetra-osmium electrochemical label in accordance with the present invention.

FIGS. 34-36 illustrate a synthetic scheme to prepare a tetra osmium label. The intermediate bromo derivative, compound 23 can be reacted with 3,5-dihydroxybenzyl alcohol in the presence of a base to give the corresponding di-substituted product (compound 50). The benzyl alcohol group of compound 50 can be converted to the corresponding amine, compound 52, according to the similar procedure described above. The amine group can be protected using a suitable protecting group, most preferably a trifluoroacetamido group and t-butyl ester groups, which can later be removed under acidic conditions. The resulting tetra carboxylic acid functionalities of compound 53 can be converted to the corresponding acid chloride and can be coupled to the osmium histamine amine of compound 5 to give tetra-osmium aromatic label with trifluoroacetamido protected amine. The amino group can be released under basic conditions and the resulting compound 56 can be reacted with suitably activated antigen (e.g. drug derivatives) to give the antigen-tetra-osmium conjugate.

Figure 37:
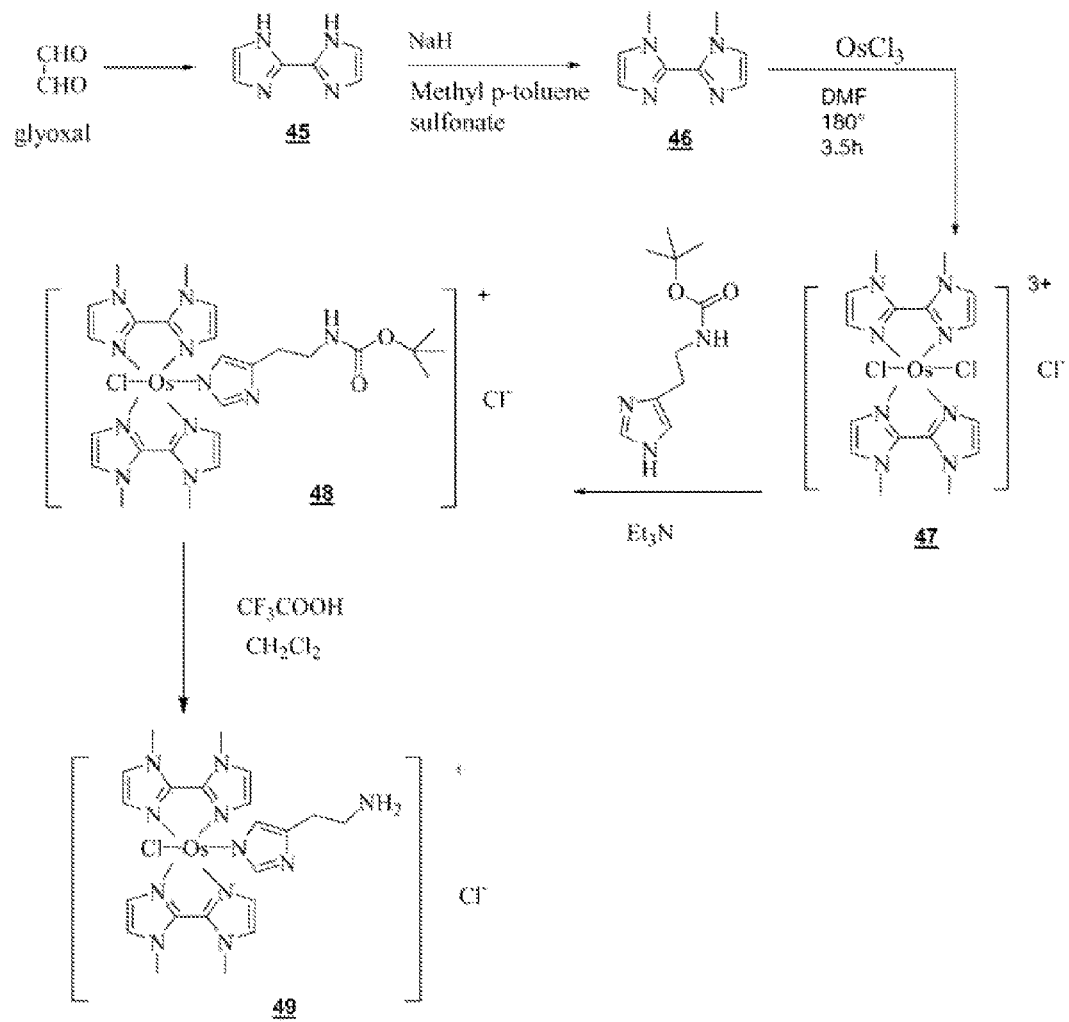
FIG. 37 illustrates a synthetic scheme for the preparation of an osmium (dimethyl biimidazole)$_2$ histamine linker or electrochemical label in accordance with the present invention.

In another embodiment of the invention, the synthesis of an osmium di-biimidazole histamine compound is described. This compound was developed to have a low redox potential to avoid potential interferents from undesirable oxidizable species that may also be in the sample such as ascorbic acid. The synthesis of di-biimidazole is shown in FIG. 37.

Thus glyoxal is reacted with ammonia to give biimidazole (compound 45). Dimethyl derivative of compound 45 can be reacted with methyl p-toluene sulfonate in the presence of a base, preferably sodium hydride to give compound 46. This can be reacted with osmium trichloride in DMF at 180° C. to give osmium di-biimidazole dichloride (compound E). The coupling of compound 47 and histamine t-BOC (compound 4) in the presence of a base, preferably triethylamine provides compound 48. The t-BOC group of compound 48 can be removed under acidic conditions, preferably using trifluoroacetic acid to give compound 49. The free amino group of osmium di-biimidazole histamine (compound 49) can be coupled to activated ester of drug derivative to provide drug-osmium di-biimidazole histamine conjugates.

The osmium di-biimidazole histamine (compound 49) exhibited a low redox potential $E_{1/2}$~540 mV vs Ag/AgCl. Mediators with low potentials are also necessary for multi analyte measurements in as described in U.S. Pat. No. 6,294, 062. In this case multiple electrochemical labels or mediators are needed each with different redox potentials spaced to allow each electrochemical label to be independently addressed.

Example 1

Electrochemical Assays of an Osmium-Theophylline Conjugate

An Os-theophylline conjugate was prepared as illustrated in FIG. 20. This redox reversible conjugate was evaluated with a series of electrochemical measurements designed to develop an assay response for theophylline. IDA microelectrodes were fabricated as described herein using photolithographic techniques. The IDAs included gold electrode structures with 50 finger pairs each having a width (W) of about 21 μm and a gap ($W_g$) of 10, 15, and 21 μm and length (b) of 6 mm. Each IDA also contained two additional gold electrode regions for use as a counter and reference electrode. The electrochemical measurements were performed using a CH Instruments bipotentiostat model 802A or 832A. Bipotentiostatic amperometric measurements were made for IDA amplification and a single potential amperometric technique was used for enzyme amplification. Each measurement required about 20 μL sample pipette onto the electrode when using an external reference electrode or 5-10 μl with an internal reference electrode of Ag/AgCl ink and a capillary roof over the active electrode structures.

Figure 38:
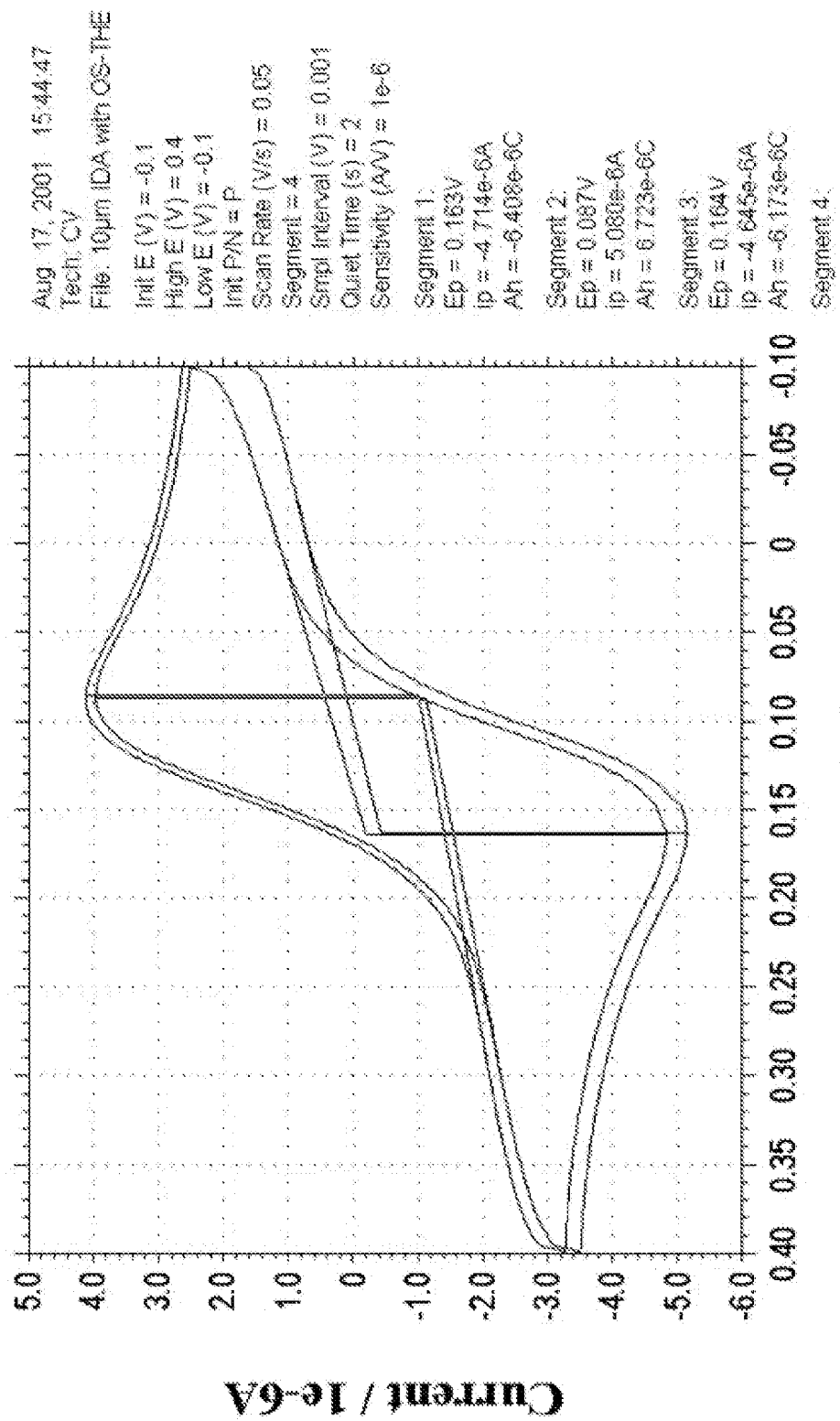
FIG. 38 is a CV spectrum of an osmium-theophylline conjugate electrochemical label.

FIG. 38 shows a CV of the osmium-theophylline conjugate on a 10 μm gap ($W_g$), 21μm (W) IDA electrode with 50 finger pairs. The CV shows symmetrical oxidation and reduction peaks and an $E_{1/2}$ of about 125 mV vs. Ag/AgCl. From this the proper anodic and cathodic potentials can be selected for amperometric measurements and controlled with a bipotentiostat.

Figure 39:
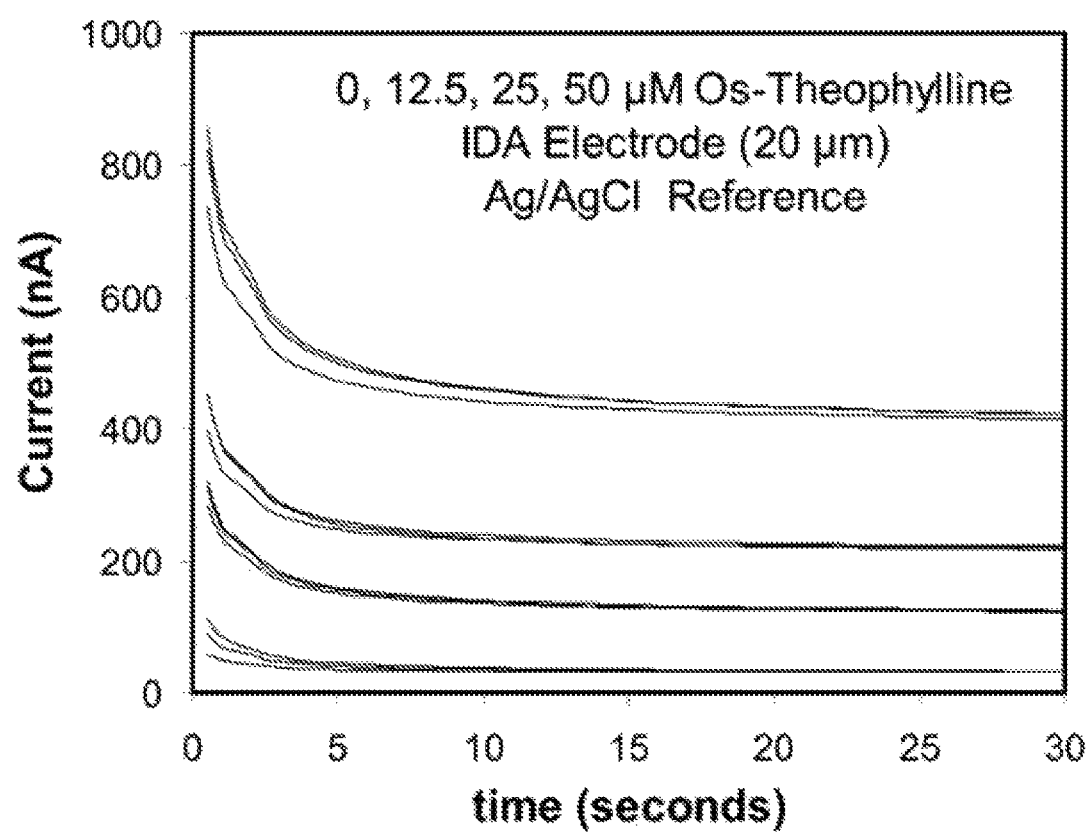
FIG. 39 is a plot illustrating the steady state response of the osmium-theophylline conjugate electrochemical label.

FIG. 39 illustrates the oxidative steady state response to the osmium-theophylline conjugate measured at different concentrations on a 21 μm gap ($W_g$), 21 μm (W) IDA electrode with 50 finger pairs. A bipotentiostat was used at the proper anodic and cathodic potentials applied to WE1 and WE2. This graph illustrates that even this larger dimensioned IDA reach steady stated in a few seconds.

Figure 40:
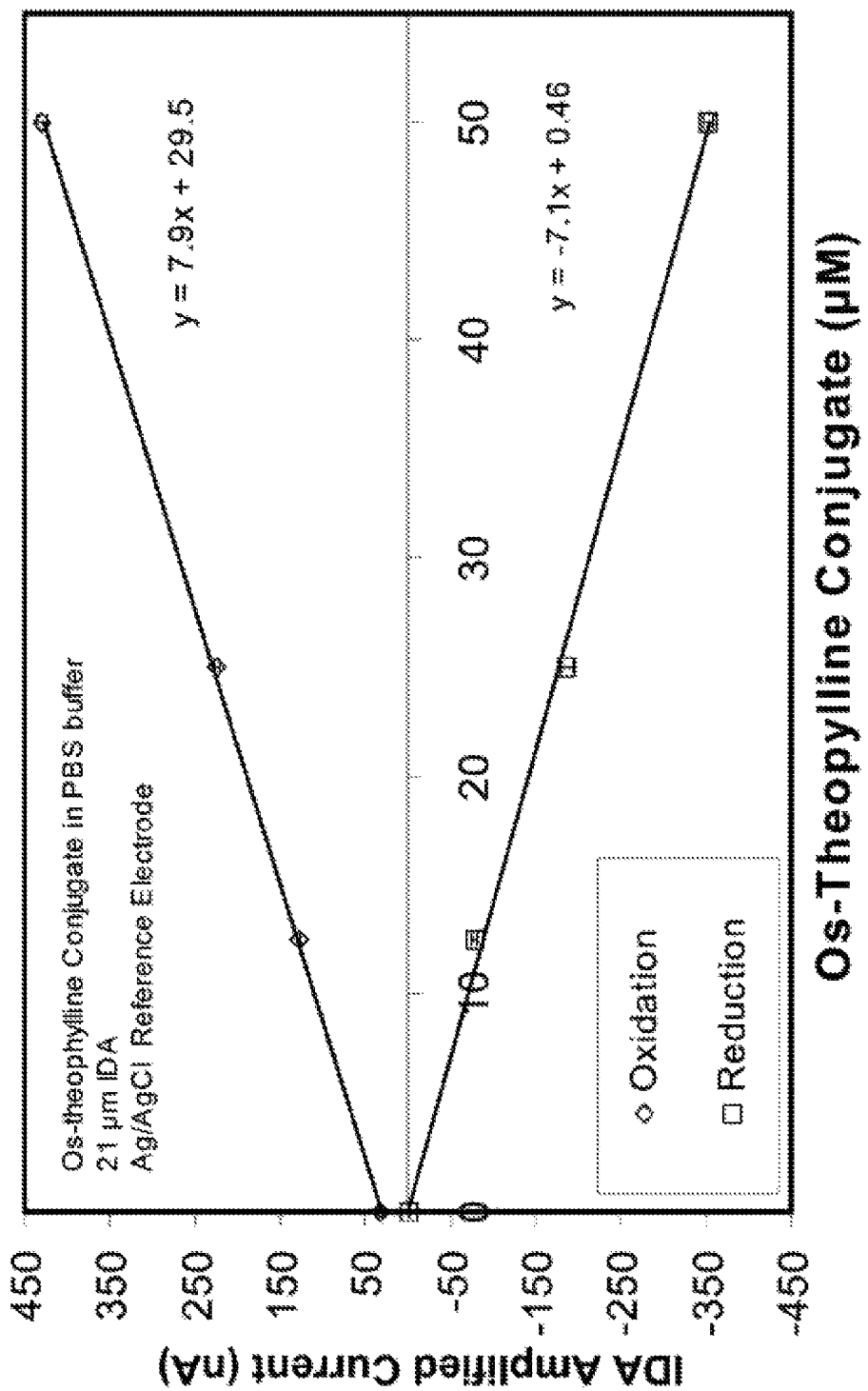
FIG. 40 is a plot of the dose response of the osmium-theophylline conjugate electrochemical label.

FIG. 40 illustrates a dose response curve of the osmium-theophylline conjugate at various concentrations on a 21 μm gap ($W_g$), 21 μm (W) IDA electrode with 50 finger pairs. The electrode potentials were controlled with a bipotentiostat. Again, it can be observed that the oxidation and reduction are approximately equal in absolute magnitude, which is indicative that no other species in the sample is interfering with the current measurement at the electrodes.

It will be observed that the dose response curves herein display a multimeter bias. The term "multimeter bias" refers to a bias in the data collected that is solely a result of the electrodes and instruments also being connected to a high impedance multimeter, in this case a Fluke 87 multimeter with an input impedance of 10 MOhm. For amperomenteric measurements including bipotentiostatically controlled amperometric measurements, the bias is a constant I=V/R where V is the applied potential in volts for each respective electrode and R=10 MOhm. For the applied potential of 0 mV vs. Ag/AgCl the bias would be 0 nA but for the applied potential of 200 mV the bias would be 20 nA.

Figure 41:
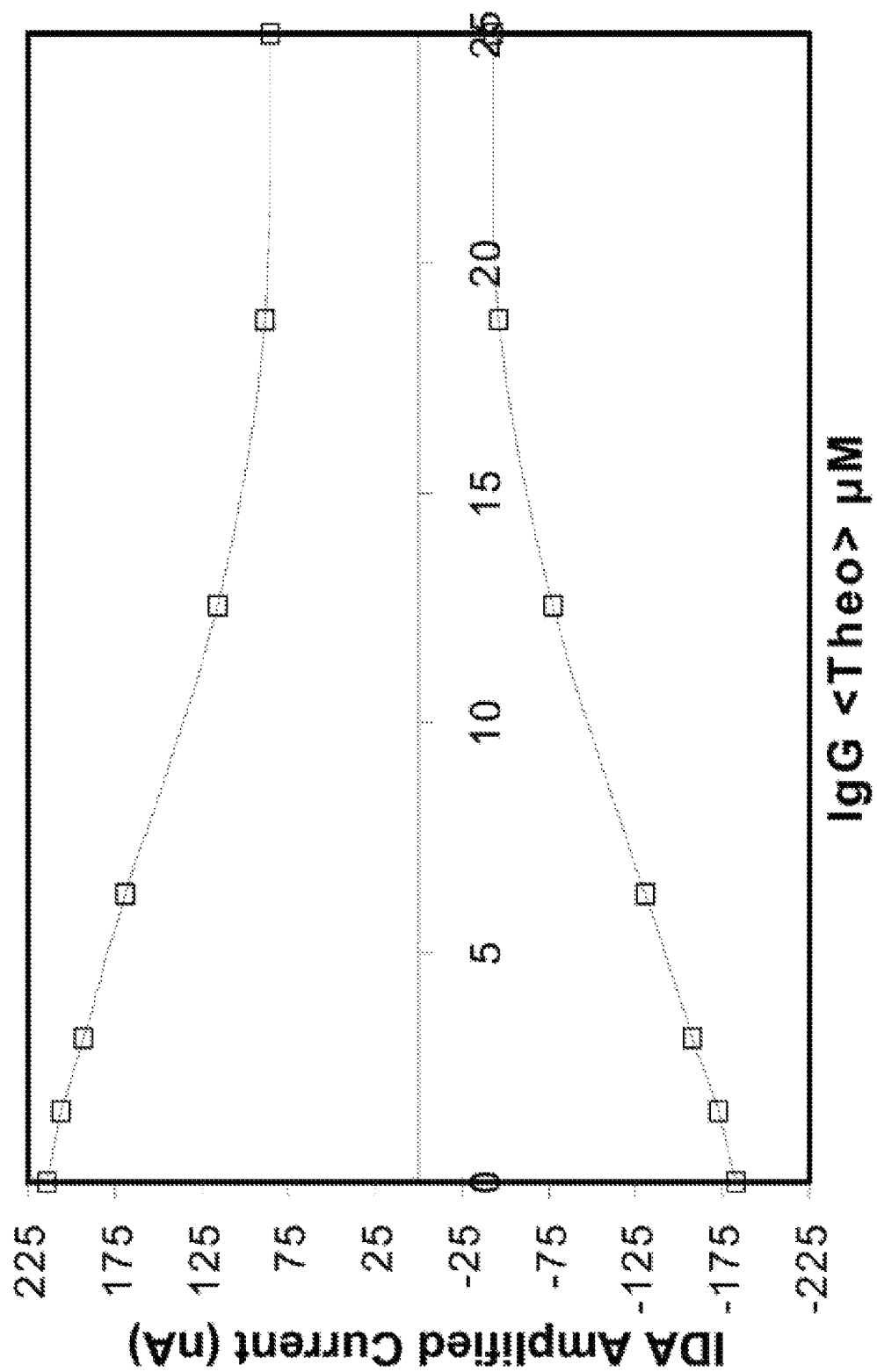
FIG. 41 is a plot of the antibody inhibition of the osmium-theophylline conjugate electrochemical label.

FIG. 41 is a plot illustrating the inhibition of the conjugate response with increasing concentrations of the antibody in solution. In the example, the osmium-theophylline conjugate concentration was maintained at about 25 µM, while the concentration of the antibody in solution increased. From the inhibition curve, it was determined that for this example, the optimal conjugate to antibody ratio is 2:1 since the slope of the inhibition curve decreases significantly when antibody concentration increases further. This corresponds to the stoichiometric ratio of 1:1 since antibodies are bivalent. It should also be noted that the response also shows a multimeter bias.

Figure 42:
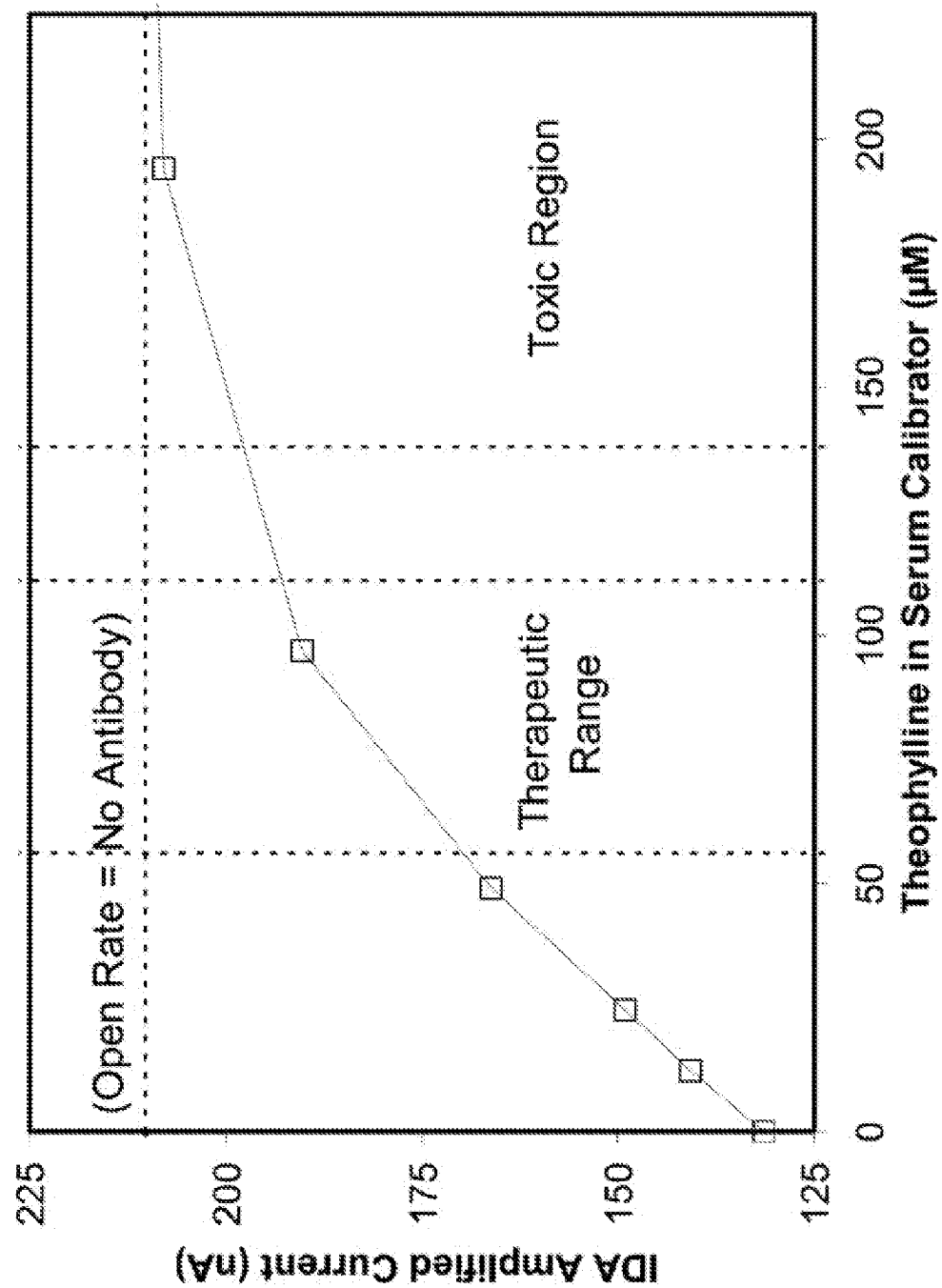
FIG. 42 is a plot of a theophylline assay response in a serum matrix.

FIG. 42 is a theophylline assay run in serum calibrators and plots the IDA amplified current obtained for the osmium-theophylline conjugate. The test was run with a osmium-theophylline conjugate concentration of about 25 µM and antibody concentration of about 12.5 µM while varying the concentration of theophylline. The assay has a broad assay range that spreads from below the therapeutic range to the toxic region.

Example 2

Electrochemical Assays of an Osmium-Amphetamine Conjugate

An Os-amphetamine conjugate (10) was prepared as illustrated in FIG. 19. This redox reversible conjugate was evaluated in a series of electrochemical assays. Interdigitated array (IDA) microelectrodes were fabricated as described herein using photolithographic techniques. Each IDA contained 50 pairs of "fingers" each finger had a width of 21 µm and a gap width between the fingers of 15 µm. The electrochemical measurements were performed using a CH Instruments bipotentiostat model 802A or 832A. Bipotentiostatic amperometric measurements were made for IDA amplification and a single potential amperometric technique was used for enzyme amplification. Each measurement required about 20 µL sample pipette onto the electrode when using an external reference electrode or 5-10 µl with an internal reference electrode of Ag/AgCl ink and a capillary roof over the active electrode structures.

Figure 43:
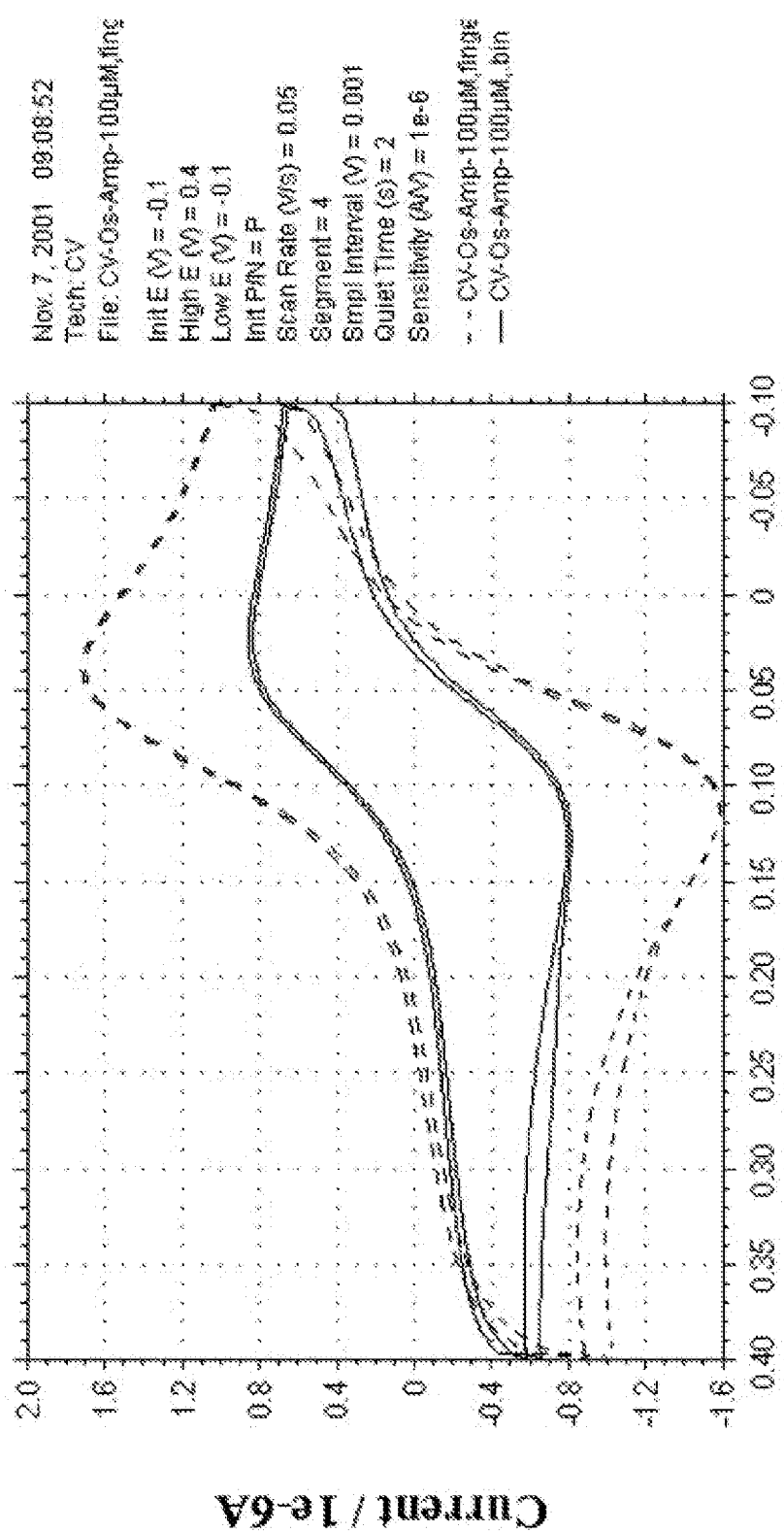
FIG. 43 is a CV spectrum of an osmium-amphetamine conjugate electrochemical label.

FIG. 43 shows a cyclic voltammogram of 100 µM Os-amphetamine conjugate prepared in a PBST solution. The figure shows a CV with a single finger set and when both finger set are shorted together and used as the working electrode. The CV shows symmetrical oxidation and reduction peaks and an $E_{1/2}$ of about 125 mV vs. Ag/AgCl. From this the proper anodic and cathodic potentials can be selected.

Figure 44:
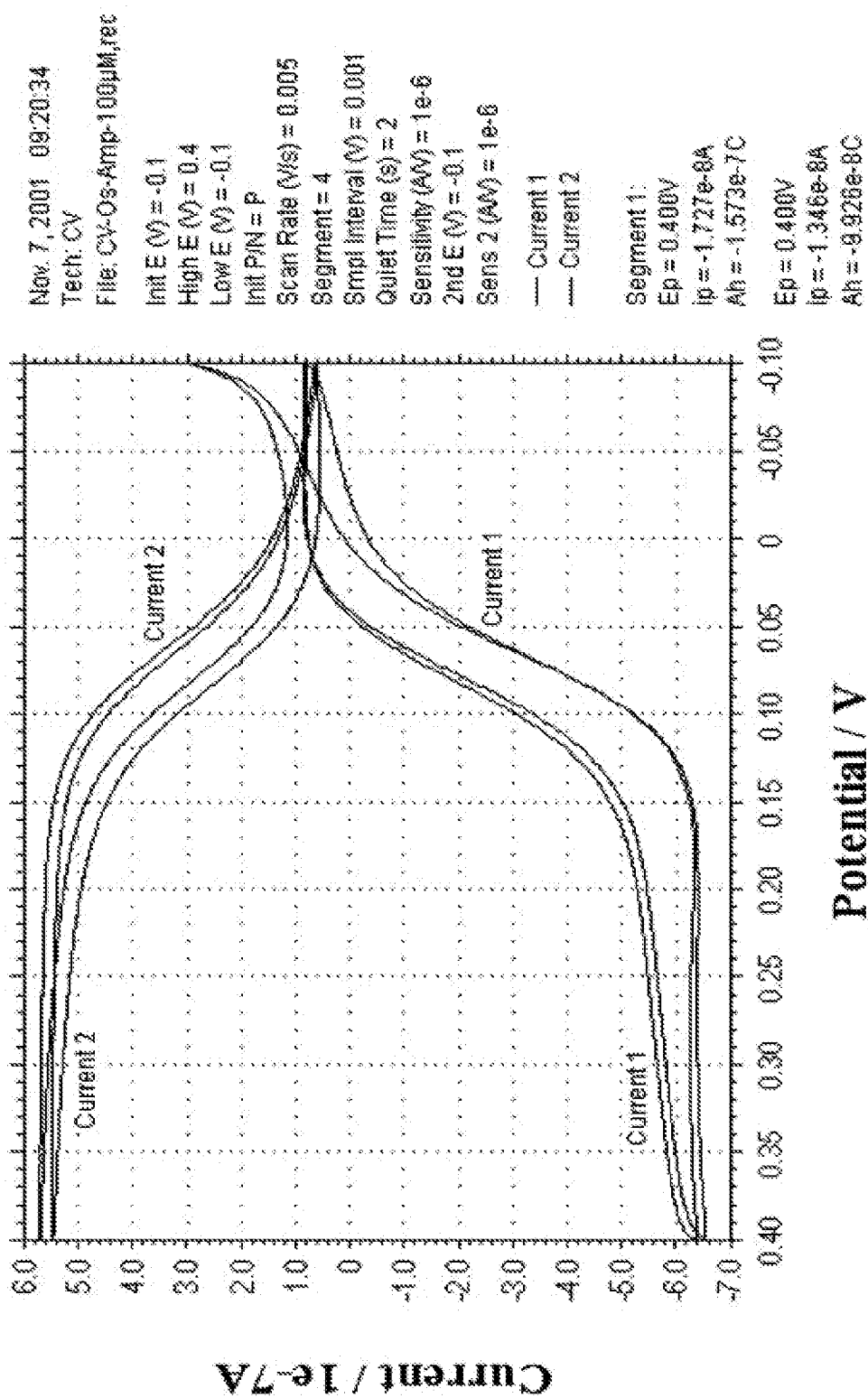
FIG. 44 is a recycling CV of the osmium-amphetamine conjugate electrochemical label.

FIG. 44 is a recycling CV of 100 µM osmium-amphetamine conjugate on a 15 µm IDA electrode using a bipotentiostat to control the potentials. WE1 was scanned from −100 to 400 mV while WE2 was held constant at −100 mV. The CV shows the mediator undergoing redox recycling. The CV shows a steady-state response of about 600 nA. or 6 nA/µM. The recycling CV shows that the oxidation and reduction current achieve have equal and opposite magnitudes. The current is amplified due to recycling. To measure the recycling CV the WE2 was fixed at a reduction potential of −100 mV and WE1 was scanned between a reduction potential of −100 mV and an oxidation the potential of 400 mV. Recycling occurs when one finger set is poised for oxidation and the other for reduction. Generally, as long as the sweep rate is not too fast, the magnitude of the current is not proportional to sweep rate. This differs from a normal CV where the response increased with sweep rate.

Figure 45:
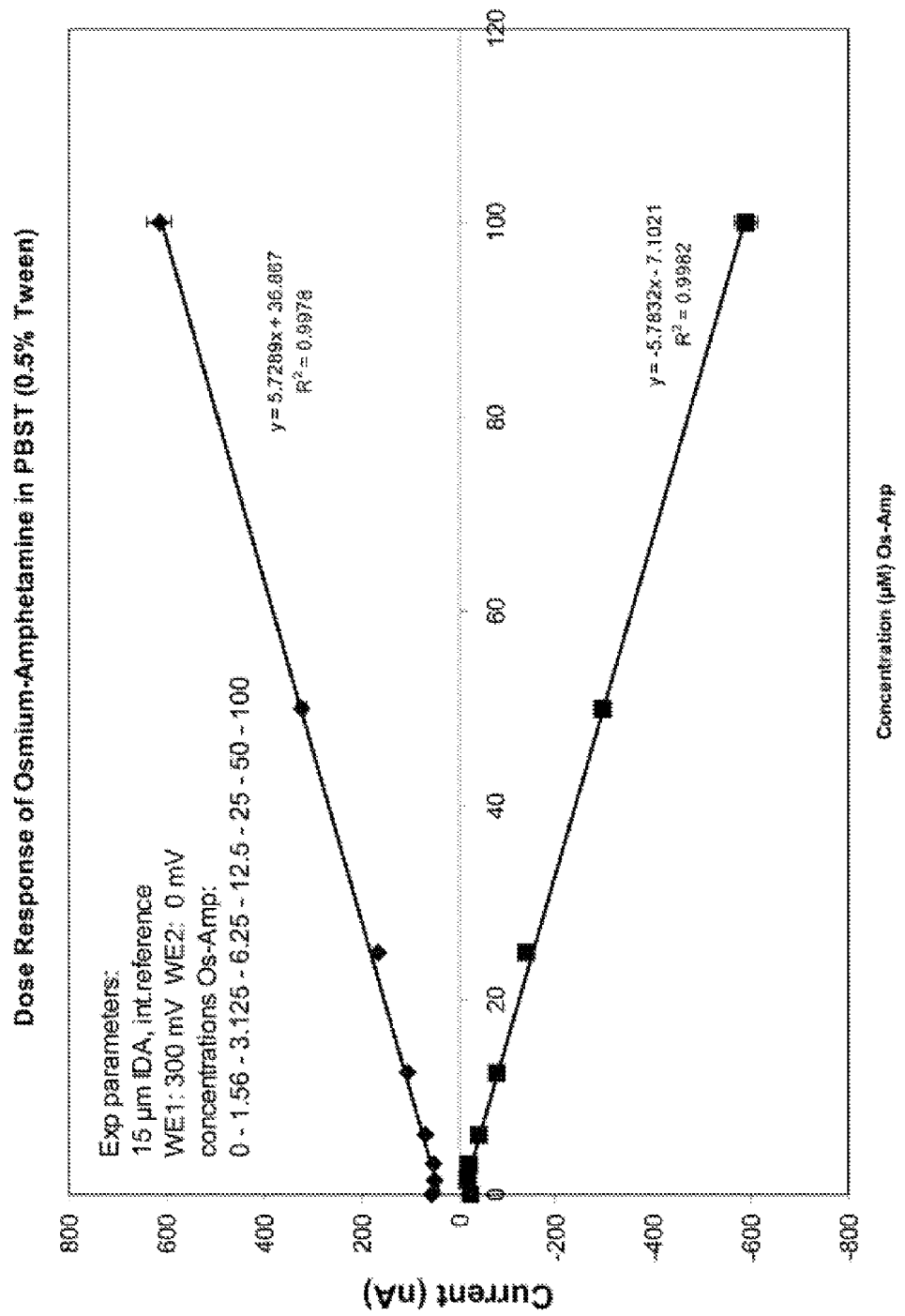
FIG. 45 is a plot of the conjugate response of osmium-amphetamine electrochemical label.

FIG. 45 is an osmium-amphetamine conjugate dose response on a IDA with a 15 µm gap and 21 µm width. The osmium-amphetamine conjugate was prepared in PBST at concentrations from 0 µM to 100 µM. A CH Instruments bipotentiostat was used to make the measurements. The current observed at both working electrode #1 and working electrode #2 was approximately equal in absolute magnitude and slope (assuming subtraction of the multimeter bias). The plot was generated using a 15 µm IDA with an internal Ag/AgCl reference electrode and WE1=300 mV and WE2=0 mV.

The inhibition of the osmium-amphetamine conjugate was also evaluated using a bipotentiostat on an IDA with a 15 µm gap and 21 µm width. The electrodes were poised where WE1=250 mV and WE2=−150 mV vs. an internal reference electrode. The Os-amphetamine conjugate was mixed with varying concentrations of a monoclonal amphetamine antibody from Roche [<AMPH>M-2.17.22>] and a inhibition curve the optimal ratio of ratio of conjugate to antibody was determined to be the stoichiometric ratio of 2:1. This corresponds to the stoichometric ratio since the antibody is bivalent. This ratio was then used to demonstrate an amphetamine assay utilizing IDA amplification.

Figure 46:
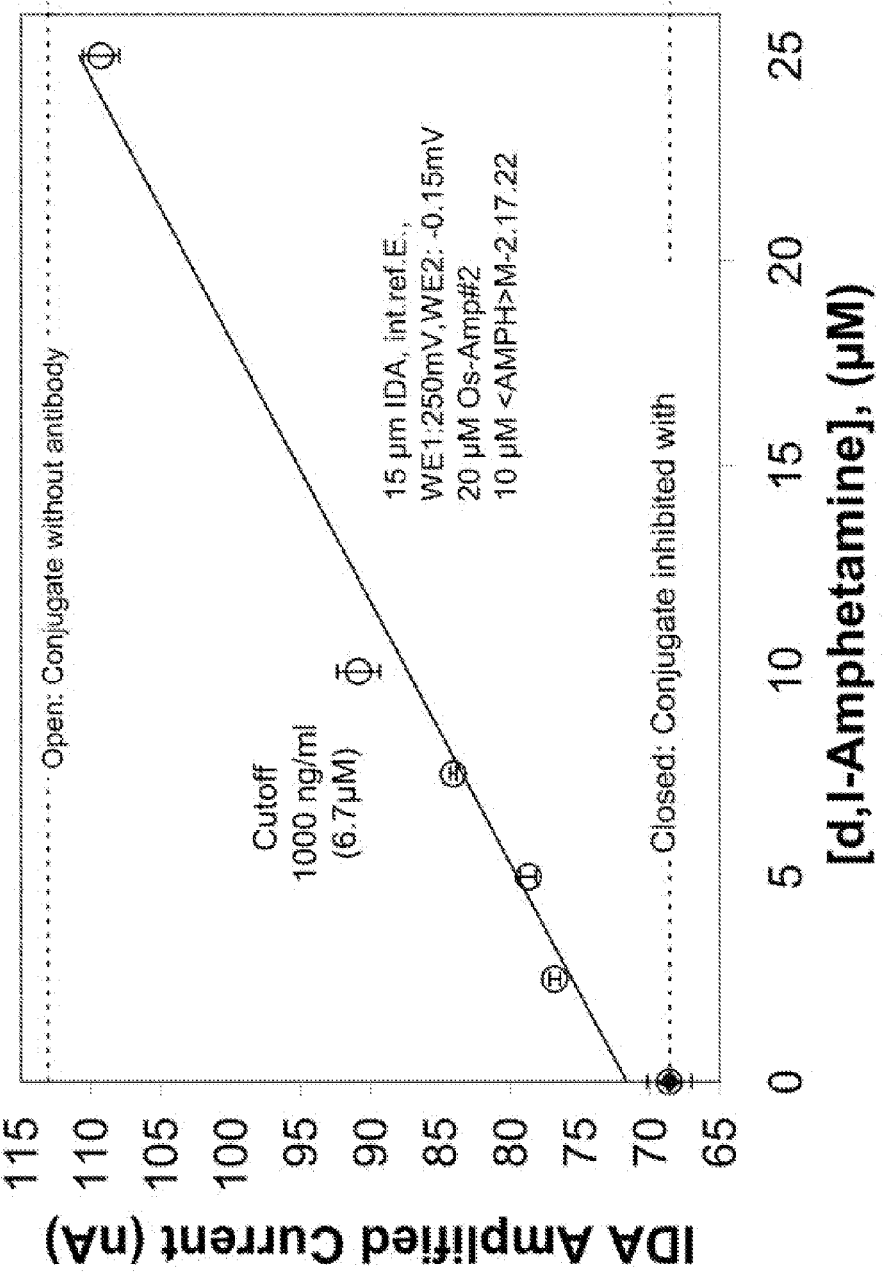
FIG. 46 is an assay curve for amphetamine in PBST obtained in the presence of the osmium-amphetamine electrochemical label.

FIG. 46 shows a plot of an amphetamine assay. Varying concentrations of d,l-amphetamine drug were mixed with a fixed concentration of antibody followed by a fixed concentration of conjugate. The final solution matrix contained 20 µM osmium amphetamine conjugate, 10 µM antibody, and amphetamine concentrations between 0 and 25 µM. Each solution was mixed and immediately transferred onto an IDA electrode to measure the current response using a bipotentiostat. The measured oxidative and reductive current responses are plotted against the drug concentration to produce the assay dose response curve. The current response from the conjugate increased as more drug was added and bound antibody resulting in less conjugate inhibition. The assay dose response curve covers the range required for amphetamine drugs of abuse assay which has a SAMHSA mandated cutoff concentration of 1000 ng/mL or 6.7 µM. The amphetamine response was evaluated using a bipotentiostat on an IDA with a 15 µm gap and 21 µm width. The electrodes were poised where WE1=250 mV and WE2=−150 mV vs. an internal reference electrode.

Example 3

Osmium-Biotin Model System with 2 µm IDA

Interdigitated array electrodes were custom fabricated for Roche Diagnostics by Premitec, Inc., Raleigh, N.C. Each IDA contained 750 pairs of electrodes each 6 mm in length with a gap and width of 2 µm. The interdigitated region for these electrodes totaled 36 mm². This large dimension was selected based on practical considerations of achieving lower detection limits Instruments, especially a portable handheld bipotentiostat, have limitations as to the minimum currents that can be detected. At the time, an assumption was made that 1 nA would be the lowest current that would be measured for an assay due to noise considerations of a handheld device. Using this information along with predicted current responses, the dimensions of the electrodes were determined to allow a sizeable improvement in immunoassay sensitivity. In addition these electrodes were also fabricated to compare the calculated sensitivity to that actually observed to demonstrate that improved amplification as would be predicted by Equation 1.

An osmium-biotin conjugate (compound 57 shown below) was prepared according to procedures similar to as describe in U.S. Pat. No. 6,262,264

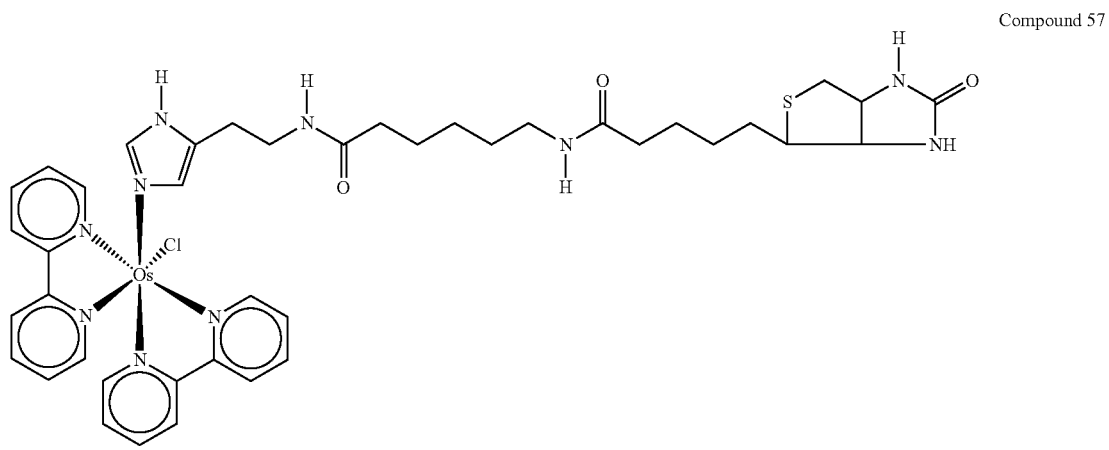

Compound 57

A microcentrifuge tube was charged with 20 μl of biotin in the following concentrations: 0, 1.25, 2.5, 3.75, 5, 7.5, and 10 μM. To each of these solutions were added 20 μL of 1.25 μM streptavidin and 40 μL PBST. To each solution, 20 μL of 5 μM streptavidin was added, mixed briefly (~2 s), and pipetted between the capillary space built on a 2 μM IDA electrode. A bipotentiostatic measurement was immediately initiated controlling WE1 at 250 mV and WE2 at 0 mV vs. Ag/AgCl.

Figure 47:
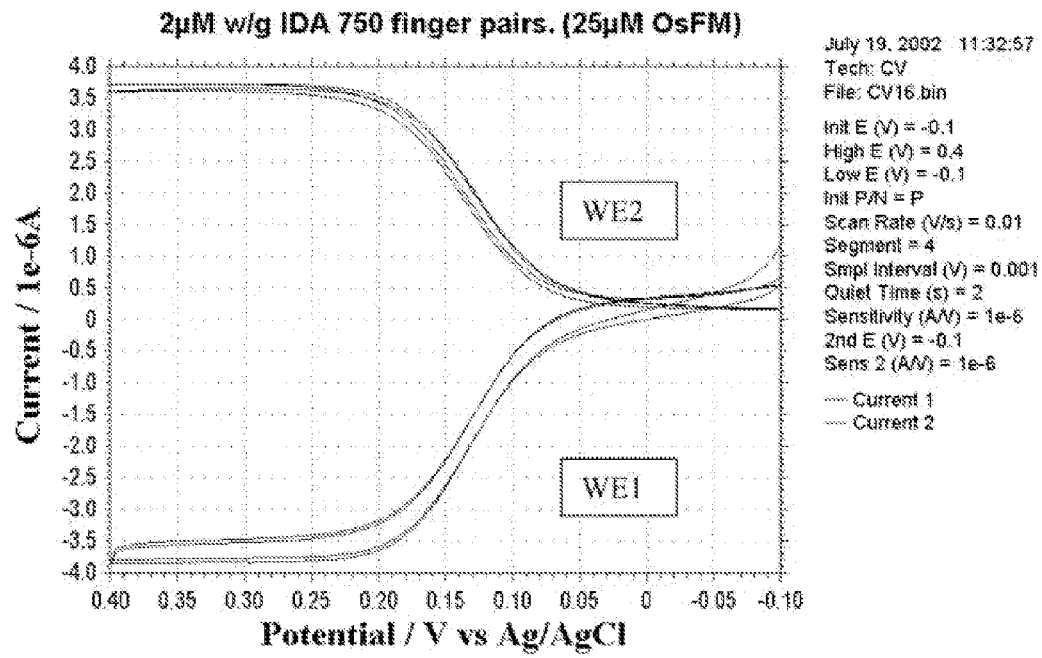
FIG. 47 is a recycling CV for bis(2,2'-bipyridyl)imidazole chloro osmium (III)dichloride label on a 2 μM gap/width interdigitated array electrode containing 750 interdigitated electrode pairs.

FIG. 47 shows the recycling cyclic voltamogram (CV) steady-state response obtained with 25 μM of osmium free mediator (bis(2,2'-bipyridyl)imidazole chloro osmium (III) dichloride) on a planar IDA electrode with 750 finger pairs with W and Wg of 2 μm. The recycling CV was run with WE1 being the generator scanned from −100 mV to 400 mV and WE2 the collector held at −100 mV. This response shows excellent amplification and efficiency with the steady-state response of about 3800 nA or 152 nA/μM.

Figure 48:
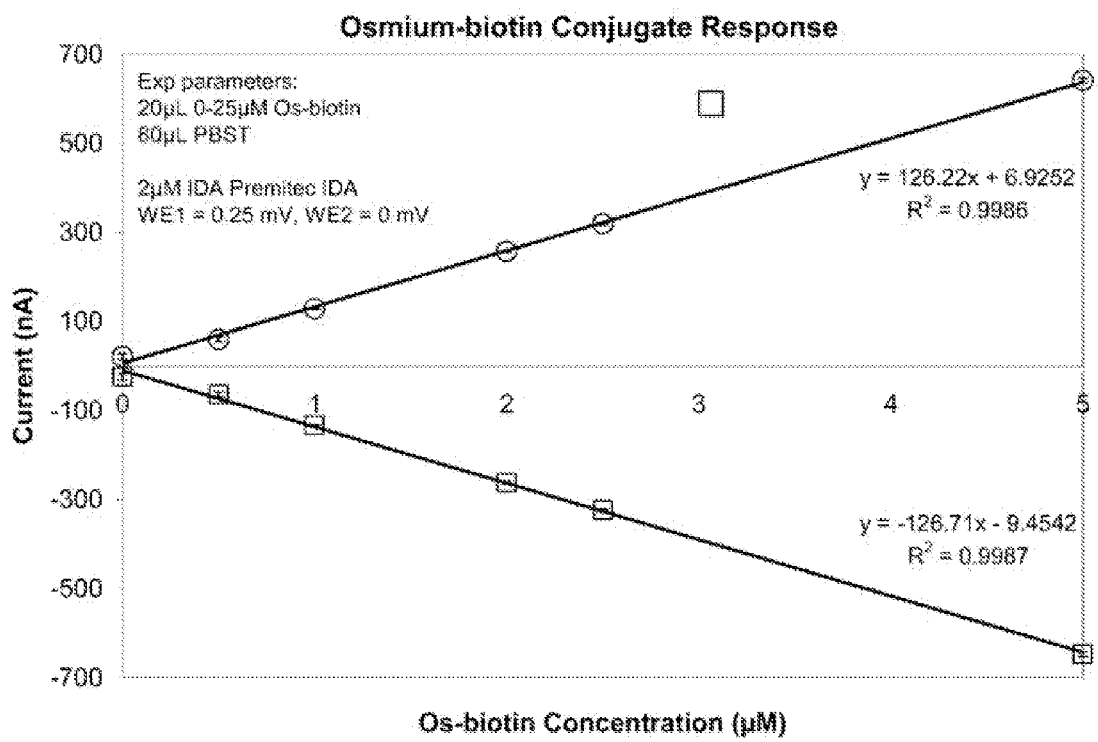
FIG. 48 is an osmium biotin conjugate dose response on a 2 μm IDA electrode.

FIG. 48 shows a dose response curve of the osmium biotin conjugate 0-5 μM on a planar IDA electrode with 750 finger pairs with W and $W_g$ of 2 μm. The measurements controlled WE1=250 mV and WE2=0 mV with a CHI Instruments bipotentiostat. The slope of the oxidation and reductive measurements are approximately equal and opposite indicating good redox recycling efficiency. The slope of about 126 nA/μM with the osmium biotin is a very good response only slightly less then the 152 nA/μM calculated for osmium free mediator from the CV of FIG. 47.

Figure 50:
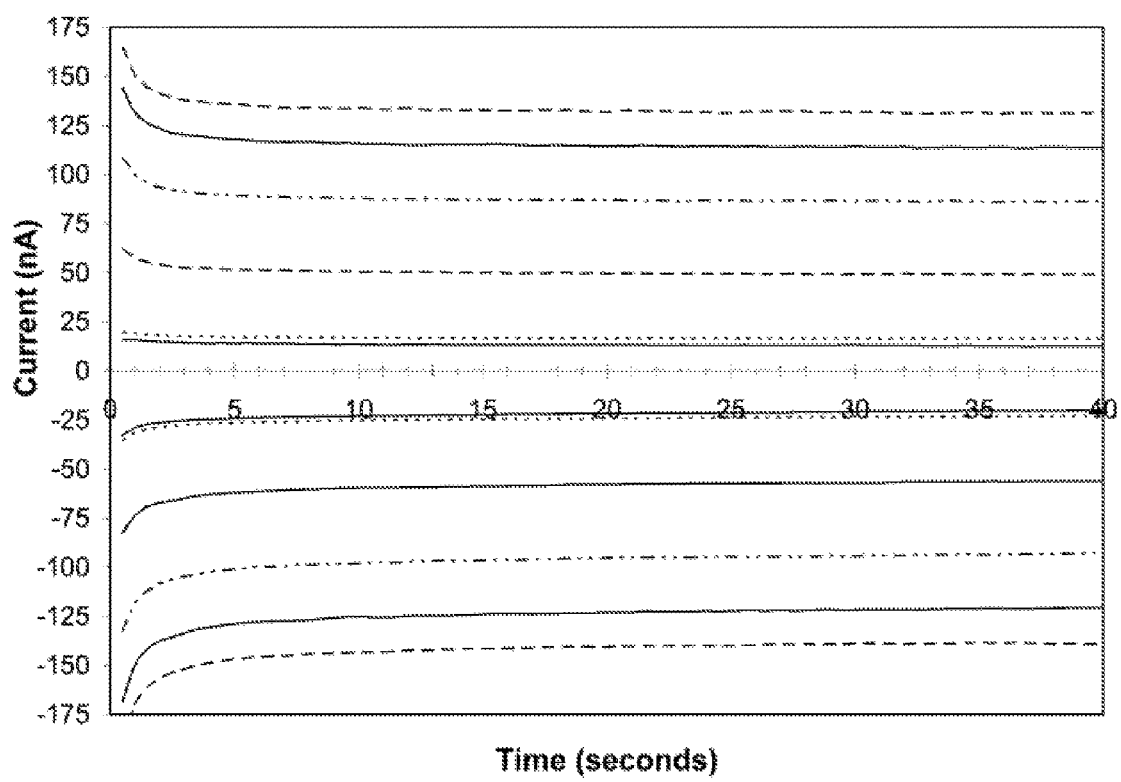
FIG. 50 is a plot of current vs. time of the steady-state response of representative concentrations of the biotin assay of FIG. 49.

Data was collected at 0.5 sec intervals for 40 seconds. The assay response was evaluated at several time points and giving similar results at all times including the 0.5 second time point. FIG. 49 shows the biotin assay response at time=0.5, 2, and 10 seconds. The assay reagents were selected for an assay range of 0-1 μM which was achieved. A typical plot showing a steady-state current vs. time is shown in FIG. 50. The data shows that a steady-state response is achieved almost instantaneously from the onset of the applied potentials. Steady-state is achieved when the oxidized and reduced species generated on respective electrodes are equal.

These results were collected using a 2 μM IDA electrode that was prepared at Premitec Inc, Raleigh, N.C. and was from wafer ID#0702HIDA1 . . . 14. The final assay concentrations were 1 μM of the osmium biotin conjugate, 0.25 μM streptavidin and biotin from 0-2 μM. This assay was performed using a CHI-802A bipotentiostat from CH Instruments, Austin, Tex.

Figure 51:
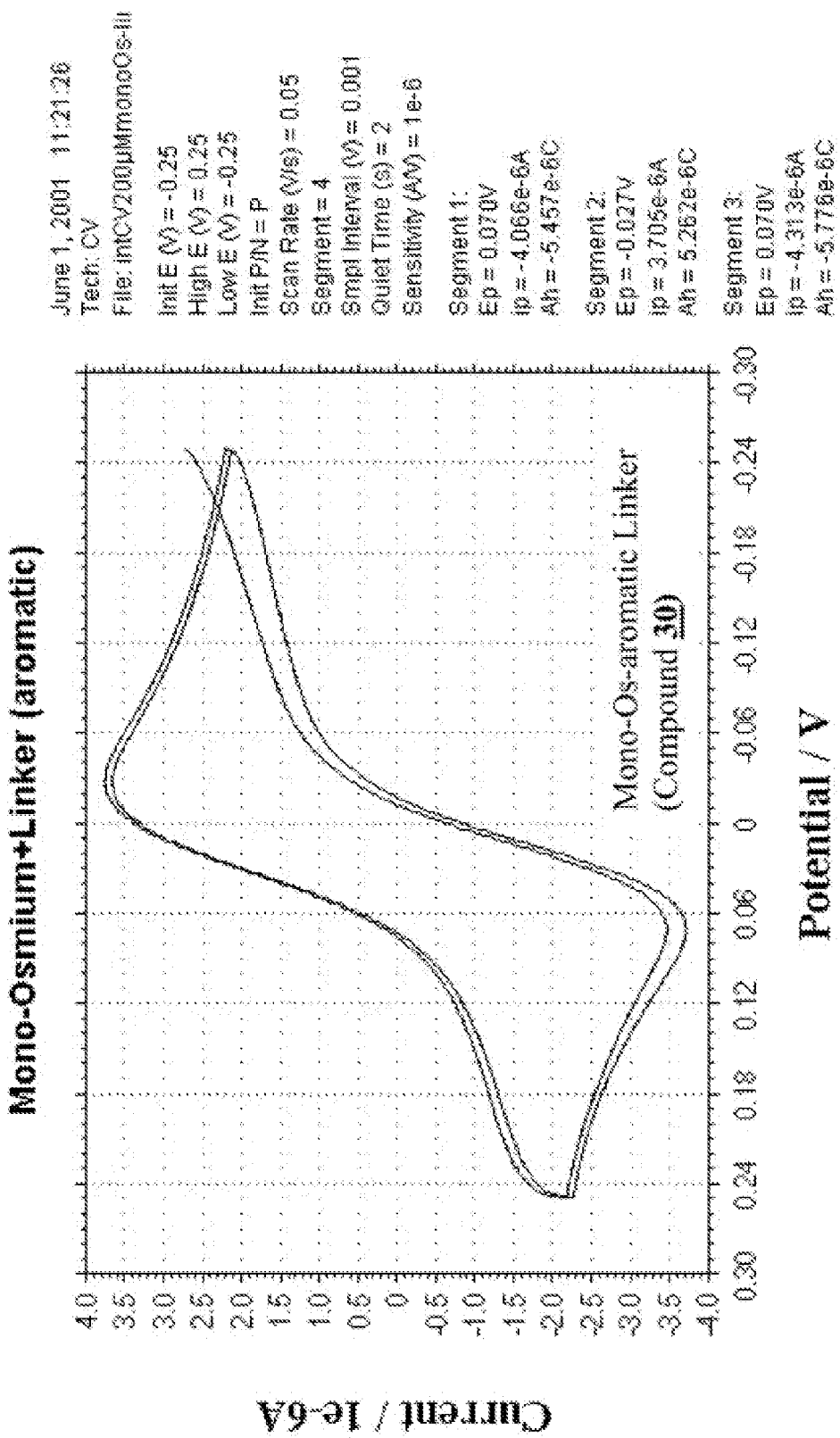
FIG. 51 is a CV spectrum of the mono-osmium aromatic trifluoroacetamido protected linker.
Figure 52:
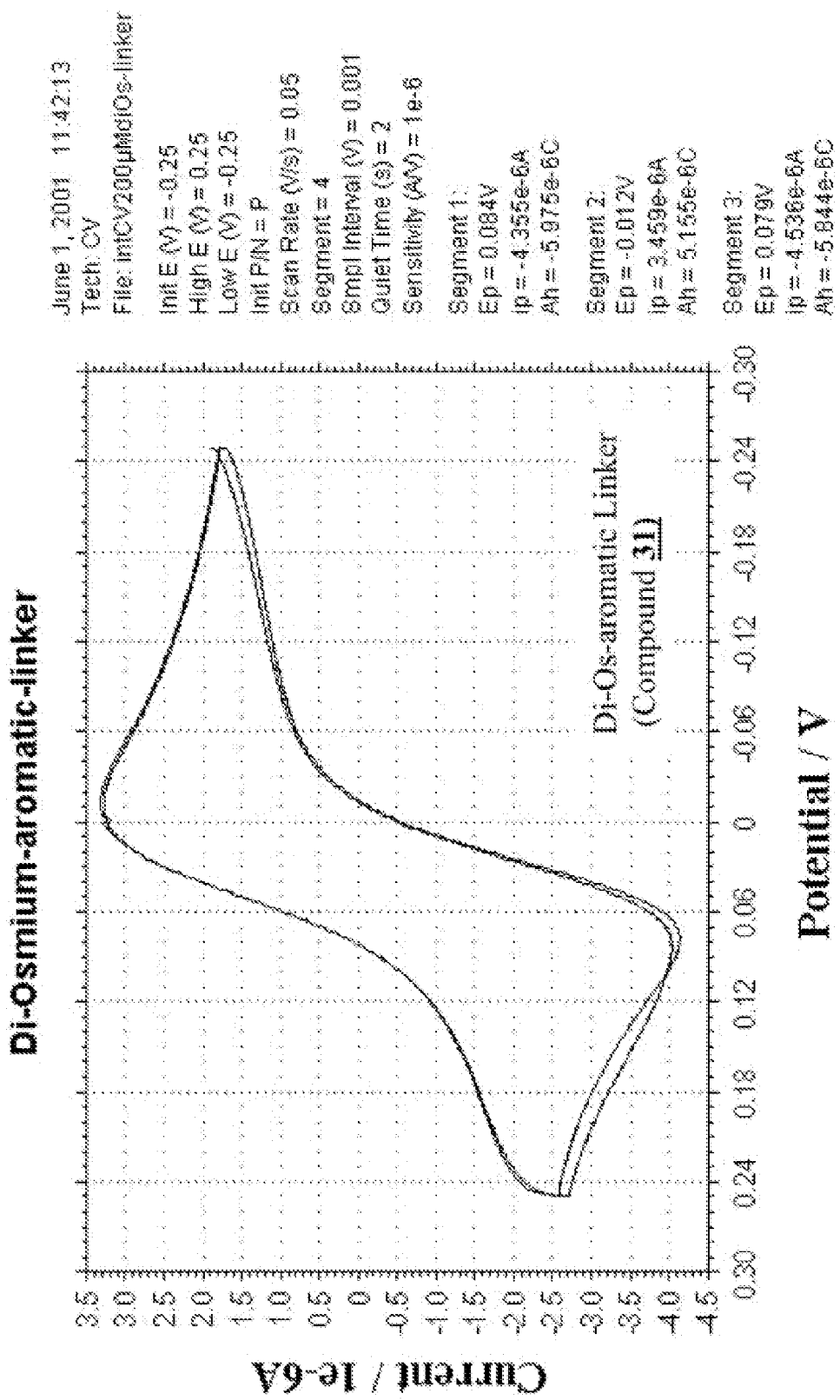
FIG. 52 is a CV spectrum of the di-osmium aromatic linker electrochemical label.
Figure 54:
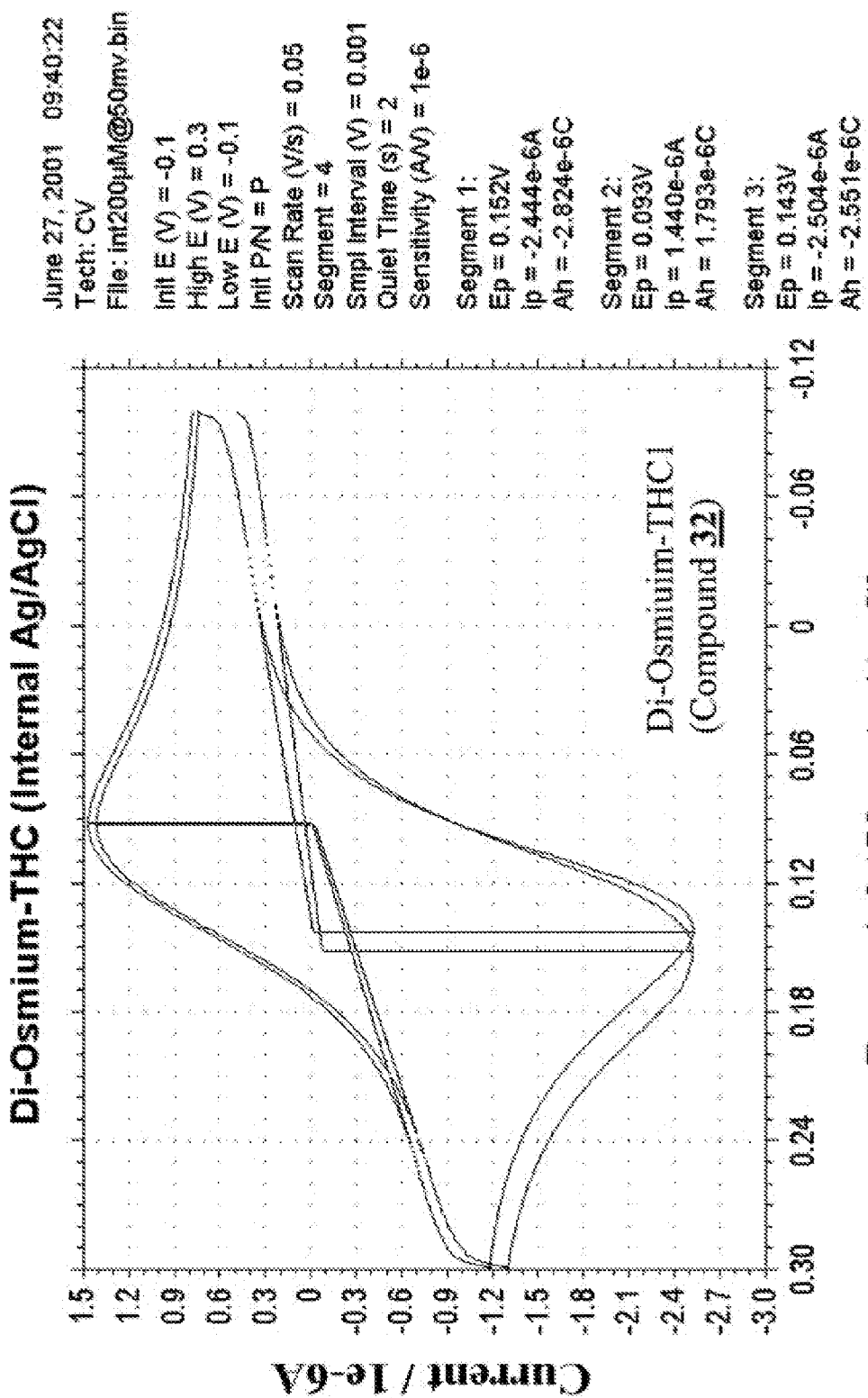
FIG. 54 is a CV spectrum of the di-osmium-THC-1 conjugate.

FIG. 51 and FIG. 54 show normal CVs that were performed with both the mono-osmium-aromatic trifluoroacetomido protected linker (compound 30) and the di-osmium-aromatic linker (compound 31) respectively. The CVs show that the synthesized mediators were redox reversible compounds with a reasonably low $E_{1/2}$ potential of about 20-40 mV vs Ag/AgCl. Both were run at a concentration of 200 μM on planar IDA electrodes with 50 finger pairs with W=21 μm and $W_g$=15 μm.

Figure 53:
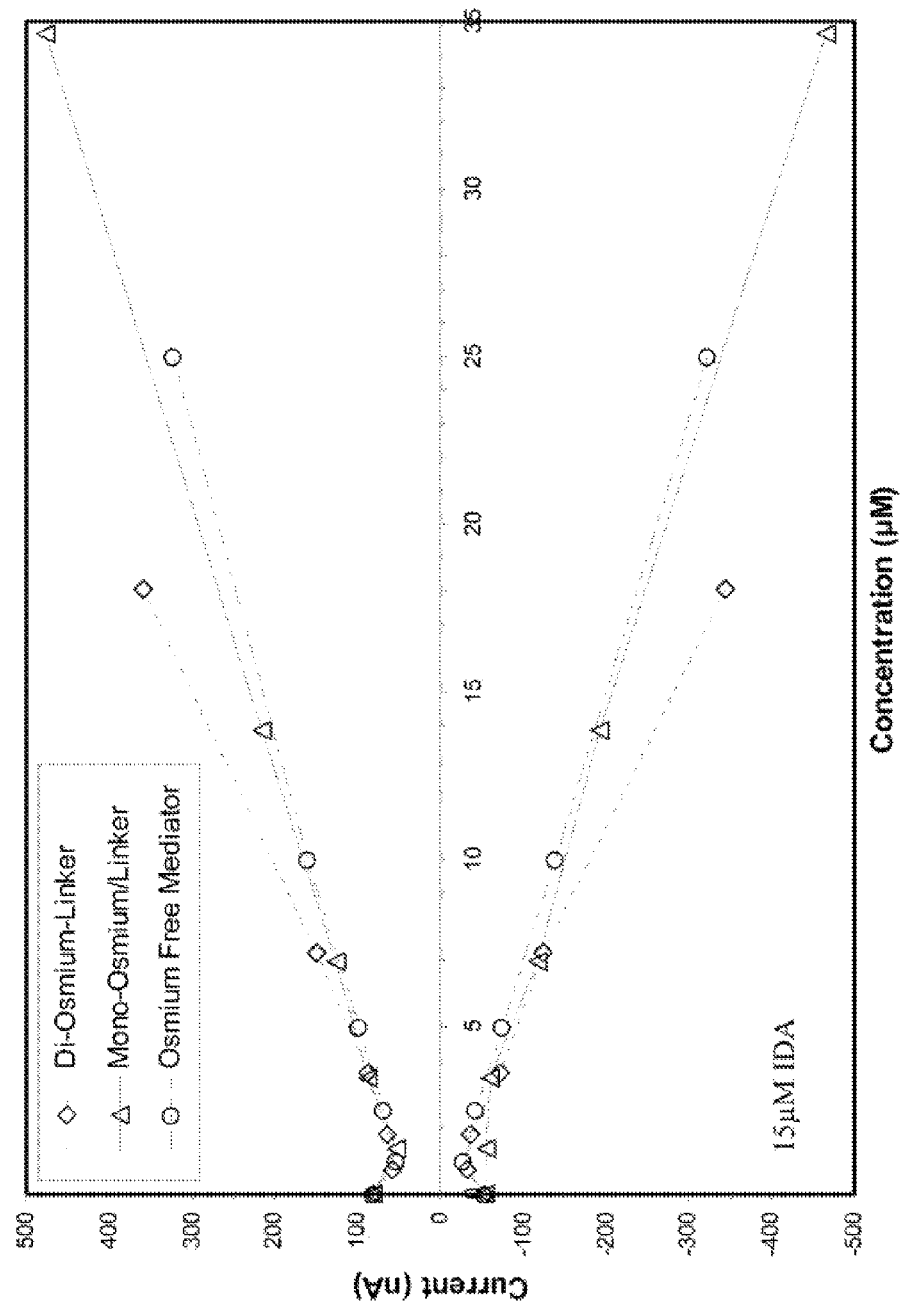
FIG. 53 is a graph comparing the dose response curve of a di-osmium linker, a mono-osmium linker, and bis(2,2'-bipyridyl)imidazole chloro osmium (III) dichloride.

FIG. 53 show a comparison of dose responses for the mono-osmium-aromatic trifluoroacetomido protected linkers (compounds 30 and 31), and osmium free mediator (bis(2,2'-bipyridyl)imidazole chloro osmium (III)dichloride) all run on planar IDA electrodes with 50 finger pairs with W=21 μm and Wg=15 μm. The osmium free mediator and the mono-osmium-aromatic trifluoroacetomido protected linker gave similar response and the di-osmium-aromatic linker gave a slightly improved response. The response of the di-osmium compound was not 2× that one might initially expect with twice the number of redox sites. Some justification for a lower response may be that the larger size (MW) of the di-osmium complex slows the diffusion between electrodes and/or that on average only one site of the di-osmium complex is actually oxidized and reduced (only one osmium center is oxidized or reduced at any time). In any case based upon the CV and a slightly improved dose response curve, this new conjugate proved to be a viable alternative to the mediators with single osmium centers.

FIG. 54 show the CV of di-osmium-THC1 conjugate (compound 32) at a concentration of 200 μM run on planar IDA electrodes with 50 finger pairs with W=21 μm and $W_g$=15 μm. The conjugate stock was prepared in PBST from 0.75 mg of the compound without the use of an organic solvent. The CV shows that the mediator is reversible but the reductive peak appears to be slightly smaller than the oxidation peak's currents. The response is about 50% lower than the di-osmium-aromatic linker (compound 31). The decreased response seems to be indicative of the hydrophobic nature of the THC molecule.

Figure 55:
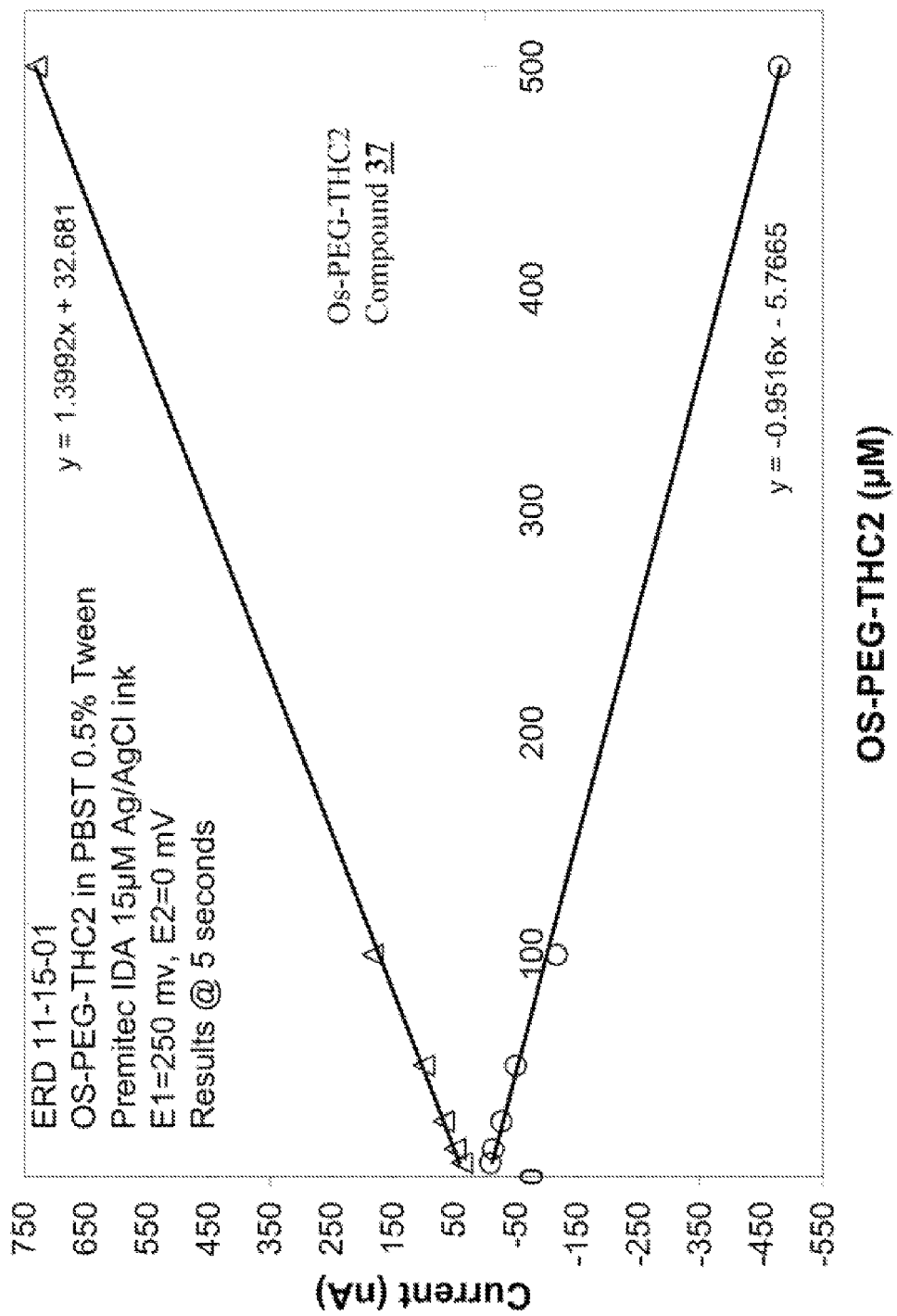
FIG. 55 is a graph of the response of osmium-PEG-THC-2 conjugate.

FIG. 55 is an osmium-PEG-THC-2 (compound 37) dose response curve on planar IDA electrodes with 50 finger pairs with W=21 μm and $W_g$=15 μm. The measurements were controlled with a CHI Instruments bipotentiostat WE1=250 mV and WE2=0 mV. The conjugate stock solution was dissolved in PBST without the use of organic solvents. Serial dilutions were made between 6.25 μM to 500 μM in PBST. 10

μl was and applied into the capillary built over the electrode cell. Similar to the di-osmium-THC1 conjugate (compound 32) the reductive response (slope) is slightly smaller than the oxidation slope. Both slopes are about 10 times smaller that seen with the osmium free mediator. The assay data shown is the result 5 seconds after applying the potentials. The results are the average of 4 replicates.

Figure 56:
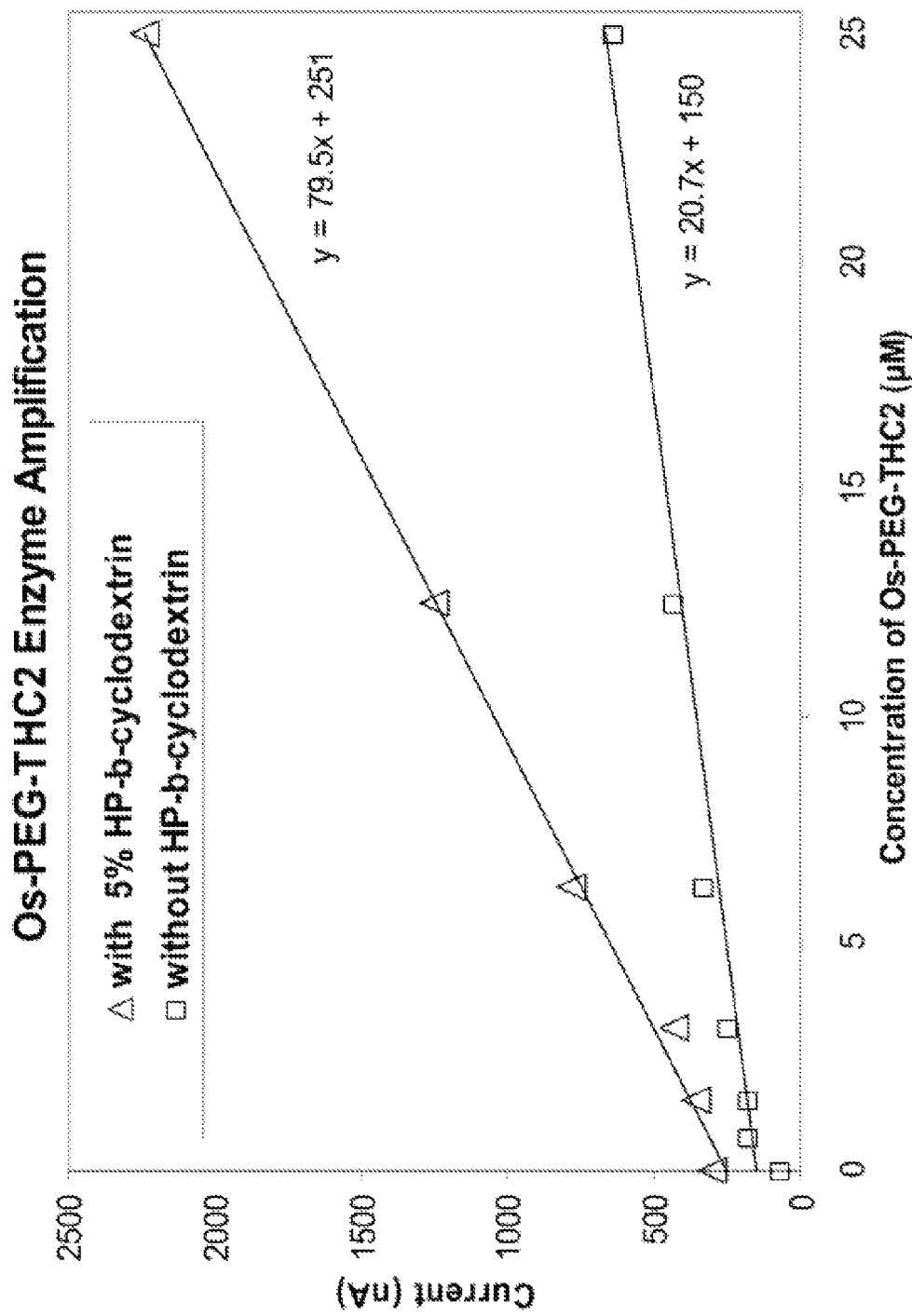
FIG. 56 an enzyme amplified plot of the conjugate response of osmium-PEG-THC-2 electrochemical label with and without hydroxypropylbetacylcodextrin.

FIG. 56 is an osmium-PEG-THC-2 (compound 37) dose response curve with enzyme amplification. The slope of the enzyme amplified conjugate response is improved over the IDA amplification. Also noted is that with the addition of 5% hydroxypropyl-β-cyclodextrin to overcome possible concerns with the hydrophobic nature of the THC, a significant increase is seen in the response.

Figure 57:
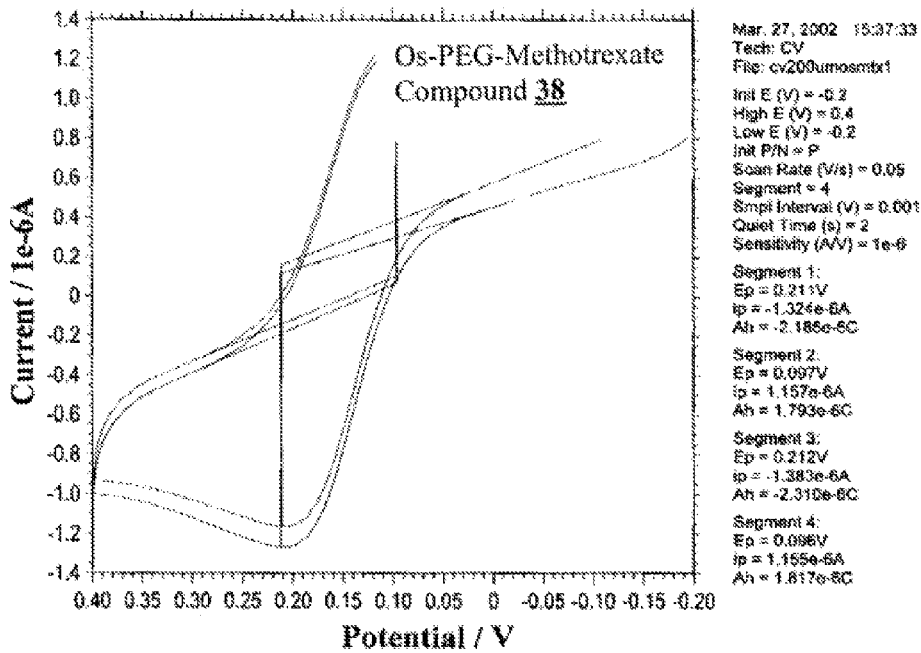
FIG. 57 is a CV spectrum of the osmium-PEG-methotrexate conjugate.

FIG. 57 shows the CV of osmium-PEG-methotrexate (compound 38) at a concentration of 150 μM run on planar IDA electrodes with 50 finger pairs with W=21 μm and $W_g$=15 μm. The conjugate stock was prepared in PBST at 150 μM from 0.49 mg of the compound without the use of an organic solvent. The CV shows a symmetrical reversible redox peaks. In comparison CVs of other mediators, one must take into account the larger finger width of 21 μM and the lower concentration of conjugate use for this CV.

Figure 58:
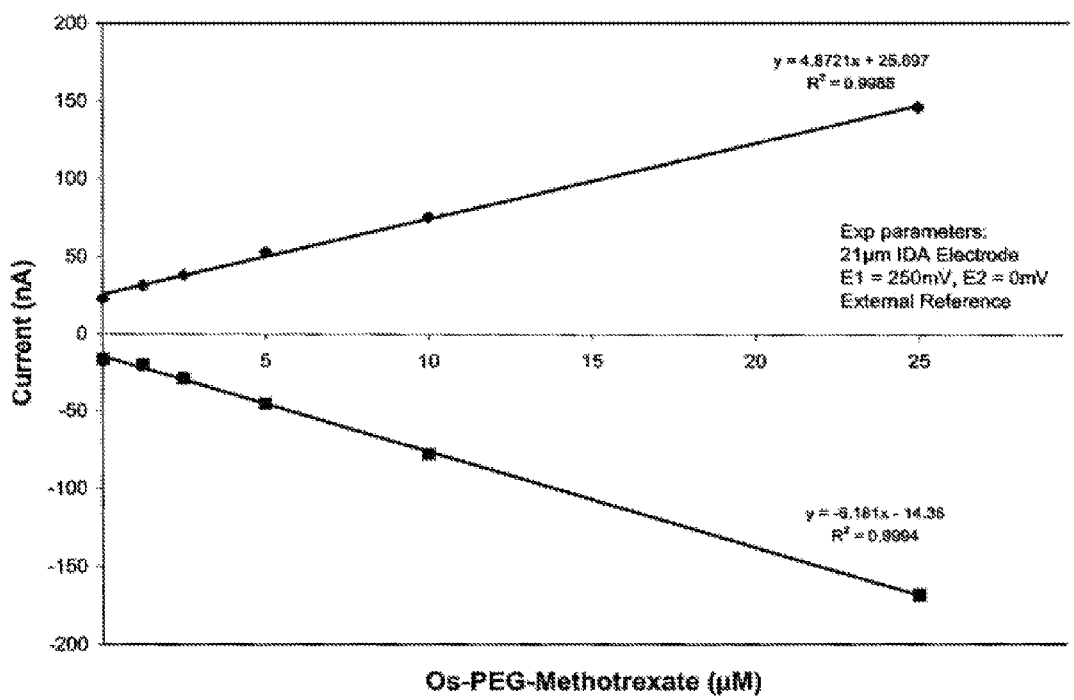
FIG. 58 is a graph of the dose response of osmium-PEG-methotrexate conjugate.

FIG. 58 is an osmium-PEG-methotrexate (compound 38) dose response curve on planar IDA electrodes with 50 finger pairs with W=21 μm and $W_g$=21 μm. The measurements were controlled with a CHI Instruments bipotentiostat WE1=0.25 mV and WE2=0 mV. Dilutions were made in PBST from the 150 μM stock to prepare (25, 10, 5, 2.5 and 1.25 μM concentrations). 20 μL of the solutions were applied to the electrode into the capillary built over the electrode cell using an external Ag/AgCl reference electrode. The 20 μL volume was needed to bridge the gap between the sample in the capillary and the external capillary located just outside the capillary region. The slope of conjugate response for this mediator was larger than that of the osmium-PEG-THC2 response. The results are the average of 4 replicates.

Additional examples are described in an article entitled "The Latest Development in Biosensor Immunoassay Technology for Drug Assays" which is incorporated by reference in its entirety.

Synthesis of Electrochemical Mediator Labels

All solvents were from J. T. Baker. Analytical reverse phase HPLC analyses were performed on an Agilent HP1100 LC/MS system configured with a diode-array detector and a quaternary pump. The LC/MS analyses were performed with a Vydac 218TP54 column (300A, 5μ; C18, 4.6 mm×250 mm) equipped with a Phenomenex KJO-4282 guard kit with AJO-4287 (C-18ODS) cartridge. Chromatographic stream ported post-column into the MS detector. The MSD utilized was run in electrospray positive mode "ES (+) mode".

HPLC fractions were lyophilized. Acetonitrile was evaporated under reduced pressure followed by freezing of the aqueous residue using, for example, a dry ice/acetone bath, followed by freeze-drying using a lyophilizer. The residue was purified by preparative RP-HPLC to give 10.2 mg (6.6× $10^{-3}$ mmol, 20%) of THC-osmium PEG derivative (37), LC/MS M+H 1501.6.

Preparative reverse phase HPLC used a Varian Dynamax radial compression column with 1) R00083221C (Microsorb 60-8, C-18, 250 mm×21.4 mm) with a Varian Dynamax (Rainin) guard module R00083221G (C-18, 8μ) or 2) R00083241C (Microsorb 60-8, C-18, 250 mm×41.4 mm) with a Varian Dynamax (Rainin) guard module R00083241G (C-18, 8μ). The HPLC work was performed using a gradient system of water-acetonitrile containing 0.1% trifluoroacetic acid.

Amphetamine NHS ester (compound was prepared as described in "Dual Analyte Immunoassay", EP 0574782A2. The THC-1 NHS ester (compound 18) is a short linked derivative prepared as described in "Reagents for the Determination of Drugs", EP 0386644. The THC-2 NHS ester (compound 16) is a long chain derivative prepared as described in "Novel Cannabinol Derivatives and Improved Immunoassay", EP 0276732A2. Theophylline amine (compound 11) was prepared according to the procedure published in PCT WO 87/07955. Theophylline NHS ester (compound 12) was prepared by reaction of theophylline amine (compound 11) with terephthalic acid di-N-hydroxysuccinimide ester in the presence of triethylamine. The O—(N-Boc-2-aminoethyl)-O—(N-diglycolyl)-2-aminoethyl)hexaethyleneglycol (compound 33) was purchased from Nova Biochem through VWR.

Preparation of bis(2,2'-bipyridyl)dichloro osmium

To a mixture of 4.18 g (8.6 mmol) of potassium hexachloroosmiate and 3.05 g (19.5 mmol) 2,2'-dipyridyl was added 100 mL of dimethylformamide. The reaction mixture was heated to reflux for 1 h and cooled to room temperature. The resulting reaction mixture was filtered and the residue was washed with 5 mL of DMF. The filtrate was allowed to stir at room temperature and a solution of 4.76 g (0.027 mol) sodium dithionate in 430 mL of water was added to the reaction mixture dropwise. The resulting reaction mixture was placed in an ice-bath to precipitate the desired product. This resulting solid was collected and washed two times with 15 mL of water followed by two times with 15 mL of ether. The resulting brown solid was dried at 50° C. under vacuum (0.5 mm Hg) to give 4.3 g (7.4 mmol, 87%) of desired product as a dark brown solid.

Preparation of 4-(2-tert-Butoxycarbonylamino-ethyl)-imidazole-1-carboxylic acid tert-butyl ester A mixture of 3.68 g (20 mmol) of histamine dihydrochloride, 160 mL acetonitrile, 14 mL (0.10 mol) of triethylamine, and 13.1 g (0.060 mol) of di-tert-butyldicarbonate was allowed to stir at room temperature for three days. The reaction mixture was concentrated, and the residue was washed with 150 mL of hexane. The residue was washed three times with 100 mL of ether. All the ether parts were combined and concentrated to give as a white powder (LC/MS M+NA 334.1).

Preparation of
[2-(1H-Imidazol-4-yl)-ethyl]-carbamic acid tert-butyl ester

To 4-(2-tert-Butoxycarbonylamino-ethyl)-imidazole-1-carboxylic acid tert-butyl ester, were added 100 mL of methanol and 800 mL (5.73 mol) of triethylamine The reaction mixture was allowed to stir at room temperature for four days and concentrated to oil. To the residue were added 40 mL of ether and 80 mL of hexane. This mixture was allowed to stand at room temperature resulting in precipitation of product, as a white solid, which were collected. The yield was 1.7 g (8.0 mmol, 40%) (LC/MS M+H 212.1).

Preparation of Osmium dibipyridyl t-Boc Histamine (Compound 4)

To a mixture of 300 mg (0.52 mmol) of bis(2,2'-bipyridyl) dichloro osmium and 268 mg (1.26 mmol) of histamine t-Boc was added 54 mL of ethanol followed by 1.6 mL (11.4 mmol) of triethylamine. The mixture was allowed to stir at 80° C. for five days and concentrated. The residue was purified by preparative HPLC using a gradient run with water and acetonitrile containing 0.1% trifluoroacetic acid to give 250 mg (0.32 mmol, 61%) of osmium dibipyridyl t-Boc Histamine (compound 4) as a brown powder (LC/MS M+H 749.1).

Preparation of Bis(2,2'-bipyridyl)-histamine-chloro-osmium [Osmium(bP$_y$)$_2$(histamine)Cl] (Compound 5)

To 50 mg (0.063 mmol) of osmium dibipyridyl t-Boc Histamine (compound 4) were added 2 mL methylene chloride and 2 mL of trifluoroacetic acid. The reaction mixture was allowed to stir at room temperature for 20 minutes and concentrated under reduced pressure. To the residue 5 mL of methylene chloride was added and concentrated. This procedure of addition of 5 mL methylene chloride followed by concentration was repeated four more times and the total residue was dried to give 40 mg (0.058 mmol, 93%) of (compound 5) as a brown powder, (LC/MS M+H 649).

Preparation of Amphetamine-Osmium Histamine TFA Protected Conjugate (Compound 9)

To 82 mg (0.104 mmol) of osmium dibipyridyl t-Boc histamine (compound 4) were added 1.5 mL of trifluoroacetic acid and 0.5 mL of 1,2-dichloroethane. The resulting reaction mixture was allowed to stir at room temperature for 30 minutes and then concentrated. To the resulting residue was added 5 mL of methylene chloride, which was then concentrated. The above process of addition of 5 mL of 1,2-methylene chloride and concentration was repeated three additional times and the total dried under reduced pressure for 2 h. To the residue were added 1 mL anhydrous DMF and 0.2 mL (1.43 mmol) of triethylamine. The reaction mixture was allowed to stir while a solution of 50 mg (0.09 mmol) of amphetamine NHS ester in 1 mL of 1, 2 dichloroethane and 0.5 mL of DMF were added dropwise. The resulting reaction mixture was allowed to stir at room temperature 18 hours and then concentrated under reduced pressure. The residue was purified by preparative reverse phase HPLC to give 68 mg (0.060 mmol, 67%) of amphetamine-osmium trifluoroacetamide protected compound (compound 9) as dark brown solid, LC/MS M+H 1083.63.

Preparation of Osmium Amphetamine Conjugate (Compound 10)

To 60 mg (0.053 mmol) of amphetamine-osmium histamine TFA protected conjugate (compound 9) were added 25 mL of 50 mM potassium carbonate and 10 mL of methanol. The reaction mixture was allowed to stir at room temperature for three days and then concentrated. The residue was purified by preparative reverse phase HPLC to give 13.6 mg (0.013 mmol, 25%) of the osmium conjugate (compound 10), LC/MS M+H 987.2. The starting material amphetamine-osmium histamine TFA protected conjugate (compound 9) (18.3 mg) was also recovered.

Preparation of Osmium THC-2 Histamine Conjugate (Compound 17)

To 54 mg (0.068 mmol) of osmium dibipyridyl-t-Boc histamine (compound 4) were added 1.5 mL trifluoroacetic acid and 0.5 mL of methylene chloride. The reaction mixture was allowed to stir for 30 minutes and concentrated. Methylene chloride, 5 mL, was added and resulting solution concentrated. The above procedure of methylene chloride addition and concentration was repeated three more times. To the resulting residue, 1 mL of anhydrous DMF was added followed by 200 µL (1.43 mmol) of triethylamine. The reaction mixture was allowed to stir at room temperature and a solution of 30 mg (0.060 mmol) of THC-2 NHS derivative (compound 16) in 0.5 mL of anhydrous DMF and 1 mL of methylene chloride. The reaction mixture was allowed to stir at room temperature 18 hours and concentrated. The residue was purified by preparative reverse phase HPLC to give 33.3 mg (0.031 mmol) of osmium THC-2 histamine conjugate (compound 17) as brown powder, LC/MS M+H 1034.2.

Osmium Methotrexate Conjugate (Compound 21)

To 57 mg (0.125 mmol) of methotrexate (Sigma) was added 1 mL of anhydrous DMF followed by 22 mg (0.15 mmol) of 4-nitrophenol and 27 mg (0.13 mmol) of N,N'-dicyclohexylcarbodiimide. The resulting reaction mixture was allowed to stir at room temperature for 4 hours and the resulting methotrexate activated ester (compound 20) was used in situ in the next step without isolation.

To 100 mg (0.14 mmol) of osmium dibipyridyl t-Boc histamine (compound 4) was added 1 mL of trifluoroacetic acid. The resulting reaction mixture was allowed to stir at room temperature 30 minutes and concentrated under reduced pressure. To the residue 5 mL of methylene chloride was added and concentrated. The addition of 5 mL methylene chloride and concentration process was repeated four more times. To the residue 1 mL of DMF was added followed by 200 µL (1.43 mmol) of triethylamine. The reaction mixture was allowed to stir at room temperature under argon atmosphere and the activated ester of methotrexate prepared as above (compound 20) was added dropwise. The reaction was allowed to stir for 18 hours at room temperature under argon atmosphere and concentrated under reduced pressure. The residue was purified by preparative reverse phase HPLC to give 52.5 mg (0.046 mmol, 32%) of the osmium methotrexate conjugate (compound 21) as a brown powder, LC/MS M+H 1086.2.

Preparation of Theophylline Osmium Histamine Conjugate (Compound 13)

This was prepared by similar method starting with theophylline NHS ester (compound 12) as described for example in the preparation of osmium THC-2 histamine conjugate (compound 17).

Preparation of PCP-Osmium Histamine Conjugate (Compound 15)

This was prepared by similar method starting from PCP NHS ester (compound 14) as described for example in the preparation of osmium THC-2 histamine conjugate (compound 17).

Preparation of THC-1 Osmium Histamine Conjugate (Compound 19)

This was prepared by similar method starting from THC-1 NHS ester (compound 18) as described for example in the preparation of osmium THC-2 histamine conjugate (compound 17). Solubility of this mediator in PBST was poor and required the use of DMF.

Preparation of (3-tert-Butoxycarbonylmethoxy-5-hydroxymethyl-phenoxy)-acetic acid tert-butyl ester (Compound 22)

To 5 g (35 mmol) of 3,5-dihydroxybenzyl alcohol were added 250 mL of dry DMF, 11.85 mL (80 mmol) of t-butyl-bromoacetate, 14.8 g (107 mmol) of anhydrous potassium carbonate, and 34.5 g (105 mmol) of cesium carbonate followed by 3 g of 4 Å molecular sieves. The resulting reaction mixture was allowed to stir at 80° C. under argon atmosphere. The reaction mixture was allowed to cool to room temperature, filtered, and the residue was washed with 200 mL of ethyl acetate. All the filtrate were combined and concentrated to dryness. The residue was redissolved in 150 mL of diethyl ether, washed three times with 200 mL of water and concentrated. The residue was purified by silica gel column chromatography using 70% diethyl ether in hexane to give 7.5 g (20 mmol, 57%) of (compound 22) as a colorless gum (LC/MS M+Na 391.1).

Preparation of (3-Bromomethyl-5-tert-butoxycarbonylmethoxy-phenoxy)-acetic acid tert-butyl ester (Compound 23)

To 1 g (2.7 mmol) of (compound 22) was added 48 mL of methylene chloride and cooled to −40° C. followed by 640 µL (4.58 mmol) of triethylamine, 400 µL (5.16 mmol) of methanesulphonyl chloride. The resulting reaction mixture was allowed to stir at −40° C. for 3 h. To the reaction mixture were added 32 mL of freshly distilled THF and 800 mg (9.21 mmol) of lithium bromide. The reaction mixture was allowed to stir at 4° C. for 18 hours, and then concentrated to dryness. This was dissolved in 50 mL of methylene chloride and 20 mL of water. The organic layer was separated and the aqueous layer was extracted with four times with 30 mL of methylene chloride. The combined organic layers were dried ($Na_2SO_4$) and concentrated to give 1.16 g (2.68 mmol, 99%) of (compound 23).

Preparation of (3-Azidomethyl)-5-tert-butoxycarbonylmethoxy-phenoxy)-acetic acid tert-butyl ester (Compound 24)

To 1.16 g (2.68 mmol) of the bromo derivative (compound 23) were added 30 mL of anhydrous DMF and 1.79 g (27.5 mmol) of sodium azide at 50° C. under an argon atmosphere for 72 hours. The reaction mixture was cooled to room temperature, filtered, and the residue was concentrated to dryness. To the residue 50 mL of ethyl acetate and 25 mL of water were added. The organic layer was separated and the aqueous layer was extracted with 25 mL of ethyl acetate. The organic layers were combined, dried ($Na_2SO_4$) and concentrated to give 1.04 g (2.64 mmol, 99%) of the azido compound (compound 24) as a gummy white solid, LC/MS M+Na 416.1.

Preparation of (3-Aminomethyl-5-tert-butoxycarbonylmethoxy-phenoxy)-acetic acid tert-butyl ester (Compound 25)

To 2.9 g (7.3 mmol) of (compound 24) were added 140 mL of ethanol, 4.5 g (71.3 mmol) of ammonium formate and 1.39 g of 10% Pd—C. The resulting reaction mixture was allowed to stir at room temperature for 18 hours and filtered through CELITE®. The residue was washed with 50 mL of ethanol. The filtrate was concentrated and redissolved in 150 mL of chloroform. This was washed three times with 75 mL of DI water, dried ($Na_2SO_4$) and concentrated to give 2.4 g (6.53 mmol, 89%) of the amino derivative (compound 25) as a off-white semisolid, LC/MS; M+Na 390.1, 2M+1 735.3.

Preparation of {3-tert-Butoxycarbonylmethoxy-5-[2,2,2-trifluoro-acetylamino)-methyl]-phenoxy}-acetic acid tert-butyl ester (Compound 26)

To 862 mg (2.34 mmol) of (compound 12) were added 20 mL of freshly distilled THF, 1 mL (7.17 mmol) of triethylamine and 426 µL (3.57 mmol) of ethyltrifluoroacetate. The resulting reaction mixture was allowed to stir at room temperature for 18 hours. This was concentrated to dryness and dissolved in 50 mL of chloroform. The organic layer was washed three times with 50 mL of water, dried ($Na_2SO_4$) and concentrated. The residue was purified by silica gel column chromatography using to give 604 mg (1.3 mmol, 56%) of trifluoroacetyl protected product (compound 26) as a white gummy solid LC/MS M+NA 486.

Preparation of {3-Carboxymethoxy-5-[(2,2,2-trifluoro-acetylamino)-methyl]-phenoxy}-acetic acid [Aromatic Trifluoroacetamido Protected Linker] (Compound 27)

To 500 mg (1.07 mmol) of (compound 26) were added 20 mL of methylene chloride and 20 mL of trifluoroacetic acid. The reaction mixture was allowed to stir at room temperature for 72 hours and concentrated. To the residue was added 30 mL methylene chloride and concentrated. The above process of addition of 30 mL methylene chloride and concentration was repeated three more times to give 376 mg (1.07 mmol, 99%) of the diacid derivative (compound 27) as a white solid, LC/MS M+NA 374.

Preparation of {3-Chlorocarbonylmethoxy-5-[(2,2,2-trifluoro-acetylamino)-methyl]-phenoxy}-acetyl chloride (Compound 28)

To 51.2 mg (0.145 mmol) of (compound) were added 3 mL of methylene chloride and 205 µL (2.33 mmol) of oxalyl chloride and 10 mL of anhydrous DMF. The reaction mixture was allowed to stir at room temperature for 18 hours and concentrated. To the residue was added 5 mL of methylene chloride and concentrated. The above process of addition of 5 mL methylene chloride and concentration was repeated three more times to give the diacidchloride (compound 28). This was used in the next step without further purification.

Preparation of Di-Osmium Dibipyridyl Histamine Trifluoroacetamido Protected Aromatic Linker (Compound 29)

Osmium dibipyridyl t-Boc histamine (compound 4), 320 mg (0.407 mmol) was dissolved in 8 mL of methylene chloride and 8 mL of trifluoroacetic acid. After stirring the resulting mixture at room temperature for 20 minutes, the solvents were removed. Methylene chloride was then added and then removed under vacuum. The addition and removal of methylene chloride was repeated three more times. Then the resulting solid was dissolved in 3 mL of methylene chloride and was allowed to stir at room temperature. A solution of all of (compound 28) (prepared above) in 3 mL of methylene chloride was added to the reaction mixture followed by the addition of 2 mL (14.3 mmol) of triethylamine. The reaction mixture was allowed to stir at room temperature under argon atmosphere for three days. Then the mixture was concentrated and purified by preparative reverse phase HPLC to give 55.9 mg (0.033 mmol, 23%) of the di-osmium aromatic trifluoroacetamido protected complex (compound 29) (LC/MS M+H 1614.3) and 71.8 mg (0.070 mmol, 48%) of the mono-osmium aromatic trifluoroacetamido protected complex.

(compound 30) (LC/MS M+H 983.2) with 69.2 mg recovery of osmium(bPy)$_2$(histamine)Cl (compound 5).

Preparation of Di-Osmium Dibipyridyl Histamine Aromatic Linker [Di-Osmium Aromatic Linker] (Compound 31)

To 53.6 mg (0.031 mmol) of di-osmium aromatic trifluoroacetamido protected complex (compound 29) were added 25 mL of 50 mM potassium carbonate and 10 mL of methanol. The reaction mixture was allowed to stir at room temperature for three days and concentrated. The residue was purified by preparative reverse phase HPLC to give 24 mg (0.015 mmol, 47%) of di-osmium dibipyridyl histamine aromatic linker (compound 31) as a brown powder, LC/MS M+H 1519.2.

Preparation of Di-Osmium Dibipyridyl Histamine THC-1 Conjugate [Di-Osmium THC-1 Conjugate] (Compound 32)

To 11 mg (6.9×10$^{-3}$ mmol) of di-osmium dibipyridyl histamine aromatic linker (compound 31) were added 1.96 mL of DMF, 196 µL (1.40 mmol) of triethylamine and 7.86 mg (0.0178 mmol) of THC-1-NHS ester derivative (compound 18). The mixture was allowed to stir at room temperature under argon atmosphere for 18 hours and concentrated. LC/MS indicated desired product formation, (LC/MS M+H 1846.4). The above reaction was repeated by mixing 8 mg (5.03×10$^{-3}$ mmol) of di-osmium dibipyridyl histamine aromatic linker (compound 31), 1.43 mL DMF, 143 µL (1.01 mmol) of triethylamine and 5.72 mg (0.012 mmol) of THC-1-NHS (compound 18). The reaction mixture was allowed to stir at room temperature for 18 hours and concentrated. Both of the reaction products were mixed and purified by preparative reverse phase HPLC to give 8.7 mg (4.5×10$^{-3}$ mmol, 11%) of di-osmium THC-1 conjugate (compound 32) as a brown powder, (LC/MS, M+H 1846.4).

Preparation of Osmium-PEG Linker t-Boc Protected (Compound 35)

To 120 mg (0.20 mmol) of O—(N-Boc-2-aminoethyl)-O—(N-diglycolyl)-2-aminoethyl hexaethylene glycol (compound 33), (Nova Biochem) were added 2 mL of methylene chloride, 128 mg (0.67 mmol) of 1-(3-Dimethylaminopropyl)-3-ethylcarbodiimide hydrochloride, 72 mg (0.62 mmol) of N-hydroxysuccinimide. The reaction mixture was allowed to stir at room temperature for 18 hours. The resulting activated PEG NHS ester (compound 34) was used in situ in the next step without isolation.

To 120 mg (0.15 mmol) of Osmium dibipyridyl t-Boc Histamine (compound 4) was added 2.5 mL of trifluoroacetic acid and the resulting mixture was allowed to stir at room temperature for 1 hour. The reaction mixture was concentrated and 15 mL of methylene chloride was added and concentrated to dryness. To the residue 1.5 mL of DMF was added followed by 500 µL (mmol) of triethylamine. The reaction mixture was allowed to stir at room temperature and the solution of activated PEG NHS ester (compound 34) was added dropwise to the reaction mixture. The reaction mixture was allowed to stir at room temperature for 18 hours and concentrated. The residue was purified by preparative reverse phase HPLC to give 93 mg (0.074 mmol, 36%) of Osmium PEG linker t-Boc protected (compound 35) as a brown powder, LC/MS M+H 1216.4.

Preparation of Osmium PEG Linker (Compound 36)

To 90 mg (0.071 mmol) of osmium PEG linker t-Boc protected (compound 35) was added 2 mL of trifluoroacetic acid. The resulting reaction mixture was allowed to stir at room temperature for 40 minutes and concentrated to give 81 mg (0.070 mmol, 99%) of the osmium PEG linker (compound 36) as a dark brown thick gum, LC/MS M+H 1116.2.

Preparation of Osmium PEG THC-2 Conjugate (Compound 37)

To 39 mg (0.033 mmol) of osmium PEG linker (compound 36) were added 1 mL of DMF and 200 µL (1.43 mmol) of triethylamine. The reaction mixture was allowed to stir at room temperature under argon atmosphere and a solution of 16 mg (0.032 mmol) of THC-2 NHS ester (compound 16) in 1 mL of methylene chloride was added dropwise to the reaction mixture. The reaction was allowed to stir at room temperature for 18 hours and concentrated under reduced pressure. The residue was purified by preparative reverse phase HPLC to give 10.2 mg (6.6×10$^{-3}$ mmol, 20%) of osmium PEG THC-2 conjugate (compound 37), LC/MS M+H 1501.6.

Osmium PEG Methotrexate Conjugate (Compound 38)

To 19 mg (0.041 mmol) of methotrexate (Sigma) was added 0.4 mL of anhydrous DMF followed by 8 mg (0.06 mmol) of 4-nitrophenol and 9 mg (0.043 mmol) of N,N'-dicyclohexylcarbodiimide. The resulting reaction mixture was allowed to stir at room temperature for 4 hours and the resulting activated ester (compound 20) was used in situ in the next step without isolation.

To 22.9 mg (0.019 mmol) of osmium PEG linker (compound 36) was added 500 µL of DMF followed by 100 µL (0.71 mmol) of triethylamine. The reaction mixture was allowed to stir at room temperature and the solution of methotrexate activated ester prepared above (compound 20) was added dropwise. The reaction mixture was allowed to stir at room temperature for 18 hours and concentrated. The residue was purified by preparative reverse phase HPLC to give 7.8 mg (4.9×10$^{-3}$ mmol, 25%) of osmium PEG methotrexate conjugate (compound 38), LC/MS M+H 1554.5.

Preparation of 4-amino-hepanedioic acid diethyl ester hydrochloride (Compound 39)

To 2 g (8.6 mmol) of diethyl 4-oxopimelate was added 20 mL of methanol, followed by 6.7 g (86 mmol) of ammonium acetate, 713 mg (8.6 mmol) of sodium acetate, and 5 mL of glacial acetic acid. The reaction mixture was allowed to stir at room temperature for 18 hours and concentrated. To the residue 150 mL ethyl acetate and 100 mL of aqueous saturated solution of sodium bicarbonate was added. The organic layer was separated and the aqueous layer was extracted with an additional 100 mL of ethyl acetate. Organic layers were combined and washed two times with 100 mL of saturated sodium bicarbonate, dried (Na$_2$SO$_4$) and concentrated to give an oil. To the oil 5 mL of 2M HCl in diethylether was added. White solid precipitated out which was filtered to give 1.2 g (4.48 mmol, 52%) of the amino product as a hydrochloride salt (compound 39).

Preparation of 4-tert Butoxycarbonylamino-heptanadioic acid diethyl ester (Compound 40)

To 500 mg (1.86 mmol) of the amino product (compound 39) was added 15 mL of methylene chloride followed by 1.2 mL (8.5 mmol) of triethylamine. To the reaction mixture 646 mg (2.95 mmol) of di-t-butyldicarbonate was added followed by 25 mg (1.12 mmol) of 4-dimethylaminopyridine. The reaction mixture was allowed to stir at room temperature for 18 hours and concentrated under reduced pressure. To the residue 150 mL of chloroform was added and washed with two times with 100 mL of water. The organic layer was dried ($Na_2SO_4$) and concentrated to give an oil. This was purified by silica gel column chromatography using 8:2 hexane:ethyl acetate to give 396 mg (1.19 mmol, 64%) of the 4-tert Butoxycarbonylamino-heptanadioic acid diethyl ester product (compound 40).

Preparation of 4-tert-Butoxycarbonylamino-haptanedioic acid (Compound 41)

4-tert Butoxycarbonylamino-heptanadioic acid diethyl ester (compound 40), 380 mg (1.14 mmol), was dissolved in THF containing 3 mL methanol. To the reaction mixture a solution of 481 mg (11.5 mmol) of lithium hydroxide hydrate in 6 mL of water was added and the reaction mixture was allowed to stir at room temperature for 18 hours. This was concentrated under reduced pressure. Five mL of water was added and the pH of the solution was adjusted to pH-5 by using conc. $H_3PO_4$. The reaction mixture was extracted with 3 times 75 mL of ethyl acetate. The combined organic layers were dried ($Na_2SO_4$) and concentrated to give 310 mg (1.12 mmol) of (compound 41) as white powder [LR-MS-ER (−) (M−H 274.2)].

Preparation of 4-tert-Butoxycarbonylamino-heptanedioic acid bis-(2,5-dioxo-pyrrolidin-1-yl)ester (Compound 42)

To 44 mg (0.15 mmol) of 4-tert-Butoxycarbonylamino-haptanedioic acid (compound 41) were added 5 mL of methylene chloride, 76 mg (0.39 mmol) of 1,3-dimethylaminopropyl-3-ethylcarbodiimide hydrochloride and 46 mg (0.39 mmol) of N-hydroxysuccinimide. The reaction mixture was allowed to stir at room temperature for 18 hours. 15 mL of methylene chloride was added. The organic layer was washed with two times with 15 mL of water, two times with 15 mL of saturated sodium bicarbonate and once with 15 mL of water. The organic layer was dried ($Na_2SO_4$) and concentrated under reduced pressure to give 39 mg (0.08 mmol, 52%) of the 4-tert-Butoxycarbonylamino-heptanedioic acid bis-(2,5-dioxo-pyrrolidin-1-yl)ester product (compound 42) as a white solid.

Preparation of Di-Osmium t-Boc Protected Aliphatic Linker (Compound 43)

To 20 mg (0.040 mmol) of 4-tert-Butoxycarbonylamino-heptanedioic acid bis-(2,5-dioxo-pyrrolidin-1-yl)ester (compound 42) was added 44 mg (0.064 mmol) of osmium(bPy)$_2$ (histamine)Cl (compound 5), followed by 2 mL methylene chloride and 0.5 mL DMF. To the reaction mixture 200 µL (1.43 mmol) of triethylamine is added and the reaction mixture is allowed to stir at room temperature for 24 to 48 hours as needed for the reaction to complete. The reaction mixture was concentrated under reduced pressure and purified by preparative reverse phase HPLC to give the di-osmium t-Boc protected aliphatic linker (compound 43).

Preparation of Di-Osmium Aliphatic Linker (Compound 44)

To 10 mg of di-osmium t-Boc protected aliphatic linker (compound 43) was added 1 ml trifluoroacetic acid and allowed to stir at room temperature between 1-2 hours. This was concentrated under reduced pressure to give di-osmium aliphatic linker (compound 44).

Preparation of Biimidazole (Compound 45)

To 25 ml of glyoxal (40 wt % in water) was added 25 mL of water. The reaction mixture was cool in an ice-bath and ammonia gas was bubbled slowly through the mixture for 7 hours. The reaction mixture was filtered to give 710 mg of bidiimdazole (compound 45) as a gray colored powder. This was used in the next step without further purification, LC/MS M+H 135.0.

Preparation of Dimethyl Biimidazole (Compound 46)

To 60 mg (0.44 mmol) of biimidazole was added 1 mL of anhydrous DMF. The reaction mixture was cooled in an ice-bath and 27 mg (0.67 mmol) of NaH (60% in oil) was added. The reaction mixture was allowed to stir at 0° C. for 1 hour. 140 µL (0.92 mmol) of methyl p-toluene sulfonate was added and the reaction mixture was allowed to stir an additional 1 h at 0° C. and then two days at room temperature. The reaction mixture was concentrated and purified by silica gel column chromatography using 50% ethyl acetate in methanol to give 60 mg (0.36 mmol, 83%) of dimethyl biimidazole (compound 46), LC/MS M+H 163.1.

Preparation of Osmium di biimidazole dichloride (Compound 47)

To 150 mg (0.50 mmol) of OsCl$_3$ was added 112 mg (0.69 mmol) of dimethylbiimidazole (compound 46) followed by 280 mg (6.6 mmol) of lithium chloride and 10 mL of anhydrous DMF. The resulting reaction mixture was allowed to reflux under argon atmosphere for 3.5 h and concentrated. The residue was purified by preparative RP-HPLC to give 95 mg (0.15 mmol, 30%) of osmium di biimidazole dichloride (compound 47) as a dark brown powder, LC/MS M+H 586.0.

Preparation of Osmium dibiimidazole hist-t-Boc (Compound 48)

To 50 mg (0.080 mmol) of osmium dibiimidazole dichloride (compound 47) was added 71 mg (0.33 mmol) of [2-(1H-Imidazol-4-yl)-ethyl]-carbamic acid tert-butyl ester (compound 3), followed by 300 µL (2.14 mmol) of triethylamine and 10 mL of ethanol. The mixture was heated to reflux for 18 hours and concentrated. The residue was purified by preparative reverse phase HPLC to give 13 mg (0.016 mmol, 20%) of osmium di-biimidazole hist-t-Boc (compound 48) as a dark brown powder LC/MS M+H 761.2.

Preparation of Osmium (Dimethyl Biimidazole)$_2$ Histamine Linker (Compound 49)

To 4 mg (5.02×10$^{-3}$ mmol) of osmium dibiimidazole hist-t-Boc (compound 48) were added 750 µL of methylene chloride and 750 µL of trifluoroacetic acid. The resulting reaction mixture was allowed to stir at room temperature for 20 minutes and concentrated under reduced pressure. To the residue 5 mL of methylene chloride was added and concentrated. The addition of methylene chloride and concentration process was repeated three more times and the residue was dried to give 3 mg (4.3×10$^{-3}$ mmol, 88%) of osmium (dimethyl biimidazole)$_2$ histamine linker (compound 49), LC/MS M+H 661.1.

The osmium (dimethyl biimidazole)$_2$ histamine linker was prepared as an example of a mediator that should have a lower redox potential. Lower redox potentials are of interest for electrochemical assays to avoid interfering compounds that readily oxidize at higher potentials. Lower mediators are also needed for methods of mixed mediators where the redox potential of each mediator needs to be separated by a minimum of 50-100 mV to allow independent measurement of each mediator with a bipotentiostat as discussed in U.S. Pat. No. 6,294,062. A CV was performed with unpurified material of this mediator by dissolving 1 mg of the mediator into 1 ml of PBST for a concentration of about 1.4 mM. The CV indicated that the $E_{1/2}$ potential for this mediator was significantly lower that the other mediators prepared. The $E_{1/2}$ potential was about −520 mV vs. Ag/AgCl.

What is claimed is:

1. A compound of the formula III:

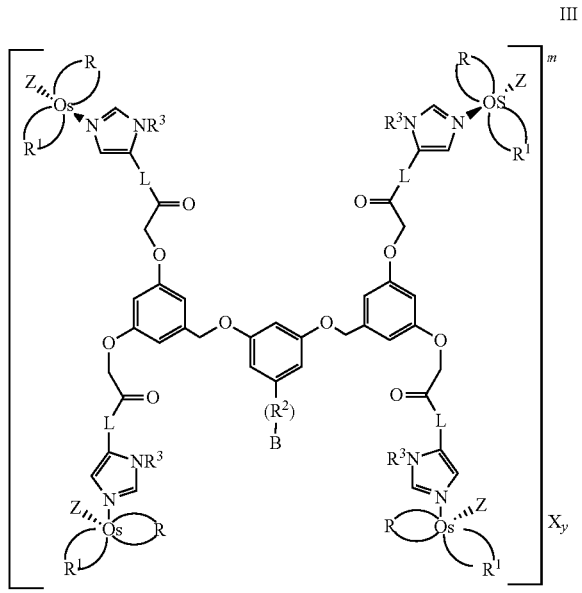

III wherein, R and $R^1$ are the same or different and each can be selected from: 2,2'-bipyridyl, 4,4'-disubstituted-2,2'-bipyridyl, 5-5'-disubstituted-2,2'-bipyridyl, 1,10-phenanthrolinyl, 4,7-disubstituted-1,10-phenanthrolinyl, 5,6-disubstituted-1,10-phenanthrolinyl, or N,N'-dimethyl 2,2'-biimidazole, wherein each substituent is a methyl, ethyl, or phenyl group, and where the R and $R^1$ groups are coordinated to Os through their nitrogen atoms, $R^2$ is a saturated or unsaturated, substituted or unsubstituted, straight or branched chain, hydrocarbyl group having 1-10 carbon atoms; —$R^3$ is H, $CH_3$ or $C_2H_5$; L is $(CH_2)_i$ Q wherein i is an integer between 1 and 10, and Q is O, S, or $NR^3$; B is a group comprising a ligand capable of binding to a specific analyte binding partner; X is a counter ion; y is selected to provide a neutral salt; and m is from 4-8.

2. The compound of claim 1 wherein R and $R^1$ are the same and are selected from 2,2'-bipyridyl, 4,4'-disubstituted-2,2'-bipyridyl, or 5-5'-disubstituted-2,2'-bipyridyl substituted with a methyl, an ethyl or a phenyl group.

3. The compound of claim 1 wherein L is —$(CH_2)_nNR^3$ and n is an integer between 1 and 10.

4. The compound of claim 1 wherein the substituent $R^2$ is a saturated aliphatic group having between 1 and 10 carbons.

5. The compound of claim 1 wherein B comprises an epitope recognizable by an antibody capable of specific binding to an analyte.

6. The compound of claim 1 wherein B comprises an epitope capable of binding to an analyte selected from the group consisting of: a biowarfare agent, an abused substance, a therapeutic agent, an environmental pollutant, a protein or a hormone.

7. The compound of claim 1 wherein L is —$(CH_2)_nS$ and n is an integer between 1 and 10.

8. The compound of claim 1 wherein X is selected from the group of:
chloride, bromide, iodide, fluoride, tetrafluoroborate, perchlorate, nitrate, sulfate, carbonate, and sulfite.

* * * * *